United States Patent [19]

Clement

[11] Patent Number: 5,578,737
[45] Date of Patent: Nov. 26, 1996

[54] CHLORINATION PROCESS, ALKYLATION OF PRODUCTS OF SAID PROCESS AND SOME PRODUCTS THEREOF

[75] Inventor: Katherine S. Clement, Lake Jackson, Tex.

[73] Assignee: The Dow Chemical Company, Midland, Mich.

[21] Appl. No.: 342,515

[22] Filed: Nov. 21, 1994

Related U.S. Application Data

[60] Division of Ser. No. 90,597, Jul. 12, 1993, Pat. No. 5,387,725, which is a continuation-in-part of Ser. No. 789,232, Nov. 7, 1991, abandoned.

[51] Int. Cl.⁶ .................................................. C07D 311/96
[52] U.S. Cl. .................................................. 549/331
[58] Field of Search .............................. 568/779; 549/331

[56] References Cited

U.S. PATENT DOCUMENTS

| | | | |
|---|---|---|---|
| 3,225,106 | 12/1965 | Rabinowitz | 570/190 |
| 3,399,241 | 8/1968 | Smith | 568/812 |
| 3,484,482 | 12/1969 | Schmerling | 568/812 |
| 3,627,731 | 12/1971 | Curcio et al. | 570/206 |
| 3,726,932 | 4/1973 | Mullin et al. | 570/245 |
| 3,830,862 | 8/1974 | Meyers et al. | 570/245 |
| 3,876,689 | 4/1975 | Meyers et al. | 570/244 |
| 3,896,164 | 7/1975 | Meyers et al. | 570/245 |
| 3,935,289 | 1/1976 | de Radzitzky et al. | 570/246 |
| 3,949,001 | 4/1976 | Meyers et al. | 570/245 |
| 3,953,494 | 4/1976 | Meyers et al. | 568/420 |
| 3,983,146 | 9/1976 | Tresper et al. | 568/718 |
| 3,992,432 | 11/1976 | Napier et al. | 570/727 |
| 4,008,287 | 2/1977 | Verbrugge et al. | 510/199 |
| 4,024,194 | 5/1977 | Corn, Jr. | 568/724 |
| 4,049,721 | 9/1977 | Corn, Jr. et al. | 568/718 |
| 4,105,702 | 8/1978 | Mullin et al. | 570/246 |
| 4,132,611 | 1/1979 | Baizer et al. | 204/59 |
| 4,192,822 | 3/1980 | Sweeney et al. | 570/245 |
| 4,226,783 | 10/1980 | Marsh | 570/199 |
| 4,297,514 | 10/1981 | Ma | 568/321 |
| 4,467,122 | 8/1984 | Szabolcs | 568/727 |
| 4,503,266 | 3/1985 | Szabolcs | 568/720 |
| 4,593,144 | 6/1986 | Chupp et al. | 568/936 |
| 4,612,350 | 9/1986 | Parker | 568/331 |
| 4,675,458 | 6/1987 | Riemana et al. | 568/710 |
| 4,684,678 | 8/1987 | Schultz et al. | 523/466 |
| 4,786,668 | 11/1988 | Dewhirst | 523/445 |
| 4,786,669 | 11/1988 | Dewhirst | 523/445 |
| 4,922,038 | 5/1990 | Krespan et al. | 570/175 |
| 4,931,594 | 6/1990 | Knebel et al. | 568/727 |
| 4,980,234 | 12/1990 | Almer et al. | 428/414 |
| 5,001,281 | 3/1991 | Li | 570/727 |
| 5,009,679 | 4/1991 | Angus et al. | 568/779 |
| 5,110,993 | 5/1992 | Hay et al. | 568/718 |
| 5,387,725 | 11/1994 | Walker et al. | 568/779 |

FOREIGN PATENT DOCUMENTS

| | | | |
|---|---|---|---|
| 1070426 | 3/1989 | Japan | 568/721 |
| 172775 | 9/1964 | U.S.S.R. | 568/719 |
| 172775 | 8/1965 | U.S.S.R. | |
| 876662 | 10/1981 | U.S.S.R. | 568/717 |

OTHER PUBLICATIONS

Reutov et al. in *CH–Acids*, pp.96–100, 146–159 and 182–189, (1978).

Ida Smedley in *J. Chem. Soc.* 87 (1905) pp. 1249–1255.

Ray and Albertson in *J. Am. Chem. Soc.*, 70, pp. 1154–1155.

Greenhow, Harris, and White in *J. Chem. Soc.*, pp. 3116–3121 (1954) (CA 50:263).

Ol'dekop and Kalinina in *Zhurnal Obshchei Khimii*, 30, pp. 3358–3361 (1960) (CA 55:18632).

Herbert O. House in *Modern Synthetic Reactions*, 3, pp. 156–162 (1965).

Makoszu, et al. in *Tetrahedron Lett.*, 53 (1969) pp. 4659–4662.

P. W. Morgan in *Macromolecules* (1970) pp. 536–544.

Susuki and Tsuji in *J. Org. Chem.* 35, No. 9, (1970) pp. 2982–2986.

V. Heasley et al. in *J. Org. Chem.* 39, No. 5, pp. 736–737 (1974).

A. Brandstrom in "Principles of Phase–Transfer Catalysis by Quaternary Ammonium Salts" in V. Gold et al (ed) *Advances in Physical Organic Chemistry* (1977) pp. 267–330.

E. Dehmlow et al in *Tetrahedron Lett.* 27 (1977) pp. 2361–2364.

Meyers et al in *Cayalysis in Organic Syntheses* pp. 197–278 (1977).

Alneri, Bottaccio, and Carletti in *Tetrahedron Lett.* 24, pp. 2117–2118 (1977).
Arnold and Kulenovic in *J. Org. Chem* 43, No. 19, (1978) pp. 3687–3689.
Magid et al in *J. Org. Chem.*, 44, No. 3, pp. 359–363 (1979).
Jonczyk, Kwast, and Makosza in *J. Org. Chem*, 44 No. 7 (1979) pp. 1192–1194.
Lauritzen et al in *Acta Chemica Scandinavica* 35, pp. 263–268 (1981).
Chen et al. in *Journal of App. Polmer Source* vol. 27, 3289–3312 (1982).
Dehmlow and Dehmlow in *Phase Transfer Catalysis* pp. 1–22 (1983).
Reeves et al in *Israel Journal of Chemistry* 26, pp. 225–228 (1985).
Chupp et al, in *Synthesis* 1986 (2) pp. 224–226.
Holloway, J. G. "Low Flammability Epoxy Polymers via 9,9–(Bis(4,4'–aminophenyl) fluorene, disseitation" San Jose State University, California, Aug. 1984.
Chemical Abstract 5219e, vol. 64, 1966.
Chemical Abstract 68812s, vol. 70, 1969.
Chemical Abstract 64380e, vol. 75, 1971.
Kajigaeshi et al. in *Tetrahedron Lett.* vol. 29, No. 45, (1988) pp. 5783–5786.
Chemical Abstracts 62: 10551b, vol. 62, 1965.
Chemical Abstracts 63: 14991d, vol. 63, 1965.
Zinke et al., "J. Prakt. Chem." vol. 156 pp. 97–102 (1940) CA.35:1178 (1941).

*Primary Examiner*—Werren B. Lone

[57] ABSTRACT

Compounds having acidic protons and a molecular structure which can delocalize the electron density of the conjugate base (target compounds) are chlorinated by contacting such compounds with a perchloroalkane and aqueous base in the presence of a phase transfer catalyst which is an tetraalkylammonium hydroxide. Chlorinated products, preferably gem-dichloro compounds, are produced. The gem-dichloro compounds are useful for alkylation of aromatic compounds. For instance fluorene is chlorinated to form 9,9-dichlorofluorene which is reacted with such compounds as phenol or aniline to form such compounds as 9,9-bis(hydroxyphenyl)fluorene, 9,9-bis(aminophenyl)fluorene, or 9-aminophenyl-9-chlorofluorene.

13 Claims, No Drawings

CHLORINATION PROCESS, ALKYLATION OF PRODUCTS OF SAID PROCESS AND SOME PRODUCTS THEREOF

CROSS-REFERENCE TO RELATED APPLICATION

This is a divisional of application Ser. No. 08/090,597 filed Jul. 12, 1993 now U.S. Pat. No. 5,387,725 which is a continuation in part of U.S. application Ser. No. 07/789,232 filed Nov. 7, 1991, now abandoned which is incorporated herein in its entirety.

This invention relates to chlorination, particularly to chlorination of organic compounds having acidic protons. The invention also relates to subsequent reaction of certain chlorinated products, more particularly the use of these products to alkylate aromatic compounds.

Products of compounds such as fluorene in which the acidic protons have been replaced by chlorine undergo alkylation reactions which are useful in preparing other compounds such as bis(hydroxyphenyl)fluorenes and bis(aminophenyl)fluorenes and other functionally substituted aromatic compounds which in turn find applications as monomers for high performance polymers. It is particularly important that the chlorination be specific to produce the desired isomers, preferably in the substantial absence of other chlorination products. For instance, in the case of chlorination of fluorene to produce 9,9-dichlorofluorene it is very important that chlorination of the aromatic rings be avoided.

Ida Smedley reported a preparation of 9,9-dichlorofluorene in 1905 from heating fluorenone and a slight excess of phosphorus pentachloride (J. Chem. Soc. 87, 1249 (1905). Smedley did not report a yield, but did mention that the product contained fluorenone and required recrystallization from benzene. Ray et al. repeated Smedley's method and attained a 66 weight percent yield. (J. Amer. Chem. Soc., 70, 1954 (1948).) Ray et al report that the pure product is quite stable if protected from moisture, but that samples of impure material decomposed within a week to give a sticky green-yellow mass with the sharp odor of hydrogen chloride.

Chlorinations of compounds having acidic protons and a molecular structure which can delocalize the electron density of the conjugate base such as fluorene using common chlorination agents such as chlorine, sulfuryl chloride, N-chlorosuccinimide and phosphorus pentachloride are generally disadvantageous because the products of such reactions exhibit substitution on the aromatic rings, instead of substitution of the acidic protons. Therefore, it is not feasible to prepare 9,9-dichlorofluorene from fluorene using conventional chlorination technology.

A procedure for the preparation of 9,9-dichlorofluorene directly from fluorene, without fluorenone as an intermediate, was reported by Reeves et al. in Israel J. Chem. 26, 225 (1985). Tetrabutylammonium bromide was used as a phase transfer catalyst to chlorinate such compounds as fluorene, phenylpropanone, acetophenone, 1-chloroacetophenone, p-methoxyacetophenone, benzoin ethyl ether, p-nitroacetophenone, deoxybenzoin, and xanthene using carbon tetrachloride in an organic phase as chlorine source with an aqueous hydroxide phase. It was reported that use of potassium carbonate in the aqueous phase in the attempted chlorination of p-nitroacetophenone resulted in no reaction. Using this reaction for the chlorination of fluorene, Reeves et al. reported a 51.9 percent yield of 9,9-dichlorofluorene. Other reaction conditions and time for the chlorination of fluorene are not given. A 57 percent yield was reported by Reeves for production of xanthone from xanthene using the procedure.

It would be desirable to have a selective process for chlorinating compounds which have acidic protons and a molecular structure which can delocalize the electron density of the conjugate base such that replacement of the acidic hydrogens is the predominant reaction but in greater yields and/or shorter reaction times than those achieved when following the process reported by Reeves et al.

9,9-Bis(hydroxyphenyl)fluorene is typically prepared from fluorenone such as by reaction of fluorenone with phenol in the presence of such compounds as beta-mercaptopropionic acid and anhydrous hydrogen chloride (P. W. Morgan, *Macromolecules*, 3, 536 (1971); or in the presence of zinc chloride and anhydrous hydrogen chloride (U.S. Pat. No. 4,467,122). Alternatively, fluorenone has been converted to 9,9-dichlorofluorene and subsequently reacted with phenol to produce the 9,9-bis(hydroxyphenyl)fluorene, such as by the reactions reported by Smedley in *J. Chem. Soc.* 87, 1249 (1905). All these reported methods involve use of fluorenone to prepare 9,9-bis(hydroxyphenyl)fluorene.

It would be desirable to have a process for preparation of such bisphenols as 9,9-bis(hydroxyphenyl)fluorene without using fluorenone as a reactant because preparation of fluorenone involves loss of starting materials, additional steps which may be time-consuming, and optionally, use of unpleasant starting materials. For instance, fluorene may be converted to fluorenone by use of sodium dichromate to achieve about a 60–70 percent yield. A higher yield is reported by Alneri, et al. Tetrahedron Letters, 24, 2117 (1977), but requires 24 hours. A multiphase system involving an organic phase, an aqueous sodium hydroxide phase and a catalyst of elemental carbon and phase transfer catalyst has also been reported in U.S. Pat. No. 4,297,514 (K. Ma) but has the disadvantage of handling a solid and separating a product from it. In each instance the fluorenone product must be isolated and purified before subsequent reaction. It would be desirable to avoid such extra steps.

SUMMARY OF THE INVENTION

The invention is a process for chlorinating at least one compound having acidic protons and a molecular structure which can delocalize the electron density of the conjugate base comprising contacting said compound with at least one perchloroalkane and aqueous base in the presence of a phase transfer catalyst which is a tetraalkylammonium hydroxide.

The process of the invention is particularly useful for chlorinating compounds having acidic protons and a molecular structure which can delocalize the electron density of the conjugate base compounds such as fluorene, which with conventional chlorination procedures will not replace the acidic protons with chlorine.

When used to prepare such dichloro compounds as 9,9-dichlorofluorene, the process leads to an especially preferred process of alkylating phenols, phenolics, aromatic amines, alkylaromatics and other such aromatic compounds to give valuable polymers, oligomers, intermediates and monomers, particularly, bis(hydroxyphenyl)fluorene.

DETAILED DESCRIPTION OF THE INVENTION

The process of the invention is useful for chlorinating compounds which have acidic protons and a molecular structure which can delocalize the electron density of the conjugate base. It has been stated by Reutov et. al. (O. A. Reutov, I. P. Beletskaya and K. P. Butin, CH-ACIDS, Pergamon Press. New York, N.Y., 1978.) that "almost any organic compound can ionize in solution to give carbanions, that is, negatively charged species whose charge is totally or more often partially localized on one of the carbon atoms." When certain substituents are part of the hydrocarbon structure and are bonded to a saturated carbon atom which also bears hydrogen atoms, these hydrogen atoms are relatively acidic. Examples of such substituents are unsaturated functional groups such as vinyl, nitro, carbonyl, cyano, sulfone, or phenyl groups. The inductive electron withdrawing ability and the ability of these substituents to delocalize the negative charge remaining when a proton has been removed are responsible for the acidity of these carbon-hydrogen bonds. These compounds are often referred to as active methylene (—$CH_2$—) or active methine (—CH—) compounds. Active methylene compounds are preferred for use in the practice of the invention; more preferred are compounds having an active methylene group adjacent to at least one vinyl, nitro, carbonyl, cyano, sulfone, cyclopentadiene, or phenyl group, most preferably adjacent to at least two such groups which may be the same or a combination thereof. Exemplary of such compounds are fluorene, ring-substituted fluorenes, indene, xanthene, anthrone, phenalene, chromene, acetone, acetophenone, deoxybenzoin, phenylacetonitrile, cyclopentadiene, dihydroanthracene, 1-phenyl-2-propanone, alkylpyridines, alkylpyrazines, alkylquinolines, alkylisoquinolines, alkylquinoxalines, alkylquinazolines, alkylcinnolines and the like. The process of the invention is particularly useful for compounds for which the replacement of the acidic protons with chlorine is not easy under conventional chlorination conditions including fluorene, indene, xanthene, anthrone and the like, preferably fluorene and its derivatives which are ring-substituted, most preferably fluorene. Such target compounds are unsubstituted or inertly substituted, that is having substituents which do not undesirably interfere with the chlorination or subsequent reactions. Such substituents include alkyl, halo, nitro, cyano, carboxyl, thio, sulfoxide, sulfone, carbonyl, ether, and aryl groups, as well as other substituents not having a hydroxyl, primary or secondary amino, or mercapto group. Preferably the compounds have from about 5 to about 30 carbon atoms and more preferably at least one aryl group which is preferably carbocyclic, preferably of from about 6 to about 20 carbon atoms or heterocyclic of from about 5 to about 20 carbon atoms and at least one oxygen, sulfur, nitrogen, selenium, silicon, or other heteroatom.

The target compound is chlorinated by contacting it with a perchloroalkane such as carbon tetrachloride, hexachloroethane, or benzotrichloride and the like as the chlorine source. Carbon tetrachloride is the preferred chlorine source and is used herein to exemplify perchloroalkanes, but not to limit the process thereto. The perchloroalkane is suitably used in any amount which provides sufficient chlorine for the reaction, and may also be present in an amount sufficient to dissolve the compound being chlorinated (target compound). It is, however, unnecessary that there be sufficient perchloroalkane to dissolve the target compound. When the compound to be chlorinated has a low solubility in the perchloroalkane, it is preferable to use a solvent miscible in the perchloroalkane which dissolves significant amounts of the target compound. Preferably the perchloroalkane is used in an amount from about 1:1 to about 100:1 based on the molar concentration of reactant (target compound), more preferably from about 2:1 to about 50:1, most preferably from about 2:1 to about 10:1 based on the molar concentration of the target compound.

When an additional solvent is used, it is preferably one which is miscible with the perchloroalkane and which dissolves the target compound and, conveniently, is not undesirably affected by the reaction conditions. Such solvents include methylene chloride, ethylbenzene, cumene, chlorobenzene, tetrahydrofuran and the like. Such a solvent is conveniently used in an amount sufficient to obtain the maximum concentration of the target compound but not so little that the product would precipitate from the reaction mixture.

The target compound is contacted with the perchloroalkane in the presence of a base strong enough to deprotonate the target compound, that is, capable of forming the conjugate base of the target compound. Such bases include inorganic and organic hydroxides and any other strong bases compatible with water, preferably alkali metal hydroxides or tetraalkylammonium hydroxides more preferably alkali metal hydroxides, most preferably sodium hydroxide. Alkali metal hydroxides are preferred because they have good solubility in water and relatively low equivalent weight. Sodium hydroxide is more preferred because of commercial availability. The base is advantageously in aqueous solution because of ease of removal from product. The solution is suitably of a concentration sufficient to promote the reaction at a desirable rate, preferably from about 10 percent to about 80 percent, more preferably from about 20 percent to about 50 percent, most preferably from about 30 percent to about 40 weight percent base in water. Sodium hydroxide solutions of 40 percent and above often result in emulsions which are difficult to handle. The aqueous solution of base and perchloroalkane are suitably present in any ratio sufficient to promote the reaction at a desirable rate. A desirable rate is generally one sufficient to complete the reaction in the desired time, but insufficient to cause excessive or uncontrollable exothermic heating of the reaction mixture.

Contrary to the teachings of Reeves et Israel J. Chem. 26, 225, (1985) wherein a large excess of base was used with a tetrabutylammonium bromide phase transfer catalyst, in the process of the invention it is surprisingly observed that much less than an equivalent of base is needed. The preferable amount of base as a function of the concentration of the target compound is 0.001 to 1000, more preferably from about 0.01 to about 100, most preferably from about 0.1 to about 10 molar ratio. Less than a stoichiometric amount of base is preferred because it leaves more room in the reactor to make product and there is less base to dispose of after the reaction.

Because the target compound is not sufficiently soluble in the aqueous base, a phase transfer catalyst is used. Surprisingly good yields and low reaction times are noted when the phase transfer catalyst is a tetraalkylammonium hydroxide such as tetrabutylammonium hydroxide, tetramethylammonium hydroxide, tetraethylammonium hydroxide, tetrapropylammonium hydroxide, benzyltrimethylammonium hydroxide, tributylmethylammonium hydroxide and the like, or a tetraalkylphosphonium hydroxide such as tetrabutylphosphonium hydroxide, tetrapropylphosphonium hydroxide, (together tetraalkylonium hydroxide), preferably the phase transfer catalyst is a tetraalkylammonium hydroxide wherein all alkyl groups have from about 1 to about 20 carbon atoms and are nonaromatic, more preferably the tetraalkylammonium hydroxide is tetrabutylammonium hydroxide or tributylmethylammonium hydroxide, most preferably tetra-n-butylammonium hydroxide because this catalyst brings the reaction to completion in the shortest time with the least amount of catalyst relative to the target compound.

The phase transfer catalyst is suitably present in any amount sufficient to give a desired rate of reaction, advantageously at least about 0.000 mole ratio, preferably from about 0.0001 to about 1, more preferably from about 0.001 to about 0.1, most preferably from about 0.001 to about 0.05 molar ratio based on the number of moles of the target compound because this amount gives an acceptable rate of reaction and using more generally costs more and makes purification of the product more difficult. While the hydroxide phase transfer catalyst is optionally admixed with other phase transfer catalysts, e.g. the halide salts, the phase transfer catalyst is preferably present in the hydroxide salt form in at least the concentrations noted.

The concentrations indicated are preferably that of the phase transfer catalyst in the form of the hydroxide salt. Although theoretically phase transfer catalysts having other anions could convert into the hydroxide when hydroxide ions are present, such a conversion is not generally observed. Quaternary ammonium salts are true ionic species in aqueous media and behave as salts much like the alkali halides. Thus, in an aqueous solution, the quaternary ammonium salts are present as ion pairs and freely undergo ion exchange with other ions in solution. When a quaternary ammonium salt is employed as a catalyst in a two phase reaction system, the concentration of that salt in the separate phases is dependent on the relative solubility of the salt in each phase. When phase transfer catalysts having two or more types of anion are present, the relative concentrations of quaternary ammonium salts may be calculated from the extraction constants for the salts and solvents of interest. Extraction constants ($E_{QX}$) for systems $Q^+_{aq} +X^-_{aq} = QX_{org}$ (concentrations of quaternary ions in aqueous phase+anion in aqueous phase is in equilibrium with quaternary salt in organic phase) are defined by $$E_{QX}=(QX)_{org}/(Q^+)_{aq}(X^-)_{aq}$$

where $Q^+$ is the quaternary ammonium cation, $X^-$ is the anion, and QX is the quaternary ammonium salt of interest. When two ions are present, the extraction equilibrium K defined as $$K=E_{QY}/E_{QX}=(QY)_{org}(X^-)_{aq}/(QX)_{org}(Y^-)_{aq}$$

(where $X^-$ and $Y^-$ are different anions) defines the relative amounts of the quaternary ammonium salts that will be present in the organic phase. DehmLow (E. V. DehmLow, M. Slopianka, and J. Heider, Tetrahedron Lett., 1977, 2361.) has measured this value by equilibrating tetra n-butylammonium chloride with 50 percent NaOH solution and found that of the tetra n-butylammonium ion present in the organic phase only 4.2 percent was present as the hydroxide form, the remainder being present as the chloride. The extraction constants for tetra n-butylammonium chloride ($E_{QX}$=1.00), tetra n-butylammonium bromide ($E_{QX}$=48.5) and tetra n-butylammonium hydroxide ($E_{QX}$=0.01) are reported by Gustavi (K. Gustavi and G. Schill, Acta Pharm. Suec., 3 259, (1966) in A. Brandstrom, Principles of phase transfer catalysis by quaternary ammonium salts, in "Advances in Physical Organic Chemistry," Vol 15, V. Gold, Ed., Academic Prss, London and New York, 10977, page 281). Using these values we may calculate that when tetra n-butylammonium bromide is equilibrated with 50 percent NaOH only 0.086 mole percent of the tetra n-butylammonium ion present in the organic phase is present as the hydroxide form, the remainder being present as the bromide.

Thus, since the hydroxide form of the phase transfer catalyst is observed to be, very surprisingly, more effective than the bromide form, it is evident that the hydroxide form is preferably present in a concentration greater than about 0.09 mole percent, more preferably greater than about 0.1 mole percent, most preferably greater than about 1 mole percent of the total phase transfer catalyst. Even more preferably at least about 10 percent of the phase transfer catalyst present is in the hydroxide salt form. Also, the chlorination process of the invention preferably takes place in the presence of insufficient bromide or other ion that would extract the tetraalkylammonium ion into the organic phase to reduce the concentration thereof in the aqueous phase below that concentration achieved by the hydroxide salt at the preferred concentrations. Most preferably, the reaction takes place in the substantial absence of bromide ion—that is in the absence of added bromide anion.

Conveniently, the compound to be chlorinated is dissolved in the perchloroalkane, to which are added the aqueous base and phase transfer catalyst either sequentially in either order, simultaneously but separately or in admixture to form a reaction mixture. This order is convenient because it is observed that the solution of the compound in perchloroalkane is conveniently purged, e.g. with an inert gas such as nitrogen, helium, argon, neon, or hydrogen to remove oxygen to avoid production of an oxidized target compound as a by-product. Alternatively, the reagents are suitably mixed in any order such that all reactants are present at one time. The reaction mixture is preferably agitated by any means effective to maximize the surface area of the immiscible phases so that the reactants in each phase are repeatedly brought together.

When ketone products are not desired it is often preferable to exclude oxygen from the reaction. Oxygen is suitably excluded by any means within the skill in the art such as by maintaining a nitrogen blanket over the reaction mixture, such as by nitrogen sparging. Other inert gasses or the vapors of highly volatile organic compounds may be employed.

Any reaction conditions under which the chlorination takes place are suitable, but preferred temperatures are from about 0° C. to about 100° C., more preferably from about 15° C. to about 80° C., most preferably from about 25° C. to about 40° C. because at these temperatures the reaction proceeds rapidly and there is little degradation of the catalyst. Any effective pressure is suitable, at or near atmospheric pressure is generally convenient. High pressure is not harmful. Lower pressures are limited by the vapor pressures (boiling points) of the solvents employed.

Good mixing is important for rapid reaction. For instance at a mole ratio of sodium hydroxide to fluorene of 10:1; mole ratio of tetrabutylammonium hydroxide to fluorene of 0.02:1.0; mole ratio of carbon tetrachloride to fluorene of 2:1 and 25 weight percent fluorene in methylene chloride at 30° C. for the indicated times, the following table indicates the importance of stirring on yield of 9,9-dichlorofluorene (9,9-DCF).

| TIME (minutes) | at 500 RPM percent 9,9-DCF corresponding to 0.8 W/L | at 1500 RPM percent 9,9-DCF corresponding to 19.7 W/L | at 3000 RPM percent 9,9-DCF corresponding to 106 W/L |
| --- | --- | --- | --- |
| 0 | 0 | 0 | 0 |
| 1 | 73.1093 | 84.8193 | 95.7622 |
| 2 | 80.2118 | 89.1515 | 96.7862 |
| 3 | 84.6704 | 91.7289 | 97.1994 |

-continued

| TIME (minutes) | at 500 RPM percent 9,9-DCF corresponding to 0.8 W/L | at 1500 RPM percent 9,9-DCF corresponding to 19.7 W/L | at 3000 RPM percent 9,9-DCF corresponding to 106 W/L |
| --- | --- | --- | --- |
| 4 | 89.3134 | 93.3434 | 98.1167 |
| 5 | 91.7465 | 93.5317 | 98.1575 |
| 10 | 94.8384 | 95.7186 | 98.9512 |
| 15 | 96.2824 | 97.4078 | 99.053 |
| 20 | 96.9075 | 97.4977 | 99.0207 |
| 30 | 97.177 | 97.4588 | 99.086 |
| 60 | 98.1961 | 98.47 | 99.3304 |
| 120 | 96.3133 | 97.3576 | 99.0197 |

Thus, for relatively shorter reaction times, relatively faster mixing is preferred. While mixing is difficult to quantify, in a situation with relatively constant viscosities, power per unit volume (watts per liter) is indicative of the amount of mixing. These values were obtained using a Lightnin™ LabMaster II™ Model TSM2010 Mixer commercially available from Mixing Equipment Company, Avon Division, a unit of General Signal which directly measures the watts input into the mixer. Thus, in the practice of the invention, mixing preferably involves use of at least about 0.8 W/L, more preferably at least about 15.0 W/L, most preferably at least about 100 W/L. Such mixing is suitably accomplished by any means within the skill in the art such as by rotary, static (e.g. recirculating, e.g. by pump) or other mixing.

The reaction is preferably carried out using non-metallic vessels and equipment, that is not having exposed metals, because metals such as iron (including steel, even stainless steels such as those designated as 304 or 316 stainless steel), nickel and titanium are observed to inhibit the reaction. The term non-metallic vessels and equipment is used to include vessels and equipment lined with non-metallic materials such as polymers (including plastics, resins and glass). Thus the reaction preferably occurs in the substantial absence of such metals, that is in the absence of sufficient metal to undesirably inhibit the reaction, more preferably in the absence of other than incidentally present (not deliberately added) metals particularly iron, including 304 stainless steel and 316 stainless steel. These metals are believed to inhibit the tetraalkylammonium hydroxides; thus use of additional tetraalkylammonium hydroxide to replace that which is inhibited permits reaction in the presence of metals.

The product can be isolated by means within the skill in the art, preferably by washing the solution with water to remove catalyst, then evaporating the solvent. Products are usually solids and are optionally purified by crystallization.

The reaction is allowed to go to a predetermined degree of completeness, advantageously to completion as determined by cessation of an increase in concentration of product. At temperatures such as about 30° C., completion is observed after about 1 minute to 3 hours depending on catalyst concentration, caustic concentration, and degree of agitation or mixing.

The catalyst (tetraalkylonium hydroxide) and/or the base (inorganic or organic hydroxides) are, optionally, conveniently recycled to prepare gem dichloro compounds through many reaction cycles with no loss in efficacy. The catalyst is easily recovered from the reaction mixture after completion of the reaction by means known to those skilled in the art, such as extraction with water or other immiscible solvent having good solubility for the tetraalkylonium hydroxide, or alternatively by contacting the reaction solution with an acidic ion exchange resin to retain the catalyst as a salt followed by regeneration of the tetraalkylonium hydroxide by contacting the ion exchange resin with an aqueous hydroxide solution. In either case, the catalyst is conveniently isolated by evaporative removal of the solvent or is simply used without isolation if the concentration and the solvent are appropriate for the desired reaction. Reuse of the base is, for instance, accomplished by phase separation of the organic and aqueous phases after completion of the reaction and admixing or contacting fresh organic reaction mixture with the separated aqueous phase. Catalyst, either fresh or recovered, is then supplied and the reaction repeated. Recycle of catalyst and/or base is a major advantage since it reduces the amount of raw materials needed with corresponding reduction of waste to dispose.

When the chlorination process is used to prepare a dichloro compound, preferably 9,9-dichloro-fluorene, dichlorocyclopentadiene, 1,1-dichloroindene, 9,9-dichloroxanthene, 9,9-dichlorothioxanthene, 1,1-dichlorophenalene, 11,11-dichloro-4,5-methylenephenanthrene, p-biphenylyldiphenyldichloromethane, dichlorophenylpropanone, 4,4-dichloro-4,H-chromene, dichlorodeoxybenzoin, dichloroacetophenone, 1,1-dichloroacetone, more preferably 9,9-dichlorofluorene, it is particularly beneficial to react the dichloro compound with a compound having an activated (electron rich) aromatic structure such as a phenol, an aniline, a phenolic, a polyphenolic, an aromatic hydrocarbon such as toluene, anisole, indene, xylene, ethylbenzene, dimethoxybenzene, thiophene, furan, pyrole and the like. The term "dichloro compound" includes compounds having at least one gem-dichloro group (two chlorine atoms on the same carbon) including such compounds as tetrachloroanthracene, as produced by chlorination of dihydroanthracene by practice of the invention.

Dichloro compounds such as 9,9-dichlorofluorene, are reactive in alkylation and can be reacted with aromatic compounds to form e.g. 9,9-diarylfluorenes where aryl substituents replace the chlorine atoms of the dichloro group(s). For simplicity, this aspect of the invention is explained in terms of aromatic derivatives of 9,9-dichlorofluorene, but the invention is not limited thereto and is applicable to all dichloro compounds such as are prepared by the process of the invention. Such compounds can be reacted with any aromatic compound which is reactive toward electrophilic aromatic substitution. These include aromatic compounds substituted with activating groups such as alkoxy, alkyl, hydroxy, or amino groups, as well as aromatic compounds substituted with weakly deactivating groups such as halo, ester, ketone, anhydride, or haloalkoxy groups. Reaction of e.g. 9,9-dichlorofluorene with two equivalents of an activated aromatic substrate can form e.g. a 9,9-diarylfluorene compound. For less activated aromatic substrates it is advantageous to use an excess of the aromatic substrate to produce e.g. a 9,9-diarylfluorene compound. Reaction of dichloro compounds such as 9,9-dichlorofluorene with an approximately equimolar amount of a suitably reactive aromatic substrate produces a polymer. To avoid crosslinking through the aromatic portion of a dichloro compound during the alkylation reaction with a dichloro compound to form monomers, oligomers, and polymers, the aromatic substrate should be more activated to alkylation than the dichloro compound itself. Activated aromatic compounds such as those having ether, hydroxyl or amine substituents can react with such compounds as 9,9-dichlorofluorene without the addition of a Lewis acid catalyst. Although the reaction proceeds without added catalyst, less activated aromatic compounds react more efficiently with the addition of an acid catalyst. Suitable protic and Lewis acid catalysts include, but are not limited to, HCl, $AlCl_3$, $FeCl_3$, $SbCl_5$, H₂SO₄, CH₃SO₃H, EtAlCl₂(ethyl aluminum chloride), BF₃, ZnCl₂, GaCl₃; calcined sulfate salts of Fe, Zn, Co, Mn, and Cu; AlCl₃—CH₃NO₂, SnCl₄, TiCl₄, the metal alkanoates commonly known as paint driers such as iron naphthenate, zinc octoate, cobalt naphthenate, tin octoate, and similar such compounds, and polymeric acid catalysts including ion exchange resins, fluorine-containing sulfonic acid catalysts, acidic clays, zeolites, oxides of aluminum and silica. Lewis acid catalysts are optionally generated in-situ by reaction of active metals such as Al, Zn, Fe with HCl either added or formed as a byproduct of the reaction. Examples of aromatic compounds which can be alkylated with such compounds as 9,9-dichlorofluorene include toluene, xylene, 2-aminophenol, ethylbenzene, indene, benzocyclobutane, anisole, phenol, aniline, 2-bromotetrafluoroethoxybenzene, bromobenzene, chlorobenzene, fluorobenzene, phenyl acetate, acetophenone and the like. Examples of aromatic compounds which can be alkylated with such compounds as 9,9-dichlorofluorene to form polymers include phenyl ether, phenyl carbonate, dimethoxybenzene, diphenyl amine, benzene, xylene, durene, poly(phenylene ethers) and substituted derivatives thereof where the substituents do not deactivate the aromatic compounds such that no polymer is formed. The dichloro and aromatic compounds are suitably unsubstituted or inertly substituted, that is having substituents which do not undesirably interfere with the alkylation. Such substituents include alkyl, alkoxy, halo, nitro, cyano, carboxyl, thio, sulfoxide, sulfone, carbonyl, ether, aryl, ester, anhydride, and ketone groups.

Any compound reactive with the dichloro compound is suitably reacted therewith. Exemplary phenolic compounds include any phenolic or thiophenolic compound which reacts with the dichloro compound, including alkylphenols, cresol, chlorophenol, isopropylphenol, propylphenol, 2,6-dimethylphenol, naphthol, xylenol, dichlorophenol, phenylphenol, resorcinol, catechol, hydroquinone, aminophenols, hydroxybiphenyl, hydroxyacetophenone, allylphenols, dialkylphenols, thiophenols, nitrophenols, halophenols, naphthols, hydroxybiphenyls, nonylphenol and ethylphenol, preferably o-, m- and p-cresols, 2,6-dimethylphenol, o- and m-chlorophenols, 2-naphthol, 1-naphthol, 3,4-xylenol or 3,4-dimethylphenol, 2-methylthiophenol, 2-nitrophenol, 3-nitrophenol, 4-nitrophenol, 2-aminophenol, 3-aminophenol, 4-aminophenol, 2,6-dimethylphenol, 2,6-dichlorophenol, 3,5-dichlorophenol, 3,4-dimethylphenol, o-, m- and p-cresols and pyrogallol, more preferably phenol, aminophenol, methoxyphenol, o-hydroxyacetophenone, 2,6-dimethylphenol, 2,6-dichlorophenol, 3,5-dichlorophenol, and pyrogallol, most preferably (unsubstituted) phenol, 2,6-dimethylphenol, 2,6-dichlorophenol, 3,5-dichlorophenol, 3,4-dimethylphenol, o-, m- and p-cresols and pyrogallol. Alkyl and dialkyl phenols preferably have alkyl groups of from about 1 to about 50 carbon atoms, more preferably from 1 to about 10 carbon atoms, and are suitably cyclic, straight chain or branched.

Exemplary aniline compounds include unsubstituted aniline, N-alkylanilines, alkylanilines, dialkylanilines, o-, m-, p-phenylenediamine, chloroanilines, phenylanilines, N-methylaniline, methylaniline, 2,6-dimethylaniline, 2-chloroaniline, toluenediamine, methylenedianiline, polymeric methylenedianiline, 2,6-dichloroaniline, and ethylaniline.

Exemplary aromatic hydrocarbon compounds include toluene, benzene, ethylbenzene, biphenyl, xylene, trimethylbenzene, durene, napthalene, indene, benzocyclobutane, diethylbenzene, dialkylbenzenes, furans (particularly methyl and chloro substituted) and thiophenes (particularly methyl and chloro substituted).

Exemplary aromatic ether compounds include anisole, methylanisole, phenyl ether, dimethoxybenzene, biphenyl ether, diphenoxybenzene, 4,4'-diphenoxy phenylether and naphthyl ether.

Exemplary halogenated aromatic compounds include chlorobenzene, fluorobenzene, and bromobenzene.

Exemplary aromatic ester compounds include phenyl acetate, phenyl carbonate, methyl benzoate, methylsalicylate, and phenyl benzoate.

Other exemplary aromatic compounds include acetophenone, and phthalic anhydride, as well as heterocyclic compounds including furan, methyl furan, chlorofuran, benzofuran, thiophene, methylthiophene, chlorothiophene, pyrrole, methyl pyrrole, and chloropyrrole.

Derivatives of the listed compounds such as the acetamide or maleimide derivative of aniline or the listed anilines are similarly useful. For instance, the N-phenylmaleimide is useful to prepare bismaleimides which are useful as monomers for certain addition polymers. Similarly, the acetamide derivative of aniline may be used in place of aniline.

Alternatively, the dichloro compounds may be reacted with compounds which have at least two aromatic rings connected by a bond or a bridge of one atom which is optionally substituted, as illustrated by:

aromatic-X-aromatic wherein "aromatic" stands for any aromatic group, including any suitable for use in the aromatic compounds not having a bridge, and X stands for a bond or any bridging group such as —O—, —S—, —CO—, —CH₂—, —NH—, —PR—, —SO₂—, —SO—, —Se—, —SiR₂—, and the like, which are also optionally substituted, e.g. —NR—, —CR₂—, —CHR—, where R is any group, preferably an optionally inertly substituted hydrocarbyl group, more preferably a hydrocarbyl or fluorocarbyl group of from about 1 to about 6 carbon atoms. Such compounds are advantageously substituted such that dialkylation of the dichloro compounds onto these compounds occurs with the formation of a 5- or 6-membered ring, preferably between aromatic rings, more preferably including the bridging group X and the carbon of a gem-dichloro group in the dichloro compound. For this type of cyclization, it is preferred that substitution on the aromatic compound be such that alkylation ortho to the —X— group is favored. For example, where the presence of —X— would favor alkylation ortho or para to —X—, such as wherein —X— is —O—, —S—, or a bond, it is advantageous for the compound to be substituted in the para position with an activating or deactivating group such that alkylation ortho to —X— becomes the favored reaction. Compounds of this type include 4,4'-thiodiphenol, 4,4'-oxydianiline, 4,4'-thiodianiline, and 4,4'-diphenic acid. It is also advantageous to not only be substituted in the para position, but also to have additional substitutents which further activate the position ortho to —X— to alkylation. Compounds of this type include 3,3',4,4'-tetraaminobiphenyl, 3,3'-dimethoxybenzidine, 3,3'-dihydroxy-4,4'-diaminobiphenyl, and 3,3'-dimethylbenzidine. Where such additional substituents do not activate the position ortho to —X— to alkylation, it can be advantageous to have additional substituents such that alternate positions which would have been active toward alkylation are already substituted and therefore, blocked. Compounds of this type include tetrabromobisphenol A. When the nature of the —X— group is such that alkylation ortho to this group is not favored, such as wherein —X— is —CO—, —SO$_2$—, or —SO—, it is advantageous that the compound be substituted meta to —X— with groups which will activate the position ortho to —X— to alkylation. Compounds of this type include 3,3'-diamino-4,4'-diphenylsulfone, 3,3'-dimaleimido-4,4'-diphenylsulfone, and 3,3'-diaminobenzophenone. Exemplary compounds for the formation of such cyclized products include bismaleimide (1,1'(methylenedi-4,1-phenylene)bismaleimide), 4,4'-diphenic acid, biphenyl tetracarboxylic dianhydride, 4,4'-diamino-3,3'-dihydroxybiphenyl, 3,3'-diamino-diphenylsulfone, 3,3'-dimaleimidodiphenylsulfone, 3,3'-4,4'-tetraaminobiphenyl, 3,3'-diaminobenzophenone, bis(4-fluorophenyl)methane, o-tolidine (3,3'-dimethylbenzidine), hisphenol F, tetramethylbisphenol F, 4,4'-thiodiphenol, 4,4'-oxydiphenol, 4,4'-oxydianiline, 4,4'-oxydiacetanilide (e.g. made by reaction of 4,4'-oxydianiline with acetyl chloride), 4,4'-thiodianiline, 4,4'-thiodiacetanilide (e.g. made by reaction of 4,4'-thiodianiline with acetyl chloride), 3,3'-dimethoxybenzidine, 3,3'-dimethylbiphenyl, and 1,1-bis(3,4-dimethylphenyl)ethane. While cyclization advantageously takes place under the reaction conditions useful for alkylation (reaction of dichloro and aromatic compounds), especially when those conditions are acidic; additional acid is useful when the conditions are less acidic, particularly when the aromatic compound is amine-substituted, e.g. an aniline, and when little or no acid catalyst is used.

The dichloro compounds are also reactive with aromatic compounds substituted such that cyclization to form 5- or 6-membered rings occurs during or subsequent to the alkylation reaction. Exemplary compounds for the formation of such cyclized products include resorcinol, hydroquinone, hisphenol A, biphenol, m- and p-phenylenediamine, p-aminophenol, m-aminophenol and mixtures thereof.

In the discussions of aromatic compounds, most illustrations of aromatic rings have been phenyl groups, however, while phenyl rings are preferred for their wide availability, the rings are suitably fused and/or heterocyclic rings such as furans, thiophenes and pyrrole. The aromatic compound preferably has from 5 to about 20 ring atoms, at least 4 of which are preferably carbon atoms, with heteroatoms in the ring(s) suitably any atom which forms a ring compound with carbon, but preferably selected from O, S, N, and phosphorus, all optionally substituted such as SO$_2$, NH, —PR$_2$ or —P(=O)R$_2$, where R is alkyl or alkoxy preferably of from about 1 to 10 carbons. More preferably the ring has from about 6 to about 13 ring atoms, all most preferably carbon.

As one example of the use of multicyclic aromatic compounds, the dichloro compounds are optionally reacted with polyphenolic material such as novolac resins produced as reaction products of such aromatic hydroxyl compounds as phenol, cresol or xylenol with an aldehyde, preferably formaldehyde, to produce resinous products. The novolacs are advantageously kept at stoichiometric equivalent or excess to the dichloro compounds. These modified polyphenolics are useful as curing agents for polyepoxy compounds, and as starting materials for producing polyepoxies and polycyanates.

To modify the reactivity, processability, or thermal and mechanical properties of the resultant products, dichlorocompounds and aromatic compounds are optionally reacted in suitable ratios to form oligomeric products which are useful for further reaction to form polymeric materials or which are optionally terminated with the same or different aromatic compounds. By increasing the ratio of the dichloro compound to aromatic compound greater than that ratio sufficient to replace both chlorine atoms by aromatic compound, oligomers terminated with end groups containing a resulting mono-chloro compound are produced. For example, reaction of 9,9-dichlorofluorene with phenyl ether in a molar ratio of about 3:2 will produce a mixture of oligomers wherein the terminal fluorene groups retain a 9-chloro functionality. Reacting this oligomeric mixture with an excess of phenol will produce a phenolic oligomer suitable for conversion into a polymer. Reacting the 9-chloro terminated oligomeric mixture with, for instance, a mixture of 9,9-dichlorofluorene and phenyl carbonate in about 1:1:1 molar ratio will produce a block copolymer. Reacting the 9-chloro terminated oligomeric mixture with, for instance, benzocyclobutane, will produce a benzocyclobutanyl-capped oligomer suitable for use in forming benzocyclobutanyl polymers. Similarly, these oligomeric compounds can be further reacted by processes taught herein or within the skill in the art. Exemplary of aromatic compounds that can be used to form oligomers when reacted with dichloro compounds are phenyl ether, anisole, dimethoxybenzene, xylene, mesitylene, methylanisole, phenol, cresol, bisphenol A, bisphenol F, biphenol, phenol-aldehyde novolac resins, bisphenol S, biphenyl, phenylphenol, phenylthioether, and the like, and mixtures thereof.

Combinations of aromatic compounds are useful to react with the dichloro compounds. Advantageously, when combinations of aromatic compounds are reacted with the dichloro compounds, they have similar reactivity with the dichloro compounds such that the products of such reactions have approximately equal amounts of each aromatic compound distributed therein. For instance, benzocyclobutane and N-phenylmaleimide are reacted with 9,9-dichlorofluorene to produce mixtures of 9-(benzocyclobutanyl)-9-(maleimidophenyl)fluorene, 9,9-bis(benzocyclobutanyl)fluorene, and 9,9-bis(4-maleimidophenyl)fluorene. Similarly, o-allylphenol and N-phenylmaleimide are reactive with 9,9-dichlorofluorene to produce an analogous mixture of compounds. Advantageously, when the aromatic compounds have dissimilar reactivities or when certain predetermined products or mixtures are desired, product mixture is controlled by stoichiometry of the mixture of aromatic compounds reacted or by use of sequential reactions. Sequential reactions are particularly exemplified by the reaction of one mole of an aniline with a dichloro compound according to the practice of the invention, which reaction produces a monoalkylation product; the monoalkylation product is then reacted with another mole of aromatic compound, e.g. a phenol. Alternatively, the monochloro compound may be isolated and used in a separate application. For example, reaction of 9,9-dichloroxanthene with one equivalent of benzene produces 9-chloro-9-phenylxanthene, a deoxynucleoside 5'-0-protecting reagent. Control by stoichiometry of reactants is exemplified by reaction of a dichloro compound with a mixture of one mole each of two aromatic compounds (illustratively referred to as A and B) to produce a product mixture of alkylation products with two moles of B (BB), with two moles of A (AA), and with a mole of each (AB). When even distribution of products is desired and the reactivities are dissimilar, those skilled in the art realize that use of an excess of the less reactive aromatic compound (the amount of excess determined by the difference in reactivities) will result in a more evenly distributed product mixture than will use of equimolar quantities of the aromatic compounds. Other predetermined proportions of products are obtained by use of proportions of the aromatic compounds determined by their relative reactivities and the predetermined desired proportions.

The reaction between the dichloro compound and the aromatic compound (together, reactants) is suitably conducted with any reactant ratios and under any conditions in which the compounds react, but, when monomeric products are desired, preferably the aromatic is present in an amount sufficient to consume the chloro compound but insufficient to make isolation of the product difficult, preferably from about 100:1 to about 1:100, more preferably from about 50:1 to about most preferably from about 4:, to about 1:1 based on equivalents of chlorine to be replaced (aromatic compound equivalents to chlorine equivalents). When the aromatic compound is an aniline, the most preferred ratio is from about 4:1 to about 2:1 moles of the aniline to moles of dichloro compound. When preparation of a polymer or oligomer is desired, reactant ratios are suitably any sufficient to produce polymer or oligomer but insufficient to produce mostly monomeric compound, preferably from about 0.5:1 to about 1:0.5 more preferably from about 0.9:1 to about 1:0.9 based on equivalents of chlorine to be replaced.

Reaction of dichlorofluorene with benzocyclobutane illustrates the utility of the oligomer forming reaction. 9,9-bis(benzocyclobutanyl)fluorene is formed when a mole of dichlorofluorene is reacted with a large excess (ten to thirty moles) of benzocyclobutane under conditions of mild temperature, e.g. room temperature to about 50°, and addition of the dichlorofluorene to an excess of benzocyclobutane. However, when a mole of dichlorofluorene is reacted with less than ten moles of benzocyclobutane, oligomers are formed which generally have n benzocyclobutane groups and (n-1) fluorene groups, resulting from disubstitution of some of the benzocyclobutane groups with dichlorofluorene, where n is at least 2. The oligomers are useful because they form low melting thermosettable compositions which can be cured thermally with no added catalyst and without the evolution of volatiles. A useful variation of this chemistry is the use of an aromatic compound more reactive than benzocyclobutane, preferably an aryl ether such as anisole, diphenoxy phenyl ether, diphenoxy benzene or diphenyl ether along with the benzocyclobutane to alkylate the dichtorofluorene. Thermosetting resins are formed having internal oligomeric sections which are made up of alternating fluorene and aryl ether moieties and are terminated with benzocyclobutane groups or fluorene-benzocyclobutane oligomeric sections. Oligomers having benzocyclobutane, more reactive aromatic compounds, especially polyphenylene ethers, and dichlorofluorene are useful to crosslink epoxy resins. Although the reactive oligomers containing benzocyclobutane rings are described in terms of fluorene derivatives, which are particularly useful for this purpose, the fluorene is merely illustrative of the gem-dichloro compounds previously described, all of which, particularly the polycyclic dicloro compounds, are useful in the process.

This invention differs from current benzocyclobutane polymer (BCB) chemistry as illustrated by U.S. Pat. No. 4,540,763 (Kirchoff et al.). BCB chemistry typically requires the use of bromo-benzocyclobutane as a starting material. Bromination of benzocyclobutane hydrocarbon adds an additional step and produces waste products, thus adding a significant cost to the final resin products. Alternatively, the benzocyclobutane hydrocarbon is used in the acylation of the hydrocarbon with a diacid chloride and an equivalent amount of Lewis acid (to the carbonyls, i.e. to acylate a diacid chloride onto benzocyclobutane requires two moles of Lewis acid for every mole of diacid chloride). The present invention differs from that technology in that only catalytic amounts of Lewis acid are used. Use of little Lewis acid simplifies a synthesis process, not only in the amount of waste generated, but also in the ease of separating the catalyst from the desired product.

When analogous oligomeric mixtures are made from the reaction of a dichloro compound, e.g. dichlorofluorene, with alkylaromatics such as toluene, cumen, xylenes, trimethylbenzene, and the like, the oligomeric mixtures are advantageously oxidized by means within the skill in the art to form polyacids and/or polyanhydrides, useful as monomers for instance to make polyglycol esters useful in polyurethanes.

The reactants are suitably used neat or in solution. When used neat, they are preferably liquids, but may alternatively be used in the solid state by means within the skill in the art such as by mixing or grinding the finely divided solids together in a mill or blender under conditions of high shear. Especially when at least one reactant is solid, a solvent is used, suitable solvents include any solvent for at least one of the reactants, preferably for both, and preferably which does not interfere with the reaction or react with either reactant. Preferred solvents include carbon tetrachloride, chloroform, methylene chloride, ethylene dichloride, trichloroethane, tetrachloroethane (any common chlorinated solvents); aromatic hydrocarbons such as benzene, toluene, ethylbenzene; chlorinated aliphatic compounds; aromatic ethers such as phenyl ether; ethers, ketones, esters, amides, sulfoxides, alcohols, alkanoic acids, halogenated aromatics such as chlorobenzene; tetrahydrofuran; acetic acid and nitriles such as acetonitrile, more preferably dichloromethane, carbon tetrachloride, ethylbenzene, toluene or chlorobenzene.

While suitable reaction conditions include any effective conditions, including temperatures of from subambient to several hundreds of degrees centigrade; preferably temperatures used are less than the boiling points of any reactants under the pressure used. Conveniently, when a solvent is not used, the temperature is sufficient to allow at least one reactant to be liquid. Preferred temperatures range from about −30° C. to about 100° C., more preferably from about 0° C. to about 70° C., most preferably from about 20° C. to about 50° C., particularly when a catalyst is used. When no additional catalyst is used, higher temperatures are generally advantageous. For instance, when no catalyst is used and the aromatic compound is an aniline, temperatures are preferably at least about 40° C., more preferably from about 40° C. to about 200° C., most preferably from about 50° C. to about 150° C. At these temperatures, reaction times are preferably at least about 1 hour, more preferably from about 1 to about 8 hours, most preferably from about 3 to about 7 hours. The pressure is not critical, but conveniently ranges from about 0.1 to several hundreds of atmospheres, more preferably from about 1 to about 50, most preferably from about 1 to about 200 atmospheres (100–20,000 kPa). It is generally desirable to run the reaction with less active compounds at the higher limits of the indicated ranges and the more active compounds at the lower limits of the indicated temperature and pressure ranges.

By controlling reaction temperatures, one can achieve substitution of one chlorine on the dichloro compound with an aromatic compound, leaving a remaining chlorine atom unreacted. For instance, when an excess of aniline is reacted with 9,9-dichlorofluorene at a temperature of about 60° C., an exotherm to about 110° C. is observed, which exotherm corresponds to formation of 9-aminophenyl-9-chlorofluorene. Continued heating at about 130° C. results in further alkylation to form 9,9-bis(aminophenyl)fluorene. When isolation of a mono-substituted compound is desired, the reaction is advantageously run in a non-solvent for a compound or adduct that binds hydrochloric acid produced in the mono substitution. For instance, when the aromatic compound is an aniline, the hydrochloride of the aniline forms; therefore, when the reaction is run in a non-solvent for the aniline hydrochloride, such as monochlorobenzene, dichlorobenzene, toluene, or xylene, the aniline hydrochloride precipitates, removing the hydrochloride which is believed to otherwise act as catalyst for the substitution of the remaining chlorine atom by a second molecule of aromatic compound. It is observed that after precipitation of the aniline hydrochloride, even additional heating does not result in formation of the disubstituted product, e.g. bis(aminophenyl)fluorene. The mono-substituted product thus obtained is useful for instance in reactions with aromatic compounds different from that used to prepare the mono-substituted product; for instance, 9-aminophenyl-9-chlorofluorene is reactive with aromatic compounds such as phenol under conditions discussed herein to produce disubstituted compounds such as 9-aminophenyl-9-(hydroxyphenyl)fluorene.

Although the reaction is autocatalytic because the HCl produced by the reaction is an effective catalyst, any acid catalyst, advantageously HCl or any other hydrogen halide, may be added to the aromatic compound as a catalyst for the reaction, particularly as a catalyst for the thermodynamically favored (generally the para, para substituted aromatic) product. Use of a catalyst permits reaction at temperatures lower than would be effective without a catalyst. The temperatures depend on the reactivity of the aromatic compound with the dichloro compound; for instance in reactions with 9,9-dichlorofluorene, without catalyst, phenol will react at about 0° C., aniline at 25° C. and toluene at about 70° C. The catalyst is preferably added before the addition of the dichloro compound to the aromatic compound because addition of the acid catalyst is more useful before the concentration of HCl produced in the reaction has reached a desired catalytic concentration. For instance, while the reaction of aniline with 9,9-dichlorofluorene at temperatures of more than about 20° C. does not require a catalyst, reaction of 9,9-dichlorofluorene with phenol preferably involves a catalyst to proceed at atmospheric pressure and temperatures of less than about −20° C. That catalyst, however, is preferably a protic acid such as a hydrogen halide (preferably used at pressures greater than atmospheric pressure), or methanesulfonic (MSA), sulfuric, toluenesulfonic, hydroxybenzenesulfonic, trifluoromethanesulfonic, acetic, haloacetic, oxalic acid or mixtures thereof, at atmospheric pressure. By way of contrast, reaction of 9,9-dichlorofluorene with hydrocarbons such as benzocyclobutane and toluene preferably involve a Lewis acid catalyst, preferably $AlCl_3$—$CH_3NO_2$, $SbCl_5$, $FeCl_3$, $ZnCl_2$, and more preferably ferric chloride or $SbCl_5$ in the case of benzocyclobutane to allow reaction to occur at less than about 60° C. Anisole reacts with 9,9-dichloro without catalysts at 80° C., and at room temperature to 40° C. with Lewis Acid catalysts such as $ZnCl_2$ or $FeCl_3$. Where, such as in the case of benzocyclobutane, the HCl produced can have a detrimental effect on the organic substrate, it is advantageous to sparge the HCl from the reaction with an inert gas such as nitrogen. When a hydrogen halide is used, it is advantageous to conduct the reaction under a pressure greater than atmospheric by the use of a hydrogen halide, e.g. hydrogen chloride. The pressure of the hydrogen halide may vary from about 1 to about 1000 atmospheres, preferably from about 10 to about 100 atmospheres.

Catalyst concentration affects the distribution of isomers in a product. For instance, in the case of the reaction of phenol with 9,9-dichlorofluorene, methanesulfonic acid (MSA) is an effective catalyst in concentrations of from about 1 percent to about 1000 percent based on the dichloro compound, but at the lower concentrations of from about 1 percent to about 10 percent, the ortho, para- isomer of bis(hydroxyphenyl)fluorene is formed along with the para, para- isomer. When the para-, para- isomer is preferred, the concentration of MSA is preferably from about 15 percent to 1000 percent, more preferably from about 20 percent to about 100 percent based on the dichloro compound. In general, at atmospheric pressure and at temperatures of from about 0° to about 170°, and for a time sufficient to isomerize the product to the thermodynamically favored isomer, increasing the concentration of MSA from about 1 percent to about 1000 percent, increases the concentration of the para-, para- isomer relative to the concentration of ortho-, para- isomer of bis(hydroxyphenyl)fluorene. Similar effects are found in other alkylations of the dichloro compounds. Similarly, when HCl or other hydrogen halide is the catalyst, increasing the pressure of the hydrogen halide from atmospheric pressure to about 100 atmospheres (10,000 kPa) also increases the concentration of the thermodynamically favored para, para-, isomer relative to the concentration of the ortho, para-, isomer of bis(hydroxyphenyl)fluorene. Acid can be used to isomerize less thermodynamically favored products to more thermodynamically favored products during and/or after reaction of the dichloro compounds with the aromatic compounds.

Methods of recovering product alkylated aromatic compounds from reaction mixtures are within the skill in the art. Conveniently, when there is little excess aromatic compound remaining in the reaction mixture, a crystallization solvent is added to the reaction mixture to precipitate product. Advantageously, when excess reactant aromatic compound is present, it is removed by means within the skill in the art before a crystallization solvent is added to precipitate the product. Convenient crystallization solvents include hydrocarbons such as pentane and hexane, aromatic hydrocarbons such as toluene and ethylbenzene; chlorinated aliphatics such as chloroform and carbon tetrachloride; ketones such as acetone and methyl ethyl ketone; and esters such as diethyl carbonate and mixtures of these solvents. In the case of amine derivatives such as 9,9-bis(aminophenyl)fluorene, basic solutions such as, advantageously aqueous, solutions of sodium hydroxide or sodium bicarbonates are useful crystallization solvents. Crystallization is advantageously enhanced by cooling of the reaction mixture before or after addition of the crystallization solvent. Cooling alone is sometimes sufficient to cause precipitation of product without addition of crystallization solvent. Before crystallization, hydrogen chloride, if present, is optionally, but preferably, removed by means within the skill in the art such as distillation. The precipitate in each case is advantageously washed with a non-solvent therefor to remove remaining reactants.

Avoiding addition of water or other material which would result in an additional waste to dispose is advantageous; therefore, methods of recovery which avoid using water to wash or otherwise isolate the product are of particular interest. Such methods include use of hydrogen halides, preferably hydrogen chloride, as acid because it can be removed by such means as vaporization at reasonable temperatures without a water wash which is generally advantageous to remove such acids as sulfuric acid and methanesulfonic acids. Solid acids such as clay and polymer acids are also removable without water washing. When approximately stoichiometric amounts of dichloro compound and aromatic compound are reacted, especially to produce 9,9-bisarylfluorenes such as 9,9-bis(hydroxyphenyl)fluorene at temperatures less than about 40° C. in such solvents as methylene chloride, ethylbenzene, toluene, cumene, carbon tetrachloride, hexane, heptane, or other alkanes, the product precipitates without addition of other materials; thus, these conditions, too, are preferred for avoiding unnecessary waste disposal. The precipitate is recovered by means such as filtration and, optionally, recrystallization. Use of carbon tetrachloride as solvent in the reaction of an excess of such aromatic compounds as phenol with such dichloro compounds as 9,9-dichlorofluorene results in a precipitate identified as an 1:1:1 adduct of product: carbon tetrachloride: aromatic compound which can be recovered by such means as filtration, washing with a non-solvent for the product such as methylene chloride, a ketone or other chlorinated solvents to remove the aromatic compound and carbon tetrachloride or heating to remove carbon tetrachloride with washing to remove aromatic compound and, optionally, recrystallization from a suitable solvent, such as those suitable for washing.

In the alkylation of the dichloro compounds, isomers of the alkylation product are formed. For instance the reaction of phenol with 9,9-dichlorofluorene, both ortho, para- and para, para-isomers of the bis(hydroxyphenyl)fluorene are formed. Analogous ortho, para- and para, para- isomers of alkylation products of other dichloro compounds are also formed. Conversion of ortho, para- isomers to para, para- isomers is advantageous and can be accomplished by increased time in contact with an acid such as the acid catalyst which is optionally used in the reaction of the dichloro compound with the aromatic compound, an ion exchange resin, or a hydrogen halide, e.g. liquified HCl, preferably an acid which is easily removed such as a polymeric acid (including ion exchange resin) or an acid that is easily vaporized such as a hydrogen halide or the acid present in the reaction mixture, removal of which would not add additional steps to the overall process. Frequently, there are also products representing the addition products of the dichloro compound with one mole of the aromatic compound and with product diaryl compound. Such byproducts are conveniently reacted with additional dichloro compound and/or additional aromatic compound to convert them into the desired product. Conveniently, these conversions of byproducts including ortho, para- product is accomplished by removal of the desired (para, para-) product and addition of additional aromatic compound and/or dichloro compound to the remaining reaction mixture; preferably the aromatic compound is added to the mixture including the byproducts, the mixture is heated (with additional acid if needed) to rearrange the isomers, then additional dichloro compound is used. In a continuous process or a process having sequential batches, advantageously a recycle process is used in which additional aromatic compound, additional dichloro compound and, optionally, additional acid are added to an initial reaction mixture, then desired product is removed as additional byproduct mixture is added.

The process of the invention facilitates the preparation of such compounds as 9,9-bis(4-hydroxyphenyl)xanthene, 9,9-bis(3,4-diaminophenyl)fluorene, 9,9-bis(4-carboxyphenyl)fluorene, 9,9-bis(4-acetylphenyl)fluorene, 9,9,10,10-tetrakis(4-hydroxyphenyl)-9,10-dihydroanthracene, 10,10-bis(4-hydroxyphenyl)anthrone, 9,9-bis(methylphenyl)fluorene, 9,9-bis(4-methoxyphenyl)fluorene, 1,1'-(9H-fluoren-9-ylidenedi-4,1-phenylene)bismaleimide, spiro[9H-fluorene-9,9'-[9H]-xanthene]-3',6'-diol, spiro[9H-fluorene-9,9'-[9H]-xanthene]-2',7'-diol, and the like previously available from ketones.

The process of the invention also facilitates preparing a number of novel compounds including 9,9-bis(4-ethylphenyl)fluorene, 9,9-bis(4-ethenylphenyl)fluorene, 9,9-bis(4-ethynylphenyl)fluorene, 9,9-bis(3,4-dimethylphenyl)fluorene, 9,9-bis(2,3-dimethylphenyl)fluorene, 9-(3,4-dimethylphenyl)-9-(2,3-dimethylphenyl)fluorene, 9,9-bis(3-amino-4-hydroxyphenyl)fluorene, 9,9-bis(4-amino-3-hydroxyphenyl)fluorene, 9-(3-amino-4-hydroxyphenyl)-9-(4-amino-3-hydroxyphenyl)fluorene, 9,9-bis(1,3-isobenzofurandion-4-yl)fluorene, 9,9-bis(1,3-isobenzofurandion-5-yl)fluorene, 9-(1,3-isobenzofurandion-4-yl)-9-(1,3-isobenzofurandion-5-yl)fluorene, 9,9-bis(benzocyclobutanyl)fluorene, 9,9-bis(4-halophenyl)fluorene, 9,9-bis(dicarboxyphenyl)fluorene, 9,9-bis(dihydroxyphenyl)fluorene, 9,9-bis(dimethylphenyl)fluorene, spiro[9H-fluorene-9,9'-[9H]carbazine]-3',6'-diol, spiro[9H-fluorene-9,9'-[9H]carbazine]-3',6'-diamine, spiro[9H-fluorene-9,9'-[9H]carbazine]-2',7'diamine, spiro[9H-fluorene-9,9'-[9H]xanthene]-2',7'-dicarboxylic acid, spiro[9H-fluorene-9,9'-[9H]xanthene]-3',6'-diamine, 2',7'-diacetylspiro[9H-fluorene-9,9'-[9H]xanthene], spiro[9H-fluorene-9,13'-[13H]-6-oxapentacene]-2',10'-diol, spiro[9H-fluorene-9,13'-[13H]-6-oxapentacene]-3',9'-diol, 3',6'-diaminospiro[9H-fluorene-9,9'-thiaxanthene]-10',10'-dioxide, spiro[9H-fluorene-9,9'[9H,10H]-dihydroanthracene]-2',7'-bismaleimide, 10-oxo-spiro[9H-fluorene-9,9'[9H,10H]-dihydroanthracene]-3',6'-diamine, 2',7'-dimethylspiro[9H-fluorene-9,9'-[9H]xanthene], 2',7'-dicyanospiro[9H-fluorene-9,9'-[9H]xanthene], 2',7'-diformylspiro[9H-fluorene-9,9'-[9H]xanthene], 2,7-diamino-3,6-dihydroxy-9,9'-spirobifluorene, 2,7-diamino-3,6-dimethyl-9,9'-spirobifluorene, spiro[9H-fluorene-9,9'[9H,10H]-dihydroanthracene]-2',7'-diamine, 2',3',6',7'-tetraaminospiro[9H-fluorene-9,9'-thiaxanthene]-10',10'-dioxide, spiro[9H-fluorene-9,9'[9H]xanthene]-2',3',6,7'-tetraamine, 2,3,6,7-tetraamino-9,9'-spirobifluorene, 2,7-diamino-9,9'-spirobifluorene-3,6-dithiol, 2,7-bis(1-methyl-1-(4-hydroxyphenyl)ethyl)spiro[xanthene-9,9'-fluorene], 2,7-bis(4-hydroxyphenyl)spiro[xanthene-9,9'-fluorene], 1,3,6,8,10,10-hexamethylspiro[dihydroanthracene-9,9'-fluorene]-2,7-diol, 1,3,6,8-tetrabromo-10,10-dimethylspiro[dihydroanthracene-9,9'-fluorene]-2,7-diol, 1,3,6,8-tetramethylspiro[dihydroanthracene-9,9'-fluorene]-2,7-diol, spiro[9H-fluorene-9,9'-[9H]xanthene]-3',6'-dicarboxylic acid, spiro[9H-fluorene-9,9'-[9H]xanthene]-2',7'-dicarbonyl chloride, spiro[9H-fluorene-9,9'-[9H]xanthene]-3',6'-dicarbonyl chloride, 3',6'-dimethyl-spiro[9H-fluorene-9,9'-[9H]xanthene], 2',7'-diisopropylspiro[9H-fluorene-9,9'-[9H]xanthene], 3',6'-diisopropylspiro[9H-fluorene-9,9'-[9H]xanthene], 2',3',6',7'-tetramethylspiro[9H-fluorene-9,9'-[9H]xanthene], spiro[9H-fluorene-9,9'-[9H]xanthene]-2',3',6',7'-tetracarboxylic acid, spiro[9H-fluorene-9,9'-[9H]xanthene]-2',3',6',7'-tetracarboxylic acid dianydride, e.g. prepared from 9,9-dichlorofluorene reacted with ethylbenzene; styrene; ethylbenzene; 1,2-dimethylbenzene; o-amino phenol, phthalic anhydride, benzocyclobutane, halobenzene (e.g. bromo-, chloro-, iodo- or fluoro-benzene), phthalic acid, dimethylbenzene, catechol, hydroquinone, 3-aminophenol, p-phenylenediamine, m-phenylenediamine, 4-hydroxybenzoic acid, 4-aminophenol, 4-hydroxyacetophenone, naphthalenediol, 2,7-naphthalenediol, 3,3'-diaminodiphenylsulfone, 1,1'-(methylenedi-4,1-phenylene)bismaleimide, 4,4'-diaminobenzophenone, p-cresol, 4-cyanophenol, 4-hydroxybenzaldehyde, 4,4'-diamino-3,3'-dihydroxybiphenyl, o-tolidine, methylenedianiline, 3,3',4,4'-tetraaminodiphenylsulfone, 3,3',4,4'-tetraaminodiphenylether or 3,4-diaminophenol, 3,3',4,4'-tetraaminobiphenyl, 4,4'-diaminobiphenyl-3,3'-dithiol, bisphenol A, biphenol, tetramethyl bisphenol A, tetrabromobisphenol A, tetramethyl bisphenol F, m- and p-cresol, 3,4-dimethyl phenol. 3- and 4-isopropylphenol, respectively. The compounds are useful as monomers in polymers such as polyesters, polycarbonates, epoxy resins, polyamides, polyimides, polybenzoxazoles, polybenzimidazoles, benzocyclobutane polymers, polybenzthiazoles, polyquinoxalines, and as intermediates for preparing monomers. For instance 9,9-bis(4-ethylphenyl)fluorene is useful to prepare 9,9-bis(4-ethenylphenyl)fluorene by reactions analogous to those used to prepare styrene from ethylbenzene, and 9,9-bis(3,4-dimethylphenyl)fluorene is useful to prepare 9,9-bis(1,3-isobenzofurandion-5-yl)fluorene by reactions analogous to those used to prepare phthalic anhydride from xylene. The polymers are prepared by means within the skill in the art. Additionally, the process of the invention wherein monosubstitution of the gem-dichloro compound is achieved is particularly useful to prepare such aniline derivatives as 9-(4-aminophenyl)-9-chlorofluorene, and the alkyl derivatives thereof including the N-alkyl and ring-substituted derivatives such as 9-(4-(N-methylaminophenyl))-9-chlorofluorene, 9-(4-amino-3-methylphenyl)-9-chlorofluorene, 9-(4-amino-3-ethylphenyl)-9-chlorofluorene, 9-(4-amino-3-chlorophenyl)-9-chlorofluorene, 9-(4-amino-4-methylphenyl)-9-chlorofluorene, 9-(4-amino-2-ethylphenyl)-9-chlorofluorene, 9-(4-amino-2-chlorophenyl)-9-chlorofluorene, and mixtures thereof. Such compounds are particularly useful for further alkylation to form compounds having mixed aromatic substituents replacing the chlorines of the dichloro compounds.

While products of the invention are generally useful in forming condensation polymers when they contain at least two reactive functional groups (e.g. hydroxyl, amine, sulfide, acid, acid halide, anhydride, or aldehyde groups) or in addition polymers when they contain at least one carbon to carbon unsaturation, they can also be converted to additional compounds having useful functional groups. For instance phenol- and/or amine- containing products, especially phenol- and/or amine- containing derivatives of 9,9-dichlorofluorene are useful for conversion into epoxy resins by means within the skill in the art such as those described in "Epoxy Resins, Chemistry and Technology" C. A. May, Yoshio Tanaka, Marcel Dekker, Inc., NY (1973) and "Handbook of Epoxy Resins" H. Lee, K. Neville, McGraw Hill, N.Y. (1967). Similarly, the phenol-containing products are useful for conversion into cyanate resins by means within the skill in the art such as those disclosed in Angew. Chem. Int'l Ed. 6, 206 (1967), E. Grigat and R. Pütter; U.S. Pat. No. 4,110,364 (1978) M. Gaku, K. Suzuki, K. Nahamichi; U.S. Pat. No. 4,060,541 (1977) Rudolf Sunderman; U.S. Pat. No. 3,994,949 (1976) Karl-Heinrich Meyer, Claus Burkhardt, Ludwig Bottenbruch; U.S. Pat. No. 4,046,796 (1977) (Gunther Rottloff, Rudolf Sundermann, Ernest Grigat, Rolf Pütter); and U.S. Pat. No. 4,028,393 (1977) (Gunther Rottloff, Rudolf Sundermann, Ernest Grigat, Rolf Pütter). The phenol-containing compounds are also useful as agents for partial advancement or hardening of epoxide-containing compounds. The amino-containing products are also useful as curing agents for epoxide-containing compounds.

The following examples are given to illustrate, but not limit the invention. In the examples, all parts, ratios and percentages are by weight unless specified otherwise. Examples of the invention (Ex.) are designated numerically, while comparative samples (C.S.) are designated alphabetically.

EXAMPLE 1

Preparation of 9,9-Dichlorofluorene from Fluorene

The reactor is a 500 mL 3-neck round bottomed flask equipped with a magnetic stir bar, nitrogen purge and thermometer. The reactor is flushed with nitrogen, and a solution of fluorene (6.00 g, 0.036 mole) and carbon tetrachloride ($CCl_4$) (669.48 g, 4.35 mole, 420 mL) is charged to the reactor followed by NaOH (50 percent solution in water, 6.00 g, 0.075 mole, 4.0 mL, 3.00 g dry weight). The stirrer is started and the speed adjusted to 500 RPM (revolutions per minute). The mixture is stirred with a subsurface nitrogen sparge. The temperature of the reaction solution is 28° C. The catalyst, tetrabutylammonium hydroxide (40 percent solution in water, 1.9 g, 0.0029 mole, 1.9 mL), is added at once.

The reaction is followed by gas chromatography (GC) on a GC (commercially available from Varian Associates under the trade designation Varian 3700 equipped with a 15 meter by 0.53 mm Megabore (Trademark of J&W Scientific) capillary column coated with a 1 micron film of polydimethylsiloxane commercially available from J&W Scientific under the trade designation DB-1 as the stationary phase and a flame ionization detector (FID)(commercially available from Varian Associates under the trade designation Varian 3700) with conditions of 250° C. at the injector, 350° C. at the detector, 130° C. of the column for the first minute then programmed to rise 3° per minute to 160° C. and to hold that temperature for one minute. The reaction mixture is sampled after 20 minutes and analyzed by GC which shows that the reaction mixture contains 18.46 percent fluorene, 81.54 percent 9,9-dichlorofluorene. No other product is evident. The reaction is sampled and analyzed periodically over the next three hours. After stirring overnight no fluorene remains according to the GC analysis; results are shown in Table 1. Stirring is stopped, the phases are allowed to separate, and the aqueous phase is removed from the reactor. The reaction mixture is filtered through alumina and the $CCl_4$ is removed on a rotary evaporator leaving 8.40 g of light yellow crystals, 99 percent of theory. NMR and GC-mass spectral analysis of this material shows it to be identical with that of a known sample of 9,9-dichlorofluorene.

TABLE 1

CHLORINATION OF FLUORENE BY CARBON TETRACHLORIDE via PHASE TRANSFER CATALYSIS

| TIME Minutes | FLU- ORENE Percent | 9,9- DICHLORO- FLUORENE percent | 2,7- DICHLORO- FLUORENE percent | $ClC_{14}$* percent |
|---|---|---|---|---|
| 0.00 | 100.00 | 0.00 | 0.00 | 0.00 |
| 20.00 | 18.46 | 81.54 | 0.00 | 0.00 |
| 40.00 | 13.92 | 86.09 | 0.00 | 0.00 |
| 60.00 | 10.51 | 89.50 | 0.00 | 0.00 |
| 120.00 | 8.62 | 91.39 | 0.00 | 0.00 |
| 180.00 | 4.56 | 95.46 | 0.00 | 0.00 |

*Cl—C14 is a chloro-fourteen carbon compound found in the product of photochlorination of fluorene.

The data in Table 1 shows that chlorination of fluorene by the process of the invention leads to 9,9-dichlorofluorene and not 2,7-dichlorofluorene or the $C_1$-$C_{14}$ compounds detected in photochlorination of fluorene. The product is also observed to have a mass spectrum corresponding to that of a known sample of 9,9-dichlorofluorene with base peak at 199 atomic mass units (AMU) and parent ion at 234 AMU. The nuclear magnetic resonance (NMR) spectrum of the product is also consistent with that of a known sample of 9,9-dichlorofluorene with peaks at 7.81–7.84 ppm (2H), 7.59–7.63 ppm (2H), 7.37–7.47 ppm (4H) relative to TMS (tetramethylsilane) in $CDCl_3$ solution. The $C^{13}$ NMR shows peaks at 146.69, 136.48, 130.67, 129.041, 124.60, 120.14, 82.93 relative to tetramethylsilane.

COMPARATIVE SAMPLE A:

Reaction Carried Out as Described by Reeves et al.

The reactor is a 500 mL 3-neck round-bottomed flask equipped with a magnetic stir bar, nitrogen purge and thermometer. The reactor is flushed with nitrogen, and a solution of fluorene (6.00 g, 0.036 mole) and carbon tetrachloride (669.48 g, 4.35 mole, 420 mL) is charged to the reactor followed by NaOH (50 percent solution in water, 6.00 g, 0.075 mole, 4.0 mL, 3.00 g dry weight). The stirrer is started and the speed adjusted to 500 rpm. The mixture is stirred with a subsurface nitrogen sparge. The temperature of the reaction solution is 28° C. The catalyst, tetrabutylammonium bromide (0.93 g, 0.0029 mole), is added at once.

The reaction followed by gas chromatography (GC) as in Example 1. The reaction mixture is sampled after 40 minutes and analysis shows 98.17 percent fluorene, 1.83 percent 9,9-dichlorofluorene. The reaction is sampled and analyzed periodically over the next thirty six hours. After three hours, only 10.29 percent of the fluorene has been converted to 9,9-dichlorofluorene compared to 95.46 percent in the previous example (Example 1). At thirty six hours, 15.16 percent of the fluorene remains unconverted in the reaction mixture. This data shows that tetrabutylammonium bromide is not as effective a catalyst for this reaction as is tetrabutylammonium hydroxide.

EXAMPLE 2

Use of Less than an Equivalent of Sodium Hydroxide in the Chlorination of Fluorene The reactor is a 12 inch (30.48 cm) section of 2 inch (5.08 cm) inside diameter pipe made from fluorocarbon polymer commercially available from E.I. du Pont de Nemours & Co. under the trade designation Teflon PFA which is swaged to a 0.5 inch (1.27 cm) tee at the lower and upper ends. To the bottom-most leg of the lower tee is joined a stopcock which can be used to drain the reactor's contents. To the other leg of this tee is attached the suction inlet of a pump (a magnetically driven centrifugal pump commercially available from March Manufacturing Inc. under the trade designation March model, MDX-MT3 rated at 28.39 liters/minute at zero head). The outlet of the pump is plumbed to a heat exchanger through which the reaction mixture passes and which, in turn, is connected to the top-most leg of the upper tee on the reactor. The other leg on the upper tee is used as a port to charge reactants to and vent purge gas from the reactor. A nitrogen sparge is provided at the inlet of the heat exchanger. This design results in continuously impinging the organic phase at a high velocity into the aqueous phase, achieving good interfacial contact. A thermocouple is provided at the discharge port of the pump for measuring the temperature of the reaction.

The reactor is flushed with nitrogen. Then a solution of fluorene (16.62 g, 0.1000 mole) and carbon tetrachloride (149.60 g, 0.9726 mole, 93.85 mL) is charged to the reactor followed by NaOH (30 percent solution in water, 1.33 g, 0.010 mole, 1.00 mL, 0.40 g dry weight). The pump is started and the temperature adjusted to 30° C. The catalyst, tetrabutylammonium hydroxide (40 percent solution in water, 1.28 g, 0.0020 mole, 1.28 mL), is added at once. The mixture is circulated with a subsurface nitrogen sparge. The temperature of the reaction solution is 30° C.

The reaction is followed by gas chromatography (GC) by the procedure of Example 1. Analysis after 60 minutes shows 15.46 percent fluorene, 84.09 percent 9,9-dichlorofluorene.

This result shows that less than an equivalent of sodium hydroxide is effective in achieving chlorination by the process of the invention.

EXAMPLE 3

Use of Benzyltrimethylammonium Hydroxide as Catalyst in the Chlorination of Fluorene The reactor described in Example 2 is flushed with nitrogen, and a solution of fluorene (49.87 g, 0.3000 mole) and carbon tetrachloride (448.79 g, 2.9177 mole, 281.55 mL) is charged to the reactor followed by NaOH (30 percent solution in water, 4.00 g, 0.030 mole, 3.00 mL, 1.20 g dry weight). The pump is started and the temperature adjusted to 30° C. The catalyst, benzyltrimethylammonium hydroxide (40 percent solution in water, 2.82 g, 0.0060 mole, 2.66 mL) is added at once. The mixture is circulated with a subsurface nitrogen sparge. The temperature of the reaction solution is 30° C. The reaction is followed by gas chromatography as in Example 1. After 60 minutes analysis shows 84.34 percent fluorene, 14.20 percent 9,9-dichlorofluorene.

This example shows that benzyltrimethyl ammonium hydroxide is an effective catalyst for this reaction.

EXAMPLE 4

Use of a Ten Percent Concentration of Sodium Hydroxide in Chlorination of Fluorene The reactor is a 1000 mL cylinder 4 inches in diameter (100 mm) by 5.5 inches high (140 mm) equipped with a 2 inch (50 mm) diameter turbine impeller driven by a vertical shaft. Stirring rate is measured by a tachometer. Temperature is controlled by a 10 foot (3.048 m) by 0.25 inch (0.635 cm) external diameter coil immersed in the reaction medium through which coolant is pumped maintained at a constant temperature by a circulating refrigerated/heated bath.

The temperature is measured by a thermocouple inside a thermowell which runs the entire depth of the reactor. The reactor is also equipped with a nitrogen inlet which is used to maintain a nitrogen atmosphere above the reaction solution. The entire apparatus is constructed of fluorocarbon resin commercially available from E.I. du Pont de Nemours & Co. under the trade designation Teflon PFA.

The reactor is flushed with nitrogen. Then a solution of fluorene (14.96 g, 0.090 mole) and carbon tetrachloride (134.64 g, 0.8753 mole, 84.47 mL) is charged to the reactor followed by NaOH (10 percent solution in water, 359.99 g, 0.90 mole, 324.32 mL, 36.00 g dry weight). The stirrer is started and the speed adjusted to 3000 rpm. The coolant is admitted to the coils, and the temperature of the reaction solution is adjusted to 30° C. The catalyst, tetrabutylammonium hydroxide (40 percent solution in water, 1.14 g, 0.0018 mole, 1.16 mL), is added at once. The reaction mixture is sampled after 1 minute and analyzed by GC according to the method described in Example 1; it shows 94.89 percent fluorene, 4.50 percent 9,9-dichlorofluorene and 0.25 percent 9-fluorenone. After 15 minutes, analysis shows 94.26 percent fluorene, 4.56 percent 9,9-dichlorofluorene and 0.30 percent 9-fluorenone. After an additional three hours, analysis shows 88.78 percent fluorene, 8.52 percent 9,9-dichlorofluorene and 0.76 percent 9-fluorenone.

This example shows that even 10 percent sodium hydroxide is effective in this reaction.

EXAMPLE 5

Use of Twenty Percent Sodium Hydroxide in the Chlorination of Fluorene

The reactor described in Example 4 is flushed with nitrogen. A solution of fluorene (25.56 g, 0.1538 mole) and carbon tetrachloride (230.08 g, 1.4958 mole, 144.34 mL) is charged to the reactor followed by NaOH (20 percent solution in water, 307.59 g, 1.5380 mole, 252.13 mL, 61.52 g dry weight). The stirrer is started, and the speed adjusted to 3000 rpm. The coolant is admitted to the coils and the temperature of the reaction solution is adjusted to 30° C. The catalyst, tetrabutylammonium hydroxide (40 percent solution in water, 1.97 g, 0.0031 mole, 1.98 mL) is added at once. After 1 minute, analysis by the procedure of Example 1 shows 39.65 percent fluorene, 60.04 percent 9,9-dichlorofluorene, and 0.32 percent 9-fluorenone. After 15 minutes, analysis shows 1.44 percent fluorene, 98.21 percent 9,9-dichlorofluorene and 0.34 percent 9-fluorenone. After a three hour reaction time analysis shows 0.97 percent fluorene, 98.66 percent 9,9-dichlorofluorene and 0.37 percent 9-fluorenone. This result indicates that twenty percent aqueous sodium hydroxide is effective.

EXAMPLE 6

Use of Thirty Percent Sodium Hydroxide in the Chlorination of Fluorene

The procedure of Example 5 is repeated except that a solution of fluorene (33.24 g, 0.200 mole) and carbon tetrachloride (299.20 g, 1.94 mole, 187.20 mL) is charged to the reactor followed by NaOH (30 percent solution in water, 266.66 g, 2.00 mole, 200.50 mL, 80.00 g dry weight) and the catalyst is tetrabutylammonium hydroxide (40 percent solution in water, 2.54 g, 0.0040 mole, 2.57 mL). After 1 minute, analysis shows the reaction mixture contains 18.14 percent fluorene, 81.34 percent 9,9-dichlorofluorene, and 0.51 percent 9-fluorenone. After 15 minutes, analysis shows 1.41 percent fluorene, 98.39 percent 9,9-dichlorofluorene and 0.21 percent 9-fluorenone. After an additional one hour, 45 minutes, analysis shows 0.52 percent fluorene, 98.66 percent 9,9-dichlorofluorene and 0.56 percent 9-fluorenone.

This example shows that 30 percent sodium hydroxide is effective in the process of the invention.

EXAMPLE 7

Use of 40 percent Sodium Hydroxide in Chlorination of Fluorene

The procedure of Example 5 is repeated except that a solution of fluorene (33.24 g, 0.200 mole) and carbon tetrachloride (299.20 g, 1.94 mole, 187.20 mL) is charged to the reactor followed by NaOH (40 percent solution in water, 203.64 g, 2.00 mole, 139.86 mL, 80.00 g dry weight) and the catalyst is tetrabutylammonium hydroxide (40 percent solution in water, 2.54 g, 0.0040 mole, 2.57 mL). After 1 minute, analysis shows that the reaction mixture now contains 17.22 percent fluorene, 81.50 percent 9,9-dichlorofluorene, and 1.10 percent 9-fluorenone. After 15 minutes, analysis shows 0.95 percent fluorene, 98.69 percent 9,9-dichlorofluorene and 0.35 percent 9-fluorenone. After an additional one hour, 45 minutes, analysis shows 0.01 percent fluorene, 99.07 percent 9,9-dichlorofluorene and 0.92 percent 9-fluorenone.

This example shows that 40 percent sodium hydroxide is effective in this reaction.

EXAMPLE 8

Use of Fifty Percent Sodium Hydroxide in Chlorination of Fluorene

The procedure of Example 5 is repeated except that a solution of fluorene (33.24 g, 0.200 mole) and carbon tetrachloride (299.20 g, 1.94 mole, 187.20 mL) is charged to the reactor followed by NaOH (50 percent solution in water, 160.00 g, 2.00 mole, 106.67 mL, 80.00 g dry weight) and the catalyst is tetrabutylammonium hydroxide (40 percent solution in water, 2.54 g, 0.0040 mole, 2.57 mL). After 1 minute, analysis shows 6.58 percent fluorene, 92.38 percent 9,9-dichlorofluorene, and 1.03 percent 9-fluorenone. After 15 minutes, analysis shows 0.92 percent fluorene, 98.59 percent 9,9-dichlorofluorene and 0.49 percent 9-fluorenone. After an additional one hour, 45 minutes, analysis shows 0.01 percent fluorene, 92.13 percent 9,9-dichlorofluorene and 7.86 percent 9-fluorenone.

This example shows that 50 percent sodium hydroxide is effective in this reaction.

EXAMPLE 9

Use of Methylene Chloride as an Alternative Solvent with a Stoichiometric amount of $CCl_4$.

The reactor described in Example 4 except with a baffle affixed to the immersed coil is flushed with nitrogen, and a solution of fluorene (47.47 g, 0.2856 mole), methylene chloride (142.40 g, 1.6767 mole, 107.47 mL) and carbon tetrachloride (87.85 g, 0.5711 mole, 55.11 mL) is charged to the reactor followed by NaOH (30 percent solution in water, 380.75 g, 2.8556 mole, 286.28 mL, 114.23 g dry weight). The stirrer is started and the speed adjusted to 3000 rpm. The coolant is admitted to the coils and the temperature of the reaction solution is adjusted to 30° C. The catalyst, tetrabutylammonium hydroxide (40 percent solution in water, 3.633 g, 0.0057 mole, 3.67 mL), is added at once.

Analysis by the procedure of Example 1 at one minute shows 3.35 percent fluorene, 95.76 percent 9,9-dichlorofluorene, and 0.89 percent 9-fluorenone. After 15 minutes, analysis shows 0.78 percent fluorene, 99.05 percent 9,9-dichlorofluorene and 0.17 percent 9-fluorenone. After an additional hour, analysis shows 0.00 percent fluorene, 99.02 percent 9,9-dichlorofluorene and 0.65 percent 9-fluorenone.

This example shows that good results are obtained using alternative solvents such as methylene chloride with only a stoichiometric amount of $CCl_4$.

EXAMPLE 10

Use of Cumene as an Alternative Solvent with a Stoichiometric amount of $CCl_4$.

The procedure of Example 9 is repeated except that a solution of fluorene (33.24 g, 0.200 mole) cumene (188.38 g, 1.5672 mole, 218.04 mL) and carbon tetrachloride (61.53 g, 0.400 mole, 38.60 mL) is charged to the reactor followed by NaOH (50 percent solution in water, 160.0 g, 2.00 mole, 103.9 mL, 80.00 g dry weight); and the catalyst is tetrabutylammonium hydroxide (40 percent solution in water, 2.59 g, 0.004 mole, 2.57 mL). After 1 minute, analysis shows 0.92 percent fluorene, 97.05 percent 9,9-dichlorofluorene, and 2.03 percent 9-fluorenone. After 15 minutes, analysis shows 0.92 percent fluorene, 97.27 percent 9,9-dichlorofluorene and 1.81 percent 9-fluorenone. This data shows that the reaction is essentially complete within one minute under these conditions.

This example shows that good results are obtained using alternative solvents such as cumene with only a stoichiometric amount of $CCl_4$.

EXAMPLE 11

Use of Ethylbenzene as an Alternative Solvent with a Stoichiometric amount of $CCl_4$.

The procedure of Example 9 is repeated except that a solution of fluorene (33.24 g, 0.200 mole), ethylbenzene (188.38 g, 1.7743 mole, 217.28 mL), and carbon tetrachloride (61.53 g, 0.400 mole, 38.60 mL) is charged to the reactor followed by NaOH (50 percent solution in water, 160.0 g, 2.00 mole, 103.9 mL, 80.00 g dry weight); and the catalyst is tetrabutylammonium hydroxide (40 percent solution in water, 2.59 g, 0.004 mole, 2.57 mL). After 1 minute, analysis shows 1.23 percent fluorene, 97.78 percent 9,9-dichlorofluorene, and 0.59 percent 9-fluorenone. After 15 minutes, analysis shows 1.29 percent fluorene, 97.84 percent 9,9-dichlorofluorene and 0.87 percent 9-fluorenone.

This example shows that good results are obtained using alternative solvents such as ethylbenzene with only a stoichiometric amount of $CCl_4$.

EXAMPLE 12

Use of Ethylbenzene as an Alternative Solvent with a Stoichiometric amount of $CCl_4$ with 30 percent Sodium Hydroxide.

The procedure of Example 9 is repeated except that a solution of fluorene (33.24 g, 0.200 mole) ethylbenzene (188.38 g, 1.7 743 mole, 217.28 mL) and carbon tetrachloride (61.53 g, 0.400 mole, 38.60 mL) is charged to the reactor followed by NaOH (30 percent solution in water, 266.67 g, 2.00 mole, 200.5 mL, 80.00 g dry weight); and the catalyst is tetrabutylammonium hydroxide (40 percent solution in water, 2.59 g, 0.004 mole, 2.57 mL). The reaction mixture is sampled after 1 minute and periodically thereafter for the next 30 minutes and analyzed by GC according to the procedure in Example 1. GC analysis at one minute shows 25.65 percent fluorene, 74.35 percent 9,9-dichlorofluorene, and 0.0 percent 9-fluorenone. GC analysis at 15 minutes shows 1.28 percent fluorene, 98.72 percent 9,9-dichlorofluorene, and 0.0 percent 9-fluorenone. GC analysis at 30 minutes shows 1.19 percent fluorene, 98.81 percent 9,9-dichlorofluorene, and 0.0 percent 9-fluorenone.

This result shows that ethylbenzene is effective as a solvent when used with a stoichiometric amount of carbon tetrachloride with 30 percent sodium hydroxide.

EXAMPLE 13

Continuous Preparation of 9,9-dichlorofluorene

This reaction is carried out in a reactor constructed from a 2 inch (5.08 cm) diameter pipe of fluorocarbon resin commercially available from E.I. du Pont de Nemours & Co. under the trade designation Teflon PFA. The reactor contains 6 stirred sections each 1.75 inches (4.45 cm) long separated by horizontal spacers 0.25 inch (0.64 cm) thick which are perforated with eight 0.25 inch (0.64 cm) diameter holes which allow communication between the stages. Centered within each stage is an impeller mounted on a vertical drive shaft constructed of type 316 stainless steel which is 0.375 inches (0.954 cm) tall, by 0.625 inches (1.651 cm) in diameter. An air driven motor drives the drive shaft at a constant speed of 1500 rpm. Each stirred section is approximately 100 mL in volume. The top of the reactor is equipped with ports for the introduction of nitrogen and venting the same such that an inert atmosphere can be maintained during the course of the reaction. The upper-most stirred section or stage contains a port for the introduction of reactants and a thermowell for measuring the temperature of the reactor's contents. There are additional thermowells in stage four from the top and just below the sixth stage. Below the sixth stage from the top there is a twelve inch (30.48 cm) long section which is unstirred and acts as a quiet zone so that the organic and aqueous phases can disengage or phase separate. At the bottom of this reactor is a tee which is connected to a bottom drain on one leg so that the entire contents of the reactor can be removed, and to an overflow tube on the other leg which can be adjusted to control the liquid level in the reactor. The product solution can be continuously drawn off this overflow at a rate equivalent to that which the feed solution is introduced to the first stage of the reactor.

The reactor is purged with nitrogen and then charged with a volume of carbon tetrachloride (400 mL) such that its level just comes to the bottom of the sixth stage. NaOH solution (50 percent by weight, 12.0 moles, 480 g dry weight, 960 g solution weight, 627.45 mL) is then charged to the reactor, which fills all six of the stirred zones. The stirrer is started and its speed is adjusted to 1500 rpm. Fluorene (3.0 moles, 498.66 g) dissolved in carbon tetrachloride (64.84 moles, 9973.20 g, 6256.71 mL) is fed into the first reactor stage through a metering pump at a rate of 19 mL/min. At the same time, tetrabutylammonium hydroxide (0.03 moles, 7.78 g dry weight, 19.46 g as 40 percent aqueous solution) is fed through a separate metering pump into the first reactor stage at a rate of 0.05 mL/min. The product solution is collected at the overflow and analyzed by gas chromatography (GC) on a gas chromatograph commercially available from Varian Associates under the trade designation Varian 3400 GC equipped with a 30 meter by 0.53 mm Megabore (Trademark of J&W Scientific) capillary column coated with a 1 micron film of polytrifluoropropyl-co-dimethylsiloxane commercially available from J&W Scientific under the trade designation DB-210 as the stationary phase and a flame ionization detector (FID) commercially available from Varian Associates under the trade designation Varian 3400.

When fluorene is no longer detected in the effluent stream the product is fed to a wash column which is identical in design to the reactor column. The product solution is fed to the first stirred stage at a rate of 10 mL/min and water is fed at the sixth stirred stage at a rate of 20 mL/min. The organic solution containing the 9,9-dichlorofluorene is collected at the overflow of the wash column and then passed through a column of molecular sieves (4A size, commercially available from Linde Division, Union Carbide Industrial Gasses Inc.) which lowers the water content of the stream as measured by Karl-Fisher titration from 211 ppm to 11.4 ppm. The total product solution collected in this fashion amounts to 12,004 g which is 5.8 weight percent 9,9-dichlorofluorene and 0.05 weight percent fluorenone.

EXAMPLE 14

Large Scale Preparation of Bis(hydroxyphenyl)fluorene

Fluorene (800 lb, 363.63 kg) is dissolved in methylene chloride (2722 lb, 1237.27 kg) in a tank. Then an amount of carbon tetrachloride (CCl$_4$) stoichiometric with the fluorene (1488 lb, 676.36 kg) is added to the resulting solution and mixed thoroughly using a retreated blade agitator. The resulting solution is charged via nitrogen pad into a 1000 gallon (3785 liter) glass lined reactor containing (4963 lb, 256 kg) of a 30 weight percent aqueous solution of sodium hydroxide (NaOH) which is at a temperature of 25° C. The reactor is maintained at a temperature of 25° C. by a flow of a 50 weight percent aqueous solution of ethylene glycol through a steel jacket around the reactor. The reactor is purged with nitrogen. After all of the fluorene solution is charged to the reactor and phase separation occurs (about 10–15 minutes), agitation is begun. Either the aqueous phase or the organic phase can be a continuous phase.

While the temperature is maintained at 25° C. to avoid catalyst deterioration, (12.5 lb, 5.68 kg) of tetra-n-butylammonium hydroxide in aqueous solution (40 percent) is fed to the reactor at a rate of 2.84 kg/hr over a period of 2 hours. Agitation and cooling are continued for one hour, after which agitation is stopped. This is to assure that all of fluorene has been reacted. Reaction of all fluorene is confirmed by GC analysis of the reaction mixture, then the phases are allowed to separate with the organic phase on the bottom of the reactor.

The organic phase is removed at a rate of 1500 lb/hr (681.81 kg/hr) using a centrifugal pump until a small rag layer (where phases are incompletely separated) remains. The organic phase is then washed with 1200 lb/hr (545 kg/hr) portions of water three times with separation of water from the organic phase each time. The organic phase is found to contain about 23 weight percent dichlorofluorene (DCF) in methylene chloride with some CCl$_4$ and chloroform present. That phase is then stored and mixed with subsequent batches of essentially the same composition prepared by the same process. Optionally, the phase could be used immediately to prepare bis-(hydroxyphenyl)fluorene. Repeating the synthesis of DCF offers an opportunity to reuse the NaOH solution. Optionally, the organic phase could be dried using a molecular sieve column to remove water.

After a desired number of batches of DCF are produced, the NaOH solution is pumped from the reactor to the wash section. The sodium hydroxide solution is then treated with sufficient HCl (hydrochloric acid) to neutralize the NaOH.

The reactor and associated piping are flushed with methylene chloride.

Fifty five gal (208 1) of molten phenol at 50° C. is transferred to a reactor using a nitrogen pad. During transfer, the phenol is maintained under a nitrogen atmosphere and weighed such that 232 kg (25 mole percent excess based on 9,9-dichlorofluorene) are transferred into the 1000 gal. (3785 1) reactor which is also purged with nitrogen. Methanesulfonic acid (MSA) (93 lbs, 42.2 kg) is added to the reactor as the catalyst for the phenolation process. For the first batch, the reactor does not contain the recycled material. After the first batch, the reactor content contains the recycled material which consists of chloroform, methylene chloride, p,p-BHPF, o,p-BHPF, 3,2-fluorene-phenol adducts, MSA and phenol. The entire content of the reactor is circulated around the reactor using the pump at the bottom of the reactor and the agitator inside the reactor.

A 1207.27 kg portion of the DCF in methylene chloride is added to the recirculation loop of the reactor containing phenol at a rate of 603.63 kg/hr, over a period of 2 hours while the reactor is maintained at 15° C. by cooling in the jacket of the reactor. The pressure remains atmospheric. Precipitation of product p,p-bis(hydroxyphenyl)fluorene (p,p-BHPF) is noted after about half of the DCF is added.

The addition of DCF is completed after 2 hours, precipitation of product p,p-bis(hydroxyphenyl)fluorene (p,p-BHPF) is noted after about half of the DCF is added, but the contents of the reactor are allowed to digest (remain at the same temperature with stirring) over the period of 1 hour at 40° C. Then the reaction mixture is allowed to cool down to 10° C. over a 1 hour period. HCl produced during the first two hours of the reaction is vented into a scrubber containing 500 l of 15 weight percent aqueous NaOH. Heat is removed from the scrubber using an external heat exchanger to cool the circulated sodium hydroxide. After 95 percent of the HCl is removed by venting it to the scrubber, then sufficient nitrogen is introduced from the bottom of the reactor to remove HCl. When removal of HCl is complete as determined by the pH of the solution not being acidic, the remaining contents of the reactor (hereinafter, reaction mixture) are transferred to a holding tank using a pump. The reaction mixture is a slurry.

After the entire contents of the reactor have been transferred (130 gal, 492.05 l), the slurry of crystalline product in reaction mixture is transferred to a pressure filter unit commercially available from Rosenmund, Inc. where a pressure of 15 psi (103.41 kPa) is applied using nitrogen pressure. The amount transferred is controlled by weighing the slurry feed tank before and after transfer using a commercial weight cell.

During transfer to the filter unit, a drain valve is closed; when transfer is complete and no malfunction of the filter is noted, the valve is opened and a pressure of 35 psig, (241.29 kPa) of nitrogen is applied such that a filtrate containing methylene chloride, excess phenol, carbon tetrachloride, chloroform, p,p-BHPF; o,p-BHPF and phenol-fluorene adducts is collected in a check tank.

The filtrate is transferred from the check tank to a batch distillation unit to remove a mixture of chloroform and methylene chloride, which mixture is suitable for recycle to wash the filter cake. Before the distillation starts, 232.25 kg phenol with 42.27 kg methanesulfonic acid are added to the batch distillation pot. Then the distillation of chloroform and methylene chloride is started. After all of the chloroform and all of the methylene chloride have been removed, the remaining filtrate (about 15 percent by weight) is transferred to a waste storage tank, the rest of the mixture is maintained at a temperature of 70° C. and a pressure of 103.41 kPa under nitrogen for a period of one hour to isomerize the phenol-fluorene adducts and o,p-BHPF to p,p-BHPF.

A filter cake of BHPF forms on the filter and is washed using the recovered methylene chloride/chloroform mixture by closing the drain valve, charging the mixture to the filter apparatus at a rate of 10 gal/min (37.85 1/min) until a total of 100 gal (378.5 1) is charged, opening the valve and applying a pressure of 35 psig (241.29 kPa) of nitrogen. The mixture is pushed through the filter cake and collected then recycled to be used with the isomerization mixture. The recycled methylene chloride (MeCl$_2$)/chloroform solution is sent back to the batch distillation pot. The washing step above is repeated two more times: first with the recycled MeCl$_2$ solution, and then with fresh MeCl$_2$ solution; only a trace of MSA remains in the filter cake.

The wet filter cake is found to contain about 45 weight percent methylene chloride and is suitable for use in a process in which methylene chloride is suitabler or can be washed with water to displace most of the methylene chloride by making a slurry of it with water one or more times. The water preferably contains about 1 percent Na₂CO₃ and is at about 70° C., then the filter cake is preferably washed with pure water at 70° C. to remove all residual MSA in the wet cake. Optionally, and alternatively, the filter cake is dried, first by using 30 psig (207 kPa) steam to strip MeCl₂ from the cake then using a pressure of 35 psi (241.29 kPa) nitrogen at a temperature of at least 50° C. blowing through the filter cake to dry the water from the cake. The pressed pressure filter has a mechanical agitator arm to stir up the cake and break up the clump to aid in the drying process.

The filter cake is optionally slurried back in water solution before the drying step to transfer out of the filter apparatus or is optionally dried and transferred out as a solid.

The BHPF is produced in about 80 percent yield based on DCF and has a melting point of 223°–225° C. and the purity of 99 percent as determined by HPLC analysis when prepared as described, without the isomerization step. With the recycle of the adducts and isomers back to the isomerization steps, the overall yield of the process is 95 percent.

Those skilled in the art will recognize that a number of variations on these processes are within the scope of the invention. For instance, phenol may be added in solution (for instance, in methylene chloride) or as a solid. DCF can be added to phenol or other phenolic solution in the phenolation reaction in the form of a solid. The product p,p-BHPF can be recrystallized in methylene chloride. The chlorination reaction can be carried out in a continuous reactor instead of a batch reactor. The phenolation reaction can be carried out in a continuous reactor. Product BHPF can be recrystallized either in addition to or alternative to filtration; alternatively, the BHPF can be used without drying if used in a system where methylene chloride is an acceptable solvent. Similarly, solid separation of the reaction product slurry is optional and can be accomplished by any means within the skill in the art such as basket centrifuge, solid bowl centrifuge, other forms of solid separation and the like. A filter cake can also be washed in a slurry wash and/or displacement wash using fresh or recycled methylene chloride or other non-solvent; a slurry wash would involve stirring the filter cake with the non-solvent until a slurry is formed, and removal of said non-solvent, for instance by filtration or other solid separation technique.

EXAMPLE 15

Preparation of 9,9-Bis(4-methylphenyl)fluorene; Alkylation of DCF onto Toluene using FeCl₃ as Catalyst Dichlorofluorene (10.0 g, 0.042 mole) (DCF) prepared as in Example 13 and ferric chloride (0.1 g, 0.0006 mole) are weighed into a 50 mL 2-necked flask fitted with a stirbar, nitrogen inlet, and thermometer. Toluene (50 mL) is added and the mixture is stirred and heated with a heating mantle. The mixture rapidly becomes dark red, and begins to evolve HCl. At a temperature of 40° C., the solution vigorously evolves HCl. Analysis by GC (using a gas chromatograph commercially available from Varian Associates under the trade designation Model 3700, with a 30 meter column coated with a 1 micron layer of polydimethylsiloxane commercially available from J&W Scientific under the trade designation DB-1) at this point shows almost all of the DCF has reacted, and several heavy products are formed.

The mixture is then heated at 50° C. for 1 hour, after which, the solution is black in color. Analysis of the mixture by GC shows all the DCF has been reacted. The mixture is worked up by washing with water and then diluting the mixture (solution) with pentane, which causes the precipitation of most of the product as a tan powder. This powder is filtered from the solution. The remaining mother liquor is then evaporated, and the resulting solid is slurried in pentane and filtered. The remaining mother liquor is evaporated to give an oily yellow solid. Weight of precipitated product is: first crop, 6.92 g; second crop, 2.64 g ; total, 9.56 g (65 percent of theoretical); weight of yellow solid, 2.19 (15 percent of theoretical weight).

The H-NMR is consistent with a sample of 9,9-bis(methylphenyl)fluorene (MPF) having peaks relative to tetramethylsilane (TMS) at δ2.1–2.5 (m, 6H, CH₃), 6.6–7.9 (m, 16H). C-13 NMR: δ151.63, 145.41, 143.17, 140.15, 138.44, 136.09, 129.15, 128.89, 128.33, 127.95, 127.79, 127.41, 126.12, 125.42, 120.21, 119.69, 65.42, (p,p isomer, quaternary C) 64.90 (o,p isomer, quaternary C), 21.59 (CH₃), 21.08 (CH₃).

As determined by gas chromatography/mass spectroscopy (GCMS) the product mixture is: 77.3 percent bis(4-methylphenyl)fluorene, 16.4 percent (4-methylphenyl)(2-methylphenyl)fluorene, 6.2 percent bis(2-methylphenyl)fluorene. Primary peaks on GCMS for each compound are: (in atomic mass units, AMU, with percentage of height of base (largest) peak at 100 percent in parenthesis after the AMU) in parenthesis after the AMU: for bis(4-methylphenyl)fluorene: 347(27.3); 346(100.0); 331(24.6); 255(17.3); 239(13.7); 65(14.0); for (4-methylphenyl)-(2-methylphenyl)fluorene: 347(28.2); 346(100.0); 331(16.9); 255(18.5); 253(11.3); 65(12.37); and for bis(2-methylphenyl)fluorene: 347(27.5); 346(100.0); 331(21.5); 255(18.0); 65(14.5).

EXAMPLE 16

Preparation of 9,9-Bis(4-methoxyphenyl)fluorene; Alkylation of DCF onto Anisole using Sulfonic Acid Polymer Catalyst Dichlorofluorene (0.5 g, 0.002 mole) is weighed into a 50 mL 2-necked flask fitted with a stirbar, nitrogen inlet, and septum. Anisole (1.08 g, 0.01 mole) is added, and a GC (using a gas chromatograph commercially available from Varian Associates under the trade designation Model 3700, with a 30 meter column coated with a 1 micron layer of polydimethylsiloxane commercially available from J&W Scientific under the trade designation DB-1) is taken of the resulting mixture as a standard. Activated Dow Fluorinated Sulfonic Acid (DFSA) pellets prepared by the process disclosed in U.S. Pat. No. 4,791,081 and available from The Dow Chemical Company under the trade designation XU 40036.01, heated at 170° C. for 24 hours under vacuum (<10 mm Hg) to activate, then stored under nitrogen, are added to the mixture. Then the mixture is heated in a water bath. At a temperature of 50° C., the pellets begin to turn purple. When the mixture has reached 60° C., the solution has taken on a purple cast. The mixture is heated to 80° C. over 2 hours, at which time the solution is a yellow color, and the color of the DFSA beads is a light reddish color. Analysis of the mixture by GC shows that all the DCF has been reacted. The solution is decanted, and the excess anisole is removed under vacuum. The product, a thick yellow oil, is analyzed by H and C-13 NMR (Nuclear Magnetic Resource). The pattern observed in the aromatic region of the H-NMR is consistent with para substitution of the anisole. The C-13 shows 12 carbons for the main product (a small amount of a byproduct is seen at the base of these peaks) which is the number of distinct carbon signals that would be predicted for the desired product. H-NMR: delta 3.79 (s, 6H, OCH$_3$), 7.89–6.86 (m, 16H), all from a standard of tetramethylsilane. C-13 NMR: delta 158.3, 151.9, 140.0, 138.2, 129.2, 127.6, 127.2, 126.1, 120.4, 113.6, 64.2 (quaternary C), 55.2 (OCH$_3$) from a standard of tetramethylsilane.

EXAMPLE 17

Polymerization of DCF with Diphenylcarbonate (DPC) using TiCl$_3$ Catalyst

DCF (9,9-Dichlorofluorene, 1.18 g, 0.005 mole) and DPC (diphenylcarbonate, 1.07 g, 0.005 mole) are weighed into a 25 mL two-necked flask fitted with a stirrer, heating mantle, and thermometer. Chloroform (4 mL) is added, followed by a catalytic amount of TiCl$_3$ (0.03 g, 0.0002 mole) and the mixture is stirred and heated to 60° C. over a period of 4 hours. After 30 minutes, the mixture has turned a dark red color, and is evolving HCl. After stirring for about 4 hours from the addition of the catalyst, the mixture solidifies and forms brown paste. The paste is dissolved in dichloromethane (except some insoluble portions), and then diluted with acetone. This causes the precipitation of the product as a brown powder which is filtered from the yellow solution. The melting point of the powder is >280° C.

EXAMPLE 18

Polymerization of DCF with Diphenyloxide (DPO) using ZnCl$_2$ as Catalyst

DCF (9,9-Dichlorofluorene, 5.88 g, 0.025 mole) is weighed into a 150 mL resin kettle along with diphenyl oxide (DPO) (4.28 g, 0.0251 mole) and chloroform (10 mL). The kettle is fitted with a condenser and mechanical stirrer, and a starting GC (using a gas chromatograph commercially available from Varian Associates under the trade designation Model 3700, with a 30 meter column coated with a 1 micron layer of polydimethylsiloxane commercially available from J&W Scientific under the trade designation DB-1) is taken as a reference. The mixture is stirred and heated in a water bath (40°–50° C.). A small amount of ZnCl$_2$ is added (about 0.02 g) and the mixture is stirred and heated at 50–70° C. After 30 minutes of heating the mixture has turned a dark green color, and is evolving HCl. Shortly thereafter, a thick solid paste is deposited on the walls of the kettle. This thick paste does not dissolve when 100 mL chloroform is added. The paste is triturated with acetone, which causes the solid to turn off-white in color. The off-white solid is filtered from the acetone and dried. The acetone is evaporated to yield a greenish semi-solid. The off-white polymer weighs 5 grams (60 percent of theoretical) and has a melting point (under a pressure of 68,000 kPa) of 250° C. The polymer is pressed into a thin, clear film at 250° C. and about 10,000 psig (700 kg/cm$^2$). The film is brittle indicating low molecular weight. The Tg of the polymer is measured at 179° C. (onset) by DSC (Differential Scanning Calorimetry).

EXAMPLE 19

Reaction of 9,9-Dichlorofluorene with Phenol to Prepare 9,9-Bis(hydroxyphenyl)fluorene This reaction is carried out in a reactor constructed from fluorocarbon resin commercially available from E.I. du Pont de Nemours & Co. under the trade designation TEFLON PFA in the form of 2 inch (5.08 cm) diameter pipe 12 inches (30.48 cm) in length. At the top of the reactor is a ½ inch (1.27 cm) diameter port containing a ball valve through which phenol is added to the reactor. Also attached to the top of the reactor is a nitrogen purge line as well as a vent line (attached to a sodium hydroxide scrubber). Attached two inches (5.08 cm) above the bottom of the reactor is (1) a thermowell and (2) an inlet line which serves as a point of HCl injection and/or sampling of the reaction mixture. Contained in the reactor is a star-shaped magnetic stir bar which, when acted upon by an external magnetic stir plate, provides agitation to the reaction mixture. Approximately six inches (15.24 cm) from the bottom of the reactor is attached a feed line through which a solution of 9,9-dichlorofluorene (DCF) (or other dichloro compound) is passed into the reactor from an external holding tank. The reactor is wrapped with an electric heating tape attached to a variable voltage controller which serves to regulate the temperature of the reaction mixture.

Molten (60° C.) phenol (94.1 g, 1.0 mole) is poured into the reactor and the ball valve closed. While the phenol is stirred, the variable voltage controller is adjusted to maintain the phenol temperature between 40° and 45° C. A sample of 63.9 grams of a solution of DCF in carbon tetrachloride and containing 6.45 g (0.027 mole) of DCF, are placed in the DCF holding tank. When reactor temperature is stable, anhydrous HCl is passed slowly into the phenol until reactor pressure is approximately 15 psig (pounds per square inch gauge) (102 kPag). At this point, HCl addition is ceased and nitrogen pressure is used to force the DCF solution from the holding tank into the reactor. Total time for addition of the DCF solution is approximately 30 seconds. Reactor pressure is maintained at approximately 20 psig (136 kPag) by adjusting flow through the vent line with a needle valve. After 2 hours reaction time, the reactor contents are removed and quantitatively analyzed by reverse phase liquid chromatography (HPLC). Selectivity to p,p-BHPF is found to be 70 percent.

EXAMPLE 20

Effect of Phenol: DCF Molar Ratio

The procedure of EXAMPLE 19 is repeated except that 509.7 g of the DCF solution (0.23 mole DCF) are added to the reactor and reactor pressure is 90 psig (612 kPag). After 2 hours reaction time, the reactor contents are removed and treated with 167 g isopropyl alcohol, then quantitatively analyzed by reverse phase liquid chromatography (HPLC). Selectivity to p,p-BHPF is 54 percent.

EXAMPLE 21

Effect of Using Methanesulfonic Acid (MSA) as Catalyst

The procedure of EXAMPLE 20 is repeated except 100 g (1.06 mole) of phenol and 5 g methanesulfonic acid (MSA) are placed in the reactor and 267.8 g of a DCF/carbon tetrachloride solution (7.9 percent weight/weight in DCF) are added to the reactor and no HCl is passed into the reactor. After approximately 2 hours reaction time, the temperature of the reaction mixture is increased from 40°–45° C. to approximately 70° C. and maintained at these conditions for another 17 hours. The reaction mixture is quantitatively analyzed by reverse phase liquid chromatography (HPLC). Selectivity to p,p-BHPF is 86 percent.

EXAMPLE 22

USE of MSA at Atmospheric Pressure

A sample of 25.0 g (0.266 mole) phenol and 7.5 g methanesulfonic acid (MSA) are stirred in a 3-necked 250 mL round-bottom flask equipped with a Dewar condenser containing dry ice. A solution of DCF is prepared by adding 25.03 g (0.106 mole) DCF to a mixture containing 39.9 g methylene dichloride and 20.1 g chloroform. When the temperature of the phenol/MSA mixture is approximately 30° C., the DCF solution is added to the flask, via dropping funnel, over a 20 minute period. After 2½ hours reaction time, the reaction mixture is heated with a heating mantle to a temperature of 38°–40° C. and maintained at this temperature for 3 hours. The solution is then allowed to cool overnight. The reaction mixture is filtered and the filter cake washed with methylene chloride to yield a white solid which, after drying to constant weight at 60° C., yields 20.8 g of a white solid. HPLC analysis indicates the white solid to be 96 percent p,p-BHPF by peak area. Quantitative analysis of the filtrate by HPLC reveals 10.5 g p,p-BHPF to be dissolved in the filtrate. Overall selectivity to p,p-BHPF is 84 percent.

EXAMPLE 23

Effect of Water

The procedure of EXAMPLE 22 is repeated except a) 22.0 g (0.234 mole) phenol is used, b) the methylene chloride is saturated with deionized water prior to preparing the DCF solution and c) reaction temperature is 25° C. After 2 hours selectivity to p,p-BHPF is 62 percent.

EXAMPLE 24

Effect of Sulfuric Acid

A sample of 40.0 g (0.425 mole) phenol is added to a 250 mL Erlenmeyer flask containing a magnetic stir bar and fitted with a thermometer. With stirring, 5.6 g (0.06 mole) 96 percent sulfuric acid and 0.1 mL (1.15 millimole) β-mercaptopropionic acid are added to the phenol. A sample (25.0 g 0.106 mole) DCF is added as a solid to the phenol/acid mixture over a 20 minute period during which the temperature of the reaction mixture never exceeds 50° C. After 2 hours reaction, the reaction mixture is dissolved in isopropyl alcohol and quantitatively analyzed by HPLC. Selectivity going to p,p-BHPF is 70 percent.

EXAMPLE 25

Effect of Temperature

A sample of hot phenol. (249.2 g, 2.65 mole, at a temperature of 70° C.) is placed in a 1 liter, 3-necked round-bottomed flask fitted with a thermometer, distillation arm and a dropping funnel. While the contents are stirred and heated to approximately 100° C., anhydrous HCl is bubbled into the phenol. A sample of (250 mL) of a DCF/CCl$_4$ solution which contains 0.089 mole of DCF (as determined by HPLC analysis) is charged to the dropping funnel. When the temperature of the phenol/HCl solution has stabilized at 98° to 100° C., the DCF solution is slowly dripped into the phenol/HCl solution. As the DCF solution is added, a distillate is collected from the reaction mixture. When all of the DCF has been added, the HCl flow is discontinued and the contents of the flask are allowed to cool. After 15 hours total reaction time, the reaction mixture is quantitatively analyzed by HPLC. Selectivity is 66 percent going to p,p-BHPF.

EXAMPLE 26

Use of Trifluoromethanesulfonic (Triflic) Acid as Catalyst

The procedure of EXAMPLE 25 is repeated except that (a) 0.5 mL of triflic acid is added to the flask in lieu of HCl, and (b) 750 mL of the DCF/CCl$_4$ solution are placed in the dropping funnel. Selectivity is 50 percent relative to p,p-BHPF.

EXAMPLE 27

Use of Trifluoromethanesulfonic Acid as Catalyst

To a 100 mL 3-necked flask equipped with a thermometer, magnetic stir bar, condenser and a nitrogen inlet through which a positive nitrogen sweep is maintained, 32.4 g of phenol is added. The temperature is adjusted to 41° C. and nitrogen is swept through the system for ten minutes. At this point, triflic acid (0.1 mL) is added to the flask. Solid crystals of 9,9-dichlorofluorene, obtained by evaporating the solvent from the DCF/CCl$_4$ solution used in EXAMPLE 13, are added over the next hour. The temperature of the reaction mixture is maintained at 40° C. for four more hours and then sampled for HPLC analysis which shows a 91 percent yield.

EXAMPLE 28

Use of Ethyl Acetate as Solvent

The procedure of EXAMPLE 18 is repeated except a mixture of 91 g ethyl acetate and 100 g (1.06 mole) phenol are added to the reactor, 2) 24 g (0.102 mole) DCF are dissolved in 123 g ethyl acetate and placed in the DCF holding tank, 3) the DCF solution is added over a 5 minute period, 4) HCl addition is continued during DCF addition, reaction temperature is allowed to vary from room temperature to 41° C. and 5) reactor pressure is not controlled (never exceeds 22 psig (149.6 kPag)). After 16 hours reaction time, the reaction mixture is collected and quantitatively analyzed by HPLC. Selectivity to p,p-BHPF is 53 percent.

EXAMPLE 29

Use of Isopropanol as Solvent

A sample of 100 g isopropyl alcohol and 208 g (2.21 mole) phenol are combined and saturated with anhydrous HCl in a 500 mL erlenmeyer flask. A solution of 24 g (0.102 mole) DCF in 200 g carbon tetrachloride is added to the stirred phenol/alcohol solution over a 50 minute period during which the reaction mixture is continuously sparged with anhydrous HCl. After 95 minutes reaction time, the reaction mixture is collected and quantitatively analyzed by HPLC. Selectivity to p,p-BHPF is 69 percent.

EXAMPLE 30

Effect of Pressure, Temperature, and Time on Selectivity

The procedure of EXAMPLE 18 is repeated except temperature is controlled at 60°–70° C. and reactor pressure is controlled at 80–90 psig (612 kPag) and reaction time is 15.5 hours. Selectivity to p,p-BHPF is 85 percent.

EXAMPLE 31

Use of a Recirculating Reactor

The basic reactor configuration is 1) a 2 inch (5.08 cm) diameter pipe of fluorocarbon resin commercially available from E.I. du Pont de Nemours & Co. under the trade designation Teflon PFA which serves as the mixing tank, 2) a heat exchanger of the same material 3) a feed tank in which a solution of 9,9-dichlorofluorene is stored prior to starting the phenolation reaction and 4) a pump which continually circulates the reactor contents through the heat exchanger and mixing tank.

A solution of 57 g (0.6 mole) of phenol in approximately 236 mL of $CCl_4$ is placed in the reactor mixing tank. After the reactor is sealed, the pump is energized, and the solution is allowed to circulate through the system. At this point an ethylene glycol/water mixture commercially available from The Dow Chemical Company under the trade designation Ambitrol™ 50 which has been cooled to 10° C., is admitted to the heat exchanger to maintain a reactor temperature of 17° C. Upon stabilization of the $CCl_4$/phenol solution temperature, anhydrous HCl is admitted into the headspace of the mixing tank, and reactor pressure is regulated at 10 psig (68 kPag) by means of a flow meter on the vent line. A solution of $CCl_4$/9,9-dichloro fluorene (DCF) is prepared by dissolving 14.1 g (0.06 mole) of DCF in approximately 88 mL of $CCl_4$. The solution is charged to the DCF feed tank and pressured to 30 psig (204 kPag) with nitrogen. A flow meter connecting the DCF feed tank to the suction of the circulating pump is then opened to admit the DCF/$CCl_4$ solution into the reactor system at a rate of 3.1 g/minute. Samples of the reaction mixture are periodically removed via the sampling line and analyzed by reverse phase liquid chromatography (HPLC) to determine extent of reaction and distribution of reaction products. After 23 hours reaction time, the reaction mixture is analyzed by HPLC. p,p-BHPF comprises 44 percent of all reaction products as measured by peak area.

EXAMPLE 32

Effect of Phenol Concentration and Temperature

The procedure of EXAMPLE 31 is repeated except: a) 191.3 g (2.04 mole) phenol is added to the reactor followed by 180 mL $CCl_4$, b) 250 mL of a DCF/$CCl_4$ solution containing 0,089 mole of DCF (as determined by HPLC analysis) is charged to the DCF feed tank, c) reactor temperature is controlled at 64° C. After 6 hours, the reaction mixture is analyzed by HPLC; analysis shows p,p-BHPF comprises 49 percent of all reaction products as measured by peak area.

EXAMPLE 33

Use of Glacial Acetic Acid as Solvent

The procedure of EXAMPLE 31 is repeated except that 100 g (1.1 mole) of phenol and 100 mL of glacial acetic acid are placed in the reactor mixing tank. The reactor is sealed, the pump is energized, and the solution is allowed to circulate through the system. At this point an ethylene glycol/water mixture commercially available from The Dow Chemical Company under the trade designation Ambitrol™ 50, which has been cooled to 25° C., is admitted to the heat exchanger to maintain a reactor temperature of 30° C. Upon stabilization of the phenol temperature, anhydrous HCl is injected into the suction of the circulation pump until reactor pressure is 20 psig (136 kPag), at which point the HCl flow is discontinued. A solution of $CCl_4$/9,9-dichloro fluorene (prepared by dissolving 24 g (0.1 mole) of DCF in approximately 60 mL of $CCl_4$ and 200 mL glacial acetic acid) is charged to the DCF feed tank and pressured to 40 psig (272 kPag) with nitrogen. A flow meter connecting the DCF feed tank to the suction of the circulating pump is then opened to admit the DCF/$CCl_4$ solution into the reactor system at a rate of 5.5 g/min. The reaction mixture is analyzed by HPLC. Selectivity to p,p-BHPF is 27 percent.

EXAMPLE 34

Use of Catalyst Dissolved in DCF

A sample of 24.0 g (0.102 mole) DCF is dissolved in 88 g ethyl acetate. This solution is sparged with anhydrous HCl until 13.1 g HCl has dissolved in the solution. A sample of 297 g (3.16 mole) molten (60° C.) phenol is placed in a 1-L Erlenmeyer flask and stirred. The ethyl acetate/DCF/HCl solution is added slowly to the phenol. HPLC analysis indicates 84 percent of product peak area is that of p,p-BHPF.

EXAMPLE 35

Reverse Addition: Phenol into DCF

The procedure of EXAMPLE 34 is repeated except that the ethyl acetate/DCF/HCl solution is placed in a 500 mL Erlenmeyer flask and stirred while HCl is sparged through the solution. Molten (60° C.) phenol is added to the ethyl acetate/DCF/HCl solution over a 1 hour period. After 4.3 hours, HPLC analysis shows p,p-BHPF to be 74 percent of the products' peak areas.

EXAMPLE 36

Use of Propylene Carbonate as Solvent

A sample of 1.1 g (0.012 mole) phenol is dissolved in 1.0 g propylene carbonate/0.1 mL β-mercaptopropionic acid (BMPA). A solution of 1.25 g (0.0053 mole) DCF in 2 g methylene chloride/1 g chloroform is added to the propylene carbonate/phenol/-BMPA solution. Anhydrous HCl is slowly sparged into the mixture to initiate reaction. After 1.5 hours, HPLC analysis shows p,p-BHPF to constitute 62 percent of the products' peak areas.

EXAMPLE 37

Direct Addition of Phenol to a Chlorination Reaction to Obtain p,p-BHPF

The reactor is a 1000 mL cylinder 4 inches in diameter (100 mm) by 5.5 inches in height (140 mm) equipped with a 2 inch (50 mm) diameter turbine impeller driven by a vertical shaft. Stirring rate is measured by a tachometer. Temperature is controlled by a 10 foot (3.048 m) by 0.25 inch (0.635 cm) external diameter coil immersed in the reaction medium through which coolant is pumped maintained at a constant temperature by a circulating refrigerated/heated bath.

The temperature is measured by a thermocouple inside a thermowell which runs the entire depth of the reactor. The reactor is also equipped with a nitrogen inlet which is used to maintain a nitrogen atmosphere above the reaction solution. The entire apparatus is constructed of polytetrafluoroethylene/copolyheptafluoropropyl trifluorovinyl ether commercially available from E.I. du Pont de Nemours & Co. under the trade designation Teflon PFA.

The reactor is flushed with nitrogen and a solution of fluorene (33.24 g, 0.200 mole) and carbon tetrachloride (299.20 g, 1.9451 mole, 187.70 mL) is charged to the reactor followed by NaOH (30 percent solution in watery 53.33 g, 0.40 mole, 40.10 mL, 16.00 g dry weight). The stirrer is started, and the speed adjusted to 4000 rpm. The coolant is admitted to the coils, and the temperature of the reaction solution is adjusted to 30° C. The catalyst, tetrabutylammonium hydroxide (40 percent solution in watery 2.59 g, 0.004 mole, 2.57 mL) is added at once. The reaction mixture is sampled after 30 minutes and analyzed by GC according to the procedure of EXAMPLE 1; analysis shows 0.38 percent fluorene, 98.74 percent 9,9-dichlorofluorene, and 0.88 percent 9-fluorenone. Phenol (41.41 g, 0.44 mole, 38.70 mL) in 42.46 mL of $CCl_4$ is added to the reactor and stirring is continued. After 30 minutes the reaction mixture is sampled and analyzed by reverse phase liquid chromatography (HPLC) as in EXAMPLE 19 which shows the composition of the mixture to now be 41.70 percent 9,9-bis(4-hydroxyphenyl)fluorene, 2.45 percent o,p-BHPF, 5.42 percent 9-fluorenone, and 4.76 percent 9,9-dichlorofluorene.

EXAMPLE 38

Addition of Phenol as Phenolate in Aqueous Solution Directly to the Chlorination Reaction to Obtain the pyp-BHPF The reactor described in EXAMPLE 37 is flushed with nitrogen, and a solution of fluorene (33.24 g, 0.200 mole), ethylbenzene (188.38 g, 1.7743 mole, 217.28 mL) and carbon tetrachloride (61.53 g, 0.400 mole, 38.60 mL) is charged to the reactor followed by NaOH (50 percent solution in water, 160.0 g, 2.00 mole, 103.9 mL, 80.00 g dry weight). The stirrer is started, and the speed adjusted to 3000 rpm. The coolant is admitted to the coils, and the temperature of the reaction solution is adjusted to 30° C. The catalyst, tetrabutylammonium hydroxide (40 percent solution in water, 2.59 g, 0.004 mole, 2.57 mL), is added at once. The reaction mixture is sampled after 1 minute and periodically thereafter for the next 30 minutes and analyzed by GC according to the procedure used in EXAMPLE 1. The results of these analyses are shown in Table 2.

TABLE 2

| TIME (Minutes) | percent Fluorene | percent 9,9-DCF | percent Fluorenone |
| --- | --- | --- | --- |
| 0.00 | 99.41 | 0.00 | 0.59 |
| 1.00 | 1.23 | 97.78 | 0.99 |
| 2.00 | 1.51 | 97.61 | 0.88 |
| 3.00 | 1.45 | 97.76 | 0.78 |
| 4.00 | 1.40 | 97.98 | 0.62 |
| 5.00 | 1.54 | 97.75 | 0.71 |
| 10.00 | 1.54 | 97.59 | 0.88 |
| 15.00 | 1.29 | 97.84 | 0.87 |
| 20.00 | 1.21 | 97.92 | 0.87 |
| 30.00 | 1.15 | 98.10 | 0.75 |

The data in Table 2 show that the reaction is essentially complete within one minute. GC analysis at one minute shows 1.23 percent fluorene, 97.78 percent 9,9-dichlorofluorene, and 0.59 percent 9-fluorenone. After 30 minutes, phenol (37.64 g, 0.40 mole, 35.18 mL) in 10.39 mL of 50 percent NaOH (0.40 mole, 16.00 g dry weight) is added to the reactor and stirring continued. After 30 minutes analysis shows 76.97 percent DCF remaining and 1.96 percent BHPF. The mixture is allowed to stir overnight; then analysis shows 100.0 percent 9,9-bis(4-hydroxyphenyl)fluorene.

EXAMPLE 39

Preparation of Bis(aminophenyl)fluorene

Into a two-neck round bottomed flask provided with a thermometer and a condenser are placed 9,9-dichlorofluorene (10.0 g, 0.0425 mole) and aniline (50.0 g, 0.537 mole). The resulting mixture is slowly heated over a period of about 30 minutes to 60° C. in an oil bath with stirring using a magnetic stirrer. A rapid reaction takes place with an exotherm (~110° C.) and results in complete disappearance of dichlorofluorene and appearance of one product as confirmed by GC/MS (gas chromatographic mass spectrometry), showing a primary peak at 254–257 AMU, to be 9-chloro-9-(aminophenyl)fluorene. Further heating at 130° C. for three hours results in complete conversion of the monoamine to the diamine. Excess aniline is flash distilled under vacuum, and the resulting residue is washed with 5 percent sodium hydroxide, filtered, and washed with hexane to give 14.0 g (94 percent yield) of the diamine, which is found to be a mixture of 91 percent p,p'- and 9 percent N,p-isomers by GLC (gas liquid chromatography); m.p. 234°–235° C. The mass spectrum shows a primary peak at 348 AMU.

The diamine is recrystallized by pouring it into boiling toluene and cooling the resulting mixture to precipitate pure p,p'-isomer, m.p. 234°–235° C.; NMR ($^1H$ and $^{13}C$) data is consistent with 9,9-bis(paminophenyl)fluorene structure. The $^1H$ NMR of the compound in $d_6$-DMSO (deuterodimethylsulfoxide) shows peaks at δ4.90 (singlet, $NH_2$, 2H), 6.40 (doublet, aromatic, 4H), δ6.75 (doublet, aromatic, 4H), δ7.2–7.3 (multiplet, fluorene, 6H), δ7.8–7.9 (multiplet, fluorene, 2H), all from TMS (tetramethylsilane) standard.

When the procedure is repeated except that heating at 130° C. is continued for a period of 7 hours rather than 3 hours, the product is 98 percent p,p'- and 2 percent N,p-isomer. This data indicates that heating converts the N,p-isomer to the p,p'- isomer.

EXAMPLE 40

Effect of Recycling Byproducts to Increase para, para-BHPF

In this example, recycle is illustrated by 5 batch reactions.

Reaction #1: To a 100 mL glass flask equipped with a thermometer, stirring paddle, and a cooling/heating glycol jacket are added 15.98 grams (0.170 moles) of phenol in 8.60 grams of chloroform plus 3.07 grams of methanesulfonic acid (MSA) to form a solution. This solution is stirred and kept at 24° C. To this solution are added 18.04 g (0.0768 moles) of 9,9-dichlorofluorene (DCF) in 18.1 grams chloroform plus 8.4 grams methylene chloride over a period of 75 minutes. After the DCF is added, the temperature is 27° C. That temperature is maintained for 60 minutes, then the solution is cooled to 10° C. which is maintained 60 minutes. Crystals form and are collected on a glass filter frit and washed with a total of 100 mL of methylene chloride and then a total of 100 grams of warm water. The resulting 10.7 grams of BHPF is determined to be 99 percent pure by HPLC analysis, and the crystals have a melting point of 223°–225° C. This melting point indicates that the isomer is p,p-BHPF. The filtrate/methylene chloride wash is used for the recycle reaction below.

Reaction #2: Recycle: Eighty-four percent of the filtrate/methylene chloride wash from Reaction #1 is added back to the glass reactor used in Reaction #1 with 7.22 grams (0.0767 moles) of phenol and 0.49 grams of MSA. The resulting solution is heated to 70° C. which is maintained for one hour while most of the methylene chloride and chloroform are removed by vacuum distillation. Then the remaining mixture is cooled to 24° C. and 5 g of methylene chloride are added. Then the mixture is seeded with 0.005 g BHPF crystals to promote crystallization. After 10 minutes, 8.89 grams (0.0378 moles) of DCF dissolved in a mixture of 9.0 g CHCl$_3$ and 19 g CH$_2$Cl$_2$ are added over a period of 108 minutes. The temperature is raised to 40° C. and maintained at that temperature for 60 minutes, then cooled to 10° C. and maintained at that temperature for one hour. The resulting crystals are collected on a glass filter frit and washed as in Reaction #1. The resulting 13.1 grams of BHPF is determined to be 99 percent pure by HPLC analysis, and the crystals have a melting point of 223°–225° C. The filtrate/methylene chloride wash is used for the next recycle reaction, Reaction #3.

Reaction #3—Recycle: Eighty-five percent of the filtrate/methylene chloride wash from Reaction #2 is added back to the glass reactor used in Reactions #1 and #2, with 8.36 grams (0.0888 moles) of phenol and 0.46 grams of MSA. The resulting solution is heated to 70° C. and maintained at that temperature for one hour while most of the methylene chloride and chloroform are removed by vacuum distillation. Then the solution is cooled to 24° C., and 5 g of methylene chloride are added. Then the resulting mixture is seeded with 0.005 g BHPF crystals. After 10 minutes, 10.23 grams (0.0435 moles) of DCF in the same solvent mix as Reaction #2 are added over a period of 130 minutes. The temperature is raised to 40° C. and maintained at that temperature for 60 minutes, then cooled to 10° C. and maintained at that temperature for one hour. The resulting crystals are collected on a glass filter frit and washed as in Reaction #1. The resulting 11.9 grams of BHPF is determined to be 99 percent pure by HPLC analysis, and the crystals have a melting point of 223°–225° C. The filtrate/methylene chloride wash is used for the next recycle reaction, Reaction #4.

Reaction #4—Recycle: Eighty-five percent of the filtrate/methylene chloride wash from Reaction #3 is added back to the glass reactor used in Reactions #1 and #3 with 7.92 grams (0.0842 moles) of phenol and 0.46 grams of MSA. The resulting solution is heated to 70° C. and maintained at that temperature for one hour while most of the methylene chloride and chloroform are removed by vacuum distillation. Then the solution is cooled to 24° C. and seeded with 0.005 g BHPF crystals. After 10 minutes, 9.54 grams (0.0406 moles) of DCF in the same solvent mix used in Reaction #2 are added over a period of 110 minutes. The temperature is raised to 40° C. and maintained at that temperature for 60 minutes, then cooled to 10° C. and maintained at that temperature for one hour. The resulting crystals are collected on a glass filter frit and washed as in Reaction #3. The resulting 11.4 grams of BHPF is determined to be 99 percent pure by HPLC analysis, and the crystals have a melting point of 223°–225° C. The filtrate/methylene chloride wash is used for the next recycle reaction, Reaction #5.

Reaction #5—Recycle: Eighty-five percent of the filtrate/methylene chloride wash from Reaction #4 is added back to the glass reactor used in Reactions #1 and #4 with 7.58 grams (0.0805 moles) of phenol and 0.45 grams of MSA. The resulting solution is heated to 70° C. and maintained at that temperature for one hour while most of the methylene chloride and chloroform are removed by vacuum distillation. Then the solution is cooled to 24° C., and 5 g of methylene chloride are added. Then the mixture is seeded with 0.005 g BHPF crystals. After 10 minutes, 9.21 grams (0.0392 moles) of DCF in the same solvent mix as Reaction #2 are added over a period of 115 minutes. The temperature is raised to 40° C. and maintained at that temperature for 60 minutes, then cooled to 10° C. and maintained at that temperature for one hour. The resulting crystals are collected on a glass filter frit and washed as in Reaction #1. The resulting 11.0 grams of BHPF is determined to be 99 percent pure by HPLC analysis, and the crystals have a melting point of 223°–225° C.

The results of Reactions #2–#5 shows the usefulness of a recycle process to convert the byproducts of the reaction to BHPF using MSA as the catalyst. A steady state is produced where the conversion rate to BHPF is 95 percent. [(moles of BHPF/moles of DCF feed −15 percent, which is removed) X 100=95 percent]

EXAMPLE 41

Recycle to form p,p-BHPF Exemplified in 3 Reactions

Reaction #41:1 To a 100 mL glass flask equipped with a thermometer, stirring paddle, and a cooling/heating glycol jacket are added 15.98 grams (0.170 moles) of phenol in 8.60 grams of chloroform plus 3.07 grams of methane sulfonic acid (MSA). The resulting solution is stirred and heated to 68° C. To the solution, are added 18.04 g (0.0768 moles) of dichlorofluorene (DCF) in 18.1 grams chloroform plus 38.4 grams methylene chloride over 60 minutes. After the DCF is added, the temperature is kept at 68° C. and maintained at that temperature for 30 minutes then slowly dropped to 45° C. over a period of 20 minutes. Then the solution is seeded with 0.005 g BHPF crystals. The temperature is decreased to 10° C. while 26 grams of methylene chloride are added. The temperature is maintained at 10° C. for 60 minutes. The resulting crystals are collected on a glass filter frit and washed with 100 g methylene chloride and then with 100 g warm water. The resulting 12.9 grams of BHPF are determined to be 99 percent pure by HPLC analysis, and the crystals have a melting point of 223°–225° C. The filtrate/methylene chloride wash is used for the recycle reaction, Reaction #41:2.

Reaction #41:2—Recycle: To the glass reactor described in Reaction 41:1 is added the flitrate/methylene chloride wash from Reaction #41:1 with 8.12 grams (0.0863 moles) of phenol to form a solution. The solution is stirred and heated to 68° C. To the solution, are added 10.04 g (0.0427 moles) of DCF in 10.0 grams chloroform plus 21.4 grams methylene chloride over 67 minutes. After the DCF is added, the temperature is maintained at 68° C. and maintained at that temperature for 50 minutes then slowly dropped to 45° C. Then, 5 g of methylene chloride are added and the mixture is seeded with 0.005 g BHPF crystals. The temperature is decreased to 10° C. while 25 grams of methylene chloride are added. The temperature is maintained at 10° C. and maintained at that temperature for 60 minutes. The resulting crystals are collected on a glass filter frit and washed with methylene chloride and then warm water as in Reaction 41:1. The resulting t0.6 grams of BHPF is determined to be 99 percent pure by HPLC analysis, and the crystals have a melting point of 222°–225° C. The flitrate/methylene chloride wash is used for the recycle reaction, Reaction 41:3.

Reaction #41:3—Recycle: To the glass reactor used in Reactions #41:1 and #41:2 is added the flitrate/methylene chloride wash from Reaction #41:2 with 5.72 grams (0.0608 moles) of phenol to form a solution. This solution is stirred and heated to 68° C. and maintained at that temperature for 90 minutes. The temperature is decreased to 30° C., then 7.04 g (0.0300 moles) of DCF in 7.14 grams chloroform plus 15.1 grams methylene chloride are added over a period of 90 minutes. After the DCF has been added, the temperature is lowered to 10° C. and maintained at 10° C. for 60 minutes. The resulting crystals are collected on a glass filter frit and washed with methylene chloride and then warm water as is Reaction 41:1. The resulting 10.0 grams of BHPF is determined to be 99 percent pure by HPLC analysis, and the crystals have a melting point of 223°–225° C.

The results of Reactions #41:2–#41:3 show that conversion of byproduct to BHPF takes place and that recycle is, therefore, useful.

EXAMPLE 42

Use of Tetraalkylammonium Hydroxide as Base in Chlorination of Fluorene

The reactor used in EXAMPLE 1 is flushed with nitrogen. A solution of fluorene (12.50 g, 0.0752 mole), ethylbenzene (112.50 g, 1.0596 mole, 129.76 mL) and carbon tetrachloride (23.14 g, 0.150 mole, 1.451 mL) is charged to the reactor. The stirrer is started and the speed adjusted to 500 rpm. The temperature of the reaction solution is 30° C. The catalyst, tetrabutylammonium hydroxide (40 percent solution in water, 24.39 g, 0.0376 mole, 24.15 mL) is added at once. The reaction mixture is sampled after 5 minutes and periodically thereafter for the next 30 minutes and analyzed by GC by the procedure described in EXAMPLE 1. The results of these analyses are shown in Table 3. The reaction is essentially complete within thirty minutes. GC analysis at five minutes shows that the reaction mixture contains 33.26 percent fluorene, and 66.74 percent 9,9-dichlorofluorene. After 30 minutes GC analysis shows that the reaction mixture contains 0.14 percent fluorene, and 99.86 percent 9,9-dichlorofluorene.

TABLE 3

| TIME (Minutes) | percent Fluorene | percent 9,9-DCF | percent Fluorenone |
| --- | --- | --- | --- |
| 0.00 | 100.00 | 0.00 | 0.00 |
| 5.00 | 33.26 | 66.74 | 0.00 |
| 10.00 | 14.07 | 85.93 | 0.00 |
| 15.00 | 11.03 | 88.97 | 0.00 |
| 30.00 | 0.14 | 99.86 | 0.00 |

This example shows that organic bases like tetraalkylammonium hydroxides are useful in chlorination processes of the invention.

EXAMPLE 43

Use of an Ion Exchange Catalyst

To a 100 mL flask is added 20 grams (0.2125 moles) of phenol plus 13 grams of $CCl_4$ and 6.67 grams of a dried acid ion exchange resin commercially available from The Dow Chemical Company under the trade designation MSC-1. The flask is heated to 40° C., and 5.15 grams (0.0219 moles) of DCF in 60.8 grams of $CCl_4/CHCl_3$ are added over a one hour period. The temperature is raised to 60° C. and maintained for a period of one hour. HPLC analysis indicates 84 percent selectivity to p,p-BHPF.

EXAMPLE 44

Use of an Acid Clay Catalyst

To a 100 mL flask is added 20 grams (0.2125 moles) of phenol plus 14 grams of $CCl_4$ and 6.00 grams of a dried clay acid catalyst commercially available from Harshaw/Filtrol under the trade designation Filtrol-22. The flask is heated to 40° C., and 5.07 grams (0.0216 moles) of DCF in 59.9 grams of $CCl_4/CHCl_3$ are added over a one hour period. The temperature is kept at 40° C. for 20 minutes then cooled to 24° C. The BHPF crystals are collected by filtration, leaving a filtrate, and dried at 40° C. for 16 hours under a vacuum of 28 in Hg (6.7 kPa) to give 5.7 grams of product. The catalyst is washed with acetonitrile. HPLC analysis of the acetonitrile plus the filtrate shows 1.10 grams of BHPF in the solution. Total selectivity is 90 percent to p,p-BHPF.

EXAMPLE 45

Use of a Fluorocarbon Sulfonic Acid Catalyst

To a 100 mL flask is added 18.3 grams (0.1945 mol) of phenol plus 18.5 grams of $CCl_4$ and 10.0 grams of fluorocarbon sulfonic acid catalyst (0.139 meq/g) prepared by the process disclosed in U.S. Pat. No. 4,791,081 and available from The Dow Chemical Company under the trade designation XU-40036.01 (DFSA). The flask is heated to 40° C. and 4.95 grams (0.0210 moles) of DCF in 58.5 grams of $CCl_4/CHCl_3$ are added over 7.5 hours. HPLC analysis indicates 90 percent selectivity to p,p-BHPF.

EXAMPLE 46

Effect of Metals on Chlorination

The reactor is a 500 mL 3-neck round bottom flask equipped with a magnetic stir bar, nitrogen purge and thermometer. The reactor is flushed with nitrogen and a solution of fluorene (15.00 g, 0.090 mole) and carbon tetrachloride (234.89 g, 1.52 mole, 147.36 mL) is charged to the reactor followed by NaOH (30 percent solution in water, 6.65 g, 0.050 mole, 5.00 mL, 2.00 g dry weight). The stirrer is started, and the speed adjusted to 500 rpm. The mixture is stirred with a subsurface nitrogen sparge. The temperature of the reaction solution is 27° C. The catalyst, tetrabutylammonium hydroxide (40 percent solution in water, 4.95 g, 0.0076 mole, 4.90 mL) is added at once. The reaction is followed by gas chromatography (GC) as in Example 1. After 5 minutes, GC analysis shows that the reaction mixture contains 74.95 percent fluorene, and 25.05 percent 9,9-dichlorofluorene. The reaction is sampled and analyzed periodically over the next several hours until no fluorene remains according to the GC analysis.

This procedure is repeated with the addition of 10 g of each of the metals indicated in Table 4 to the flask before any of the other reagents. The results are tabulated in Table 4. The 304-stainless steel and 316-stainless steel are in the form of washers whereas the other metals are in the form of cuttings produced from drilling operations. These cuttings have much greater surface area than the washers but still have less inhibitory effect on the reaction than the stainless steel washers.

TABLE 4

Percent 9,9-DCF FORMED IN PRESENCE OF METAL

| TIME | GLASS | IRON | 304-SS* | 316-SS* | NICKEL | TI-TANIUM |
|------|-------|------|---------|---------|--------|-----------|
| 0.00 | 0.00 | 0.00 | 0.00 | 0.00 | 0.00 | 0.00 |
| 5.00 | 25.05 | 79.26 | 19.41 | 17.58 | 48.10 | 44.23 |
| 15.00 | 49.44 | 83.00 | 38.31 | 34.70 | 82.67 | 75.29 |
| 30.00 | 52.64 | 89.24 | 49.30 | 44.66 | 87.15 | 83.97 |
| 60.00 | 77.83 | 92.70 | 60.30 | 54.62 | 91.63 | 92.64 |
| 105.00 | 88.89 | 93.21 | 68.87 | 62.38 | 92.69 | 96.34 |
| 180.00 | 99.95 | 94.13 | 77.48 | 70.18 | 96.34 | 97.98 |
| 1020.00 | 100.00 | 94.10 | 77.08 | 69.89 | 96.23 | 97.56 |

*SS = Stainless Steel

In all cases tabulated where a metal is present, the reaction does not go to completion even after 17 hours; whereas, the reaction in glass with no metal present is 99.95 percent complete at three hours and all fluorene is converted at 17 hours. The large surface area of the cuttings is believed to contribute to mixing thereby resulting in higher initial rates of reaction for the mixtures where cuttings are present.

EXAMPLE 47

Use of Methylene Chloride as Solvent in Alkylation and Isolation without Water Wash A sample of 23.1 g (0.246 mole) phenol is placed in a 500 mL 3-necked round bottomed flask equipped with a magnetic stir bar, thermometer and dropping funnel. A solution prepared from 25.03 g (0.107 mole) DCF and 59 g methylene chloride is placed in the dropping funnel. While the phenol is still fluid (at 35° C.), drop-wise addition of the DCF solution is started and continued over a period of 90 minutes until all the solution has been added. Reaction temperature is maintained at room temperature (about 25° C.) during the course of the reaction. After 3 hours total reaction time, the reaction mixture is filtered to yield a solid which, after rinsing with methylene chloride and drying to constant weight at 60° C., weighs 20.8 g. HPLC analysis indicates the white solid to be greater than 95 percent p,p-BHPF by peak area. Quantitative analysis of the filtrate by HPLC indicates 3.5 g p,p-BHPF still dissolved in the filtrate. Selectivity to p,p-BHPF is 66 percent.

EXAMPLE 48

Non-aqueous Isolation of Alkylation Product where Chloroform is Alkylation Solvent To a 100 mL flask is added 6.2 grams (0.66 moles) of phenol plus 3.35 grams of $CHCl_3$ (chloroform). The flask is cooled to 11° C., and 6.0 grams (0.0255 moles) of DCF in 3.14 grams of $CHCl_3$ and 13.1 grams of $CH_2Cl_2$ is added within 5 seconds. The temperature is kept at 11° C. for 4 hours, then resulting BHPF crystals are collected on a glass filter frit, washed with 9 grams of $CH_2Cl_2$ and dried to give 4.63 grams of BHPF.

EXAMPLE 49

Continous Method for the Preparation of 9,9-Dichlorofluorene with Recovery and Recycle of the Phase Transfer Catalyst and Sodium Hydroxide Part A:

To the reactor described in Example 13 which has been purged with nitrogen is charged a volume of carbon tetrachloride (400 mL) such that its level just comes to the bottom of the sixth stage. NaOH solution (25 percent by weight, 6.14 moles, 245.6 g dry weight, 983 g solution weight, 774.0 mL) is then charged to the reactor, and fills all six of the stirred zones. The stirrer is started and its speed is adjusted to 1500 rpm. Fluorene (0.185 moles, 30.75 g) dissolved in carbon tetrachloride (2.24 moles, 344.8 g, 225.35 mL) is fed into a vertical catalyst saturator which is a cylinder 1 inch (2.54 cm) in diameter by 12 inches (30.48 cm) long containing the catalyst solution (tetrabutylammonium hydroxide (0.132 moles, 34.30 g dry weight, 85.75 g as 40 percent aqueous solution)) such that the feed solution falls through the aqueous catalyst solution before entering the first reactor stage, using a metering pump at a rate of 5.5 mL/min. The product solution is collected at the overflow and analyzed by gas chromatography (GC) according to the procedure of Example 13.

When fluorene is no longer detected in the effluent stream, the product is fed to a wash column which is identical in design to the reactor column. The product solution is fed to the first stirred stage at a rate of 5.5 mL/min and water is fed at the sixth stirred stage at a rate of 11.0 mL/min. The organic solution containing the 9,9-dichlorofluorene is collected at the overflow of the wash column and then passed through a column of molecular sieves (4A size, commercially available from Linde Division, Union Carbide Industrial Gasses Inc.) which lowers the water content of this stream as measured by Karl-Fisher titration from 208 ppm to 6.3 ppm. The total product solution collected in this fashion amounts to 1026 g which is evaporated to dryness on a rotary evaporator, leaving 42.52 g of very light yellow crystals, 9,9-dichlorofluorene (97.76 percent of the theoretical yield of 43.49 g).

The aqueous solution from the wash column is evaporated on the rotary evaporator (40° C./10 mm of Hg (1.32 kPa)) leaving 33.4 g of a clear oil which crystallizes (long needles) on cooling (97.4 percent recovery of the tetrabutylammonium hydroxide charged (34.30 g dry weight)).

Recycle run #1.

The tetabutylammonium hydroxide recovered from the above reaction (33.4 g, 0.129 moles) is dissolved in 57 mL water and charged to the catalyst saturator.

To the reactor which has been purged with nitrogen is charged a volume of carbon tetrachloride (400 mL) such that its level just comes to the bottom of the sixth stage. NaOH solution (the same solution used in the previous run (Example 49), Part A), 25 percent by weight, 6.14 moles, 245.6 g dry weight, 983 g solution weight, 774.0 mL) is then charged to the reactor, and fills all six of the stirred zones. The stirrer is started and its speed adjusted to 1500 rpm. Fluorene (0.185 moles, 30.75 g) dissolved in carbon tetrachloride (2.24 moles, 344.8 g, 225.35 mL) is fed into the catalyst saturator containing the catalyst solution using a metering pump at a rate of 5.5 mL/min. The product solution is collected at the overflow and washed and dried as in Part A. The total product solution collected in this fashion amounts to 1056 g which is evaporated to dryness on a rotary evaporator leaving 42.66 g of very light yellow crystals, 9,9-dichlorofluorene (98.1 percent of the theoretical yield of 43.49 g).

The aqueous solution from the wash column is evaporated on the rotary evaporator (40 C/10 mm of Hg (1.32 kPa)) leaving 32.7 g of a clear oil which crystallizes (long needles) on cooling (98.0 percent recovery of the tetrabutylammonium hydroxide charged (33.40 g dry weight).

Recycle run #2.

The tetrabutylammonium hydroxide recovered from the Recycle run #1 reaction (32.7 g, 0.126 moles) is dissolved in 55 mL water and charged to the catalyst saturator.

To the reactor which has been purged with nitrogen is charged a volume of carbon tetrachloride (400 mL) such that its level just comes to the bottom of the sixth stage. NaOH solution (the same solution used in Recycle run #1, 25 percent by weight, 6.14 moles, 245.6 g dry weight, 983 g solution weight, 774.0 mL) is then charged to the reactor, and fills all six of the stirred zones. The stirrer is started and its speed adjusted to 1500 rpm. Fluorene (0.185 moles, 30.75 g) dissolved in carbon tetrachloride (2.24 moles, 344.8 g, 225.35 mL) is fed into the catalyst saturator containing the catalyst solution using a metering pump at a rate of 5.5 mL/min. The product solution is collected at the overflow, washed and dried as in Part A. The total product solution collected in this fashion amounts to 1006 g which is evaporated to dryness on the rotary evaporation leaving 42.23 g of very light yellow crystals, 9,9-dichlorofluorene (97.1 percent of the theoretical yield of 43.49 g).

The aqueous solution from the wash column is evaporated on the rotary evaporator (40° C./10 mm (1.32 kPa)) leaving 32.5 g of a clear oil which crystallizes (long needles) on cooling (99.3 percent recovery of the tetrabutylammonium hydroxide charged (32.70 g dry weight).

Recycle run #3.

The tetrabutylammonium hydroxide recovered from the above reaction (32.5 g, 0.125 moles) is dissolved in 55 mL water and charged to the catalyst saturator.

To the reactor which has been purged with nitrogen is charged 400 mL carbon tetrachloride such that its level just comes to the bottom of the sixth stage. NaOH solution (the same solution used in Recycle run #2, 25 percent by weight, 6.14 moles, 245.6 g dry weight, 983 g solution weight, 774.0 mL) is then charged to the reactor, and fills all six of the stirred zones. The stirrer is started and its speed adjusted to 1500 rpm. Fluorene (0.185 moles, 30.75 g) dissolved in carbon tetrachloride (2.24 moles, 344.8 g, 225.35 mL) is fed into the catalyst saturator containing the catalyst solution using a metering pump at a rate of 5.5 mL/min. The product solution is collected at the overflow and washed and dried as in Recycle run #2. The total product solution collected in this fashion is 1046 g which is evaporated to dryness on the rotary evaporator leaving 41.11 g of very light yellow crystals, 9,9-dichlorofluorene (94.5 percent of a theoretical yield of 3.49 g).

The aqueous solution from the wash column is evaporated on the rotary evaporation (40° C./10 mm of Hg (1.32 kPa)) leaving 30–3 g of a clear amber oil (93.2 percent recovery of the tetrabutylammonium hydroxide charged (32.5 g dry weight )).

These results show that both the phase transfer catalyst and base can be recovered and/or reused (recycled) in the practice of the invention.

EXAMPLE 50

Alkylation of Dichlorofluorene onto Xylene

Ferric chloride (0.03 g, 0.2 mmole) is weighed into a 50 mL 3-necked flask fitted with a stirbar, nitrogen inlet, thermometer, and condenser with drying tube. A mixture of dichlorofluorene (4.7 g, 20 mmol) in o-xylene (anhydrous, 20 mL) is added by syringe. The addition is exothermic at the beginning, raising the temperature from 25° to 30° C. The reaction is heated by means of a heating mantle to a temperature of 40°–50° C. while a continuous stream of nitrogen is bubbled through the mixture. The solution rapidly exhibits a dark red color, and begins to evolve HCl. The mixture is analyzed by the procedure of Example 15 one hour after addition is complete and shows formation of a single product appearing as a single peak at 13.58 minutes. This material is worked up by diluting with methylene chloride, washing the resulting solution with water and 1M HCl, and then evaporating the solvent. The resulting tacky semisolid is then boiled in ethanol (100 mL) to precipitate a pale yellow solid. This solid is flushed through alumina with methylene chloride (100 mL), and the methylene chloride is quickly evaporated, leaving the product as a pale yellow semicrystalline solid, yield 7.47 g, 99.7 percent of theoretical. Analysis of the product by GC/MS showed 98.3 percent of the product as a single peak with 1.7 percent of the product as an isomer. The spectral peaks are: GC/MS: 375 (29.76); 374 (100.00); 360 (18.1); 359 (37.14); 269 (10.75); H-NMR: delta 2–2.5 (12H), 6.8–7.9 (14H).

EXAMPLE 51

Alkylation of Aniline

The procedure of example 39 is repeated except that aniline is used as the aromatic compound to produce 9,9-bis(4-aminophenyl)fluorene (abbreviated BAPF) in the number of equivalents indicated. Byproducts such as 9-(2-aminophenyl)-9-(4-aminophenyl)fluorene and N,p-BAPF are rearranged to p,p-BAPF. Formation of BAPF is followed by gas chromatography on a 15 m capillary column. Results shown in Table 5 indicate isomerization of byproducts to p,p-BAPF.

TABLE 5

BAPF PREPARATION

| | | Selectivity (%) | | | |
|---|---|---|---|---|---|
| Temp. (°C.) | React. Time (min) | p,p-BAPF | Monoamine | o,p-BAPF | N,p-BAPF |
| 135 | 30 | 60.05 | 17.55 | 1.37 | 19.97 |
| 135 | 60 | 81.57 | 2.80 | 1.41 | 14.20 |
| 135 | 90 | 81.56 | 2.70 | 2.30 | 13.43 |
| 135 | 120 | 87.32 | 1.75 | 1.49 | 7.42 |
| 135 | 150 | 93.23 | 0 | 2.17 | 4.59 |
| 135 | 210 | 95.57 | 0 | 1.89 | 2.53 |
| 135 | 300 | 95.71 | 0 | 2.32 | 1.96 |
| 135 | 390 | 96.38 | 0 | 1.89 | 1.72 |

The data in this table shows that over the indicated periods of time, product is formed and byproducts rearrange to the desired p,p-isomers.

The data in this table shows that over the indicated periods of time, product is formed and by products rearrange to the desired p,p-isomers.

EXAMPLE 52

Alkylation of Dichlorofluorene onto Benzocyclobutane

DCF (19.14 g, 0.0814 mole) and benzocyclobutane (69.12 g, 0,664 mole) are weighed into a dry 100 mL 14/20 flask and stirred under nitrogen until most of the DCF has dissolved. Antimony pentachloride (5 mL, 0.005 mole) is transferred by syringe into an oven-dried 250 mL three-necked flask fitted with a nitrogen inlet, stirbar, condenser, thermometer, and drying tube. Dry dichloromethane (65 mL) is added to the reaction flask and an additional 20 mL of dry dichloromethane is added to the DCF/BCB solution (for complete dissolution of the DCF). The catalyst solution in the reaction flask is stirred and purged with a stream of nitrogen as the DCF/BCB solution is added by syringe. The mixture turns burgundy immediately and gives off HCl. The reaction is warmed as necessary to maintain a temperature of about 40° C. An additional 15 mL of dichloromethane is used to rinse in the last of the DCF/BCB mixture into the reaction. After addition is complete, the mixture is heated at 40° C. for an additional 2 hours and then allowed to stir overnight.

GC analysis of the product shows no residual DCF. The dichloromethane solution is washed with water (with a color change to muddy yellow observed) and 0.5 molar HCl. The solution is dried over $MgSO_4$, and then concentrated by rotary evaporation to yield a thick brown glass which foams as the last of the solvent and residual BCB is removed forming a brittle gold foam which can be easily crushed.

The resulting gold colored powder is analyzed by LC and shows the expected mixture of bis-BCB adduct and BCB-fluorenone oligomers along with a small amount of fluorenone. The product is fairly soluble in acetone. Addition of the acetone solution to ethanol causes formation of a light-colored precipitate. However, as the solution is heated to remove the acetone, and the temperature of the solution approaches 60°–80° C., the product becomes tacky and the light-colored precipitate which has been suspended in the boiling mixture clumps together into a dark gold mass.

As the solution cools, a light-colored "crystalline" material precipitates. The ethanol is decanted from the precipitated product which is weighed and analyzed by LC. Only half of the theoretical amount of product is found in this portion, and LC analysis shows that a major portion of the bis-BCB adduct has been removed. The rest of the product (also containing an undetermined but significant amount of the bis adduct) has remained in the ethanol solution and is recovered by rotary evaporation.

The product is dissolved in wet tetrahydrofuran and treated with 0.1 g of sodium borohydride to convert residual fluorenone to alcohol. After 30 minutes of stirring, acetone is added, and the mixture is stirred for 30 minutes to destroy excess sodium borohydride. The solvent is removed by rotary evaporation, and the product is dissolved in carbon tetrachloride and treated with decolorizing carbon. The solution is flushed through neutral alumina to remove the fluorene alcohol and ionic compounds. The solvent is then removed by rotary evaporation to produce a light tan foam which is crushed. The material is analyzed by DSC, and the melting point of the material is found to be very broad, with initial softening occurring at about 50° C. and the material becoming definitely liquid by 100° C. NMR analysis (proton and carbon) shows very little ring damage.

Analysis of the powder by LC (liquid chromatography) shows it to be a mixture of 9,9-bis(benzocyclobutanyl)fluorene (about 58 percent), a 3:2 adduct, 9-benzocyclobutanyl-9-((9-benzocyclobutanylfluoren-9-yl)benzocyclobutanyl)fluorene (about 27 percent) and 15 percent higher oligomers. Proton NMR shows broad overlapping singlets at delta 3-3.2 from TMS (tetramethylsilane) ($CH_2$'s of the cyclobutane rings) and a complex pattern of multiplets at delta 7–7.9 (aromatic protons) in a ratio of 1:2, aliphatic to aromatic. Carbon NMR shows three signals for aliphatic $CH_2$ at 29.35, 29.53, and 29.81 ppm (relative to TMS) and three signals for quaternary aliphatic carbons at 66.16, 66.33, and 66.40 ppm. The material is cured at 160° C. for one hour and 210° C. for 12 hours. The resulting amber-colored plaque shows a 2 percent loss in weight when heated to 400° C.

A small portion of the product (1.5 g) is placed in an aluminum weighing dish and degassed and melted under vacuum up to 115° C. The material is cured at 160° C. for 1 hour and then cured at 210° C. for 12 hours. A clear amber-colored plaque is obtained which is somewhat brittle. The resulting amber-colored plaque shows a 2 percent loss in weight when heated to 400° C.

EXAMPLE 53

Alkylation of Dichlorofluorene onto p-Cresol

Dichlorofluorene (23.66 g) is weighed into a 500 mL four-necked round-bottomed flask equipped with a magnetic stir bar, heating mantle, thermometer, nitrogen inlet and drying tube. Molten p-cresol (114 g, about 40° C.) is added rapidly and the mixture immediately turns purple and begins to vent HCl. The mixture is stirred for one hour under a sweep of nitrogen. Analysis of the mixture by GC shows formation of a single product. After stirring for an additional hour during which much of the product precipitates, the excess p-cresol is removed by vacuum distillation. The residue is recrystallized from carbon tetrachloride to yield 9,9-bis(2-hydroxy-5-methylphenyl)fluorene in greater than 95 percent yield. H-NMR (relative to TMS) delta 1.93 (singlet, 6H, $CH_3$), 6.41 (singlet, 2H), 6.59–6.74 (AB, 4H), 7.17–7.32 (multiplet, 4H), 7.76–7.95 (multiplet, 4H), 8.81 (singlet, 2H, OH). C-NMR: (ppm) 151.76, 150.56, 137.63, 129.18, 125.59, 125.40, 125.32, 124.54, 124.48, 117.99, 113.83, 60.37 (quaternary carbon), 18.75 ($CH_3$). This bisphenol is cyclized to the spirocyclic ether, 2',7'-dimethylspiro[9H-fluorene-9,9'-[9H]xanthene] by refluxing in toluene with catalytic amounts of triflic, toluenesulfonic, or methanesulfonic acid, or by refluxing in acetonitrile/water. The spirocyclic ether is easily separated from the starting bisphenol by slurrying mixtures of the two in a nonsolvent for the spiro-ether such as acetonitrile followed by filtration. H-NMR delta 2.02 (singlet, 6H, $CH_3$), 6.16–6.17 (multiplet, 2H), 6.96–7.0 (multiplet, 2H), 7.0–7.4 (multiplet, 8H), 7.80–7.84 (multiplet, 2H). C-NMR: (ppm) 154.99, 149.37, 139.57, 132.24, 128.81, 128.28, 127.67, 127.60, 125.65, 124.35, 119.8, 116.33, 54.22 (quaternary carbon), 20.56 ($CH_3$).

EXAMPLE 54

Alkylation of Dichlorofluorene onto Resorcinol

Dichlorofluorene (23.51 g) is added to a solution of resorcinol (110.11 g) in 500 mL of dry acetonitrile with stirring. The mixture is held at about 40° C. and swept with nitrogen for 4 hours. Analysis of the reaction mixture by LC shows formation of the bisphenol 9,9-bis(2,4-dihydroxyphenyl)fluorene as the major product (about 60 percent) with the balance as the spirocyclized bisphenol ether spiro[fluorene-9,9'-xanthene]-3',6'-diol (about 25 percent) and higher oligomers. The excess resorcinol is removed by vacuum distillation.

Recrystallization of the residue from acetonitrile affords a purified sample of the bisphenol. H-NMR (relative to TMS) (in DMSO): delta 5.88–6.40 (m, 6H), 7.15–7.30 (m, 4H), 7.75–7.78 (m, 4H), 8.84 (s, 2H, OH), 8.93 (s, 2H, OH). C-NMR (ppm): 158.8, 156.77, 153.55, 139.63, 127.37, 126.94, 126.40, 119.97, 106.56, 105.36, 103.56, 61.44 (quaternary carbon). The crude mixture is converted to the spirocyclic bisphenol ether, spiro[fluorene-9,9'-xanthene]-3',6'-diol by treatment with acid or refluxing in toluene with acid catalyst as in Example 52. H-NMR (DMSO): delta 6.3–6.9 (m, 5H), 7.3–8.2 (multiplet, 8H), 9.8 (singlet, 2H).

EXAMPLE 55

Alkylation of Dichlorofluorene onto Hydroquinone

The reaction is carried out using the same procedure as in Example 54, substituting hydroquinone for resorcinol. The spirocyclic bisphenol ether, spiro[fluorene-9,9'-xanthene]-2',7'-diol is isolated as an off-white powder. H-NMR (DMSO): delta 5.9–6.95 (multiplet, 4H), 7.38–8.25 (multiplet, 1 OH), 9.2 5 (singlet, 2H)

EXAMPLE 56.

Alkylation of Dichlorofluorene onto a Mixture of Benzocyclobutane and Phenyl Ether.

The reaction is carried out using the same procedure as Example 52, substituting a solution of dichlorofluorene, benzocyclobutane and phenyl ether (2:6:1 molar ratio) in dichloromethane for the solution of dichlorofluorene and benzocyclobutane. The reaction mixture is flushed through neutral alumina to remove antimony salts and the product is isolated from the solution by rotary evaporation. The resulting brittle orange foam is crushed to a powder, dissolved in dichloromethane and treated with decolorizing carbon. Evaporation of the solvent yields a yellow powder. H-NMR:delta 2.95–3.2 (broad overlapping singlets, $CH_2$'s), 6.82–8.0 (multiplet, aromatic H) in a ratio of 1:5.

EXAMPLE 57

Preparation of Spiro[9H-fluorene-9,9'-[9H]xanthene]-2',7'-dicarboxylic acid; Oxidation of 2',7'-Dimethylspiro[9H-fluorene-9,9'-[9H]xanthene]

Cobalt acetate dihydrate (0.25 g), 2',7'-dimethylspiro[9H-fluorene-9,9'-[9H]xanthene] (1.8 g), o-dichlorobenzene (10 mL), and acetic acid (8 mL) are transferred into a 25 mL three-necked round-bottomed flask equipped with a magnetic stirbar, condenser, air inlet, and thermometer. Hydrobromic acid (30 percent by weight in acetic acid, 0.2 mL) is added by syringe and the mixture is stirred and heated to 120°–125° C. as a stream of air is rapidly bubbled through the solution. The progress of the reaction is followed by LC analysis. Heating and aeration of the reaction are continued for 48 hours. The reaction mixture is then cooled and washed with water to remove the acetic acid. The organic layer is extracted with aqueous sodium hydroxide (1M) to remove the product acid as its sodium salt. Acidification of the base layer with concentrated HCl causes precipitation of the product, spiro[fluorene-9,9'-xanthene]-2',7'-dicarboxylic acid, as a yellowish powder, which is filtered off, washed with water and dried. H-NMR (DMSO): delta 6.88–6.89 (m, 2H), 7.05–7.11 (m, 2H), 7.19–7.24 (m, 2H), 7.35–7.45 (m, 4H), 7.80–7.84 (m, 2H), 7.96–8.03 (m, 2H), 10.55 (bs, 2H). C-13 NMR (DMSO), (ppm): 166.09 (acid C=O), 154.19, 153.35, 139.02, 129.95, 129.22, 128.92, 128.58, 126.51, 125.23, 124.29, 120.81, 117.34, 53.14 (quaternary carbon) where m=multiplet, s=singlet and bs=broad singlet.

EXAMPLE 58

Preparation of 9,9-Bis(3,4-diaminophenyl)fluorene; Alkylation of 9,9-Dichlorofluorene with o-Phenylene Diamine Into a three-necked 100 mL round-bottomed flask is placed o-phenylene diamine (26 g). The flask is then equipped with a drying tube, magnetic stirbar, thermometer, powder addition funnel, and nitrogen inlet. The o-phenylene diamine is then stirred and heated to 105° C. and solid 9,9-dichlorofluorene is added to the melt. An immediate reaction occurs as evidenced by a color change to dark brown, formation of a copious precipitate and an increase in temperature to 110°–120° C. The temperature is then increased to 130° C. and held there for 4 hours during which time the mixture becomes more liquid. The reaction is then allowed to cool and the excess o-phenylenediamine is removed by pouring the reaction mixture into ethanol and filtering. The resulting dark brown solid is recrystallized from toluene to yield 9,9-bis(3,4-diaminophenyl)fluorene. H-NMR (DMSO): delta 4.97 (bs, 8H, $NH_2$), 6.07–6.11 (m, 2H), 6.31–6.42 (m, 4H), 7.17–7.33 (m, 6H), 7.76–7.79 (m, 2H). C-13 NMR (DMSO) (ppm): 152.55, 139.71, 136.29, 134.37, 132.64, 127.56, 127.17, 126.40, 120.37, 118.36, 117.69, 115.63, 115.11, 64.4 (quaternary carbon) where s=singlet, m=multiplet, and bs=broad singlet.

Example 59

Preparation of 9,9-Bis(4-amino-3-ethylphenyl)fluorene.

The procedure of Example 39 is repeated except that 0.537 mole of 2-ethylaniline is used in place of aniline and, after stirring at 60° C., the temperature is raised to 175° C. 9,9-Bis(4-amino-3-ethylphenyl)fluorene (abbreviated EAPF), has a molecular weight of 404 (determined by mass spectroscopy) and a melting point of 191°–192° C., and is prepared in 92 percent yield. Results are shown in Table 6.

Example 60

Alkylation of 2-Ethylaniline

The procedure of Example 59 is repeated. After the reaction temperature is raised to 175° C., the formation of 9,9-bis(4-amino-3-ethylphenyl)fluorene isomers (abbreviated BEAPF) is followed by gas chromatography on a 15 m capillary column. The results are shown in Table 6.

TABLE 6

| | | BEAPF PREPARATION | | |
|---|---|---|---|---|
| Temp. | React. Time | | Selectivity (%) | |
| (°C.) | (hours) | p,p-BEAPF | Monoamine | N,p-BEAPF |
| 175 | 1 | 40.47 | 40.47 | 1.11 |
| 175 | 2 | 79.80 | 18.84 | 1.36 |
| 175 | 3 | 88.09 | 10.35 | 1.56 |
| 175 | 4 | 92.40 | 6.28 | 1.33 |
| 175 | 5 | 94.83 | 4.16 | 1.01 |
| 175 | 6 | 96.59 | 2.31 | 1.10 |

*Formation of o,p-isomer was not observed

The data in this table shows that over the indicated periods of time, product is formed and byproducts rearrange to the desired p,p-isomers.

Example 61

Preparation of 9,9-Bis(N-methyl-4-aminophenyl)fluorene.

The procedure of Example 39 is repeated except that 0.537 mole of N-methylaniline is used in place of the aniline and, after stirring at 60° C., the temperature is raised to 135° C. 9,9-Bis(N-methyl-4-aminophenyl)fluorene (abbreviated BNMAPF), has a molecular weight of 376 (as determined by mass spectroscopy) and a melting point of 203°–204° C., and is prepared in 85 percent yield. Results are shown in Table 7 in the next Example.

Example 62

Alkylation of N-methylaniline

The procedure of Example 59 is repeated using 0.537 mole of N-methylaniline. After the reaction temperature is raised to 135° C., the formation of 9,9-bis(N-methyl-4-aminophenyl)fluorene (abbreviated BNMAPF) is followed by gas chromatography on a 15 m capillary column. The data in Table 7 shows that over the indicated periods of time, product is formed and byproducts such as o,p-BNMAPF rearrange to the desired p,p-isomer.

TABLE 7

BNMAPF PREPARATION

| Temp. (°C.) | React. Time (min.) | p,p-BNMAPF | Monoamine | Dealkylated. by-product | o,p-BNMAPF |
|---|---|---|---|---|---|
| 135 | 60 | 86.6 | 1.9 | 2.1 | 9.4 |
| 135 | 120 | 89.4 | 3.4 | 1.3 | 5.9 |
| 135 | 180 | 91.2 | 1.5 | 2.2 | 5.1 |
| 135 | 235 | 93.0 | 1.0 | 2.0 | 4.1 |
| 135 | 310 | 92.0 | 2.1 | 3.1 | 2.8 |
| 135 | 460 | 92.3 | 2.5 | 3.5 | 1.7 |

The data in this table shows that over the indicated periods of time, product is formed and byproducts rearrange to the desired p,p-isomers.

Example 63

Preparation of 9,9-Bis(4-amino-3-chlorophenyl)fluorene.

The procedure of Example 39 is repeated except that 0.537 mole of 2-chloroaniline is used in place of the aniline and, after stirring at 60° C., the temperature is raised to 175° C. 9,9-Bis(4-amino-3-chlorophenyl)fluorene (abbreviated BACPF) has a molecular weight of 404 (as determined by mass spectroscopy) and a melting point of 235°–236° C., and is prepared in 94 percent yield. Results are shown in Table 8.

Example 64

Alkylation of 2-chloroaniline

The procedure of Example 63 is repeated. After the reaction temperature is raised to 175° C., the formation of 9,9-bis(4-amino-3-chlorophenyl)fluorene (abbreviated BACPF) is followed by gas chromatography on a 15 m capillary column. Results are shown in Table 8.

TABLE 8

BACPF PREPARATION

| Temp. (°C.) | React. Time (hr.) | p,p-BACPF | Monoamine | Fluorenone Byproduct | N,p-BACPF |
|---|---|---|---|---|---|
| 175 | 1 | 26.54 | 50.41 | 23.06 | 0.00 |
| 175 | 2 | 42.20 | 36.19 | 21.61 | 0.00 |
| 175 | 3 | 68.51 | 17.48 | 10.45 | 3.56 |
| 175 | 4 | 87.95 | 3.28 | 4.88 | 3.89 |
| 175 | 6 | 93.96 | 1.29 | 1.29 | 3.46 |
| 175 | 7 | 93.08 | 1.40 | 1.98 | 3.54 |

The data in this table shows that over the indicated periods of time, product is formed and byproducts rearrange to the desired p,p-isomers. The data in these tables shows that over the indicated periods of time, product is formed and byproducts such as o,p-BNMAPF and N,p-BAPF rearrange to the desired p,p-isomers.

EXAMPLE 65

Alkylation of Dichlorofluorene with 3,4-Dimethylphenol (Xylenol) and subsequent Oxidation and Hydrolysis of Resulting Products Dichlorofluorene (23.51 g, 0.10 mole) is weighed into a powder addition funnel and dissolved in mL of dry dichloromethane. Crystalline xylenol (73.3 g, 0.6 mole) is weighed into a 250 mL three-necked round-bottomed flask which is equipped with a stirrer, heating mantle, nitrogen inlet, condenser, thermometer, and drying tube. Dry dichloromethane (80 mL) is added and the mixture is heated to 400° C. with stirring. The solution of dichlorofluorene in dichloromethane is added slowly to the mixture as the temperature is maintained at about 400° C. The reaction is rapid as evidenced by copious production of HCl. The mixture becomes cloudy rapidly as a large quantity of white precipitate is formed. After addition is complete the reaction is stirred for an additional half hour and then checked by gas chromatography. The reaction is complete, and the only products observed are the bisphenol (9,9-bis(2-hydroxy-4,5-dimethylphenyl)fluorene) and the spirocyclic ether (2',3',6',7'-tetramethylspiro[fluorene-9,9'-xanthene]) in a mole ratio of 9:1. The mixture is slurried with acetonitrile, chilled and filtered to yield 39.69 g of white powder. Taking into account the amount of spiro-ether, this represents a yield of 98.07 percent. This product (35.59 g) is slurried in toluene (150 mL) along with 0.5 mL of methanesulfonic acid. The mixture is refluxed with the water produced being trapped in a Dean-Stark trap. After 3 hours of heating the cyclization to form spiro-ether is complete. The homogeneous solution is washed once with 50 mL of 0.5M aqueous NaOH to remove methanesulfonic acid catalyst, dried over magnesium sulfate, and concentrated to yield the product as a yellow solid. The solid is slurried in acetone and filtered to give the spiro-ether (2',3',6',7'-tetramethylspiro[fluorene-9,9'-xanthene]) as a white solid (33.58 g, 98.7 percent yield).

9,9-bis(2-hydroxy-4,5-dimethylphenyl)fluorene

H-1 NMR: (DMSO) delta from tetramethylsilane 1.82 (singlet, $CH_3$, 3H), 2.01 (singlet, $CH_3$, 3H), 6.32–6.46 (doublet, 4H), 7.17–7.33 (multiplet, 4H ), 7.78–7.88 (multiplet, 4H), 8.69 (singlet, 2H, OH); C-13 NMR: (DMSO) (ppm) 18.8 ($CH_3$), 19.0 ($CH_3$), 61.5 (quaternary carbon), 117.2, 119.8, 124.7, 126.2, 126.9, 127.3, 127.9, 128.2, 134.2, 139.3, 152.6, 153.5. 2',3',6',7'-tetramethylspiro[fluorene-9,9'-xanthene] H-1NMR: (CDCl$_3$) delta from tetramethylsilane 1.87 (singlet, CH$_3$, 3H), 2.16 (singlet, CH$_3$, 3H), 6.08 (singlet, 2H), 6.97 (singlet, 2H), 7.15–7.36 (multiplet, 6H), 7.76–7.79 (doublet, 2H). C-13 NMR: (CDCl$_3$) (ppm) 18.9 (CH$_3$), 19.4 (CH$_3$), 53.7 (quaternary carbon), 117.4, 119.8, 121.7, 125.6, 127.5, 128.2, 128.3, 131.1 136.6, 139.6, 149.5, 155.5

Oxidation of
2',3',6',7'-Tetramethylspiro[fluorene-9.9'-xanthene]
to form
Spiro[fluorene-9.9-xanthene]-2',3',6',7'-tetracarboxylic dianhydride Tetramethylspiro[fluorene-9,9'-xanthene] (7.77 g, 0.02 mole) is weighed into a 500 mL three-necked flask along with cobalt acetate hydrate (0.5 g, 0.002 mote), potassium bromide (0.24 g, 0.002 mole) and methyl ethyl ketone (0.5 g, 0.007 mole). Propionic acid (200 mL) is added and the flask is equipped with a condenser, gas sparge tube, magnetic stirbar, thermometer, and air outlet. The flask is lowered into a hot oil bath maintained at a temperature of 140° C. and the mixture is heated and stirred as air is introduced under the surface of the solution at a rate of 1 cubic foot per hour (28.3 L/h or 472 mL/min). The reaction is followed by sampling at intervals and analyzing by LC. After 22 hours at 125° C. (internal temperature) all of the starting material disappears and several products are formed. The temperature of the oil bath is increased to 145° C. and heating is continued for another 20 hours at this point the product mixture consists of mixed acids, so 5 mL of propionic anhydride is added, and the mixture is heated for 12 hours. Analysis of the mixture by liquid chromatography shows the formation of a single product spirol[fluorene-9,9'-xanthenel-2',3',6',7'-tetracarboxylic dianhydride. The mixture is concentrated by rotary evaporation and the residue is dissolved in dichloromethane and washed with cold water to remove inorganic salts. The dichloromethane solution of the product is then dried over 4A (Angstrom, $4\times10^{-10}$ m) molecular sieves, filtered and concentrated to yield the product as a light tan solid. H-1NMR: delta from tetramethysilane 7.88–7.95 (multiplet, 4H), 7.48–7.55 (multiplet, 2H), 7.26–7.32 (multiplet, 2H), 7.0–7.11 (multiplet, 4H). C-13 NMR: (ppm) 54.5 (quaternary C), 114.8, 121.3, 125.2, 126.7, 126.9, 129.5, 129.9, 132.1, 133.3, 139,5, 152.7, 155.6, 161.5 (C=O).

Hydrolysis of Spiro[fluorene-9.9'-xanthene]-2',3',6',7'-tetracarboxylic dianhydride to Spirolfluorene-9.9'-xanthene]-2',3',6',7'-tetracarboxylic acid A sample of the dianhydride is warmed to 50° C. in 4 equivalents of 1M caustic (NaOH) solution. The solution is then acidified, with concentrated hydrochloric acid and the tetracarboxylic acid is isolated in quantitative yield by filtration from the solution. The material gives one peak by liquid chromatography. The proton and carbon spectra are taken of the salt form in D$_2$O since the free acid is insoluble in standard NMR solvents. H-1NMR: delta from tetramethylsilane 6.97–7.08 (multiplet, 7H), 7.16–7.23 (multiplet, 2H), 7.66–7.7 (multiplet, 3H). C-13 NMR: (ppm, D$_2$O) 55.2 (quaternary C) 117.9, 123.4, 126.8, 128.3, 130.4, 131.4, 131.6, 135.3, 142.4, 153.8, 157.2, 178.3 (C=O), 179.6 (C=O).

EXAMPLE 66

Reaction of Dichlorofluorene with
Benzocyclobutane and Ferric Chloride Catalyst

DCF (23.51 g, 0.1 mole) and benzocyclobutane (BCB) (21.93 g, 0.21 mole) are weighed into a dry 100 mL 14/20 flask and stirred under nitrogen until most of the DCF has dissolved. Ferric chloride (0.08 g, 0.0005 mole) is weighed into an oven-dried 250 mL three-necked flask fitted with a nitrogen inlet, stirbar, condenser, thermometer, and drying tube. Dry dichloromethane (50 mL) is added and the mixture is stirred as the DCF/BCB solution is added by syringe while a sweep of nitrogen gas is passed over the mixture. The mixture turns purple immediately and gives off HCl. The reaction is warmed as necessary to maintain a temperature of about 40° C. An additional 50 mL of dichloromethane is used to dissolve and rinse in the last of the DCF/BCB mixture.

After addition is complete, the mixture is heated at 40° C. for an additional 2 hours and then allowed to stir overnight. GC (gas chromatographic) analysis of the product shows no residual DCF. The dichloromethane solution is washed with water (a color change of purple to muddy green-yellow is observed) and 0.5 molar HCl (hydrochloric acid). The solution is dried over MgSO$_4$, and then concentrated by rotary evaporation to yield a thick brown glass.

The product is then dissolved in a minimum amount of dichloromethane and poured with stirring into 300 mL of acetone. This causes the precipitation of off-white solid which is collected and dried (weight=5.21 g, 41 percent of theoretical). The LC (liquid chromatograph) contains several peaks, the largest of which is at 21.47 minutes [the expected position of the difunctional product (9,9-bis(benzocyclobutanyl)fluorene) is about 11.7 minutes by comparison with an LC of a sample of the material made from DCF and an excess of BCB]. The yellow filtrant is then diluted with water, and precipitation of white solid is observed. The LC analysis of this material shows the main peak to be at 11.77 minutes, corresponding to the bis-adduct made by the previous reaction. Addition of more water causes the precipitation of more solid which is collected. As more water is added, the precipitate finally becomes sticky and difficult to filter. The material is only slightly soluble in acetonitrile. Proton and C-13 NMR's were run on the two fractions. These are very similar for the two materials. Interestingly, the C-13 of the first material shows only one signal for the CH$_2$'s of the cyclobutane ring, and the second material (acetone soluble) shows two signals for these carbons. DSC's (dynamic scanning calorimetry) are run of the two materials, as well. The scans show an exotherm starting at 217° C., corresponding to the ring-opening and polymerization of the BCB groups.

EXAMPLE 67

Reaction of DCF with Benzocyclobutane (BCB)
and Phenyl Ether (DPO) (2:3:1) Antimony
Pentachloride Catalyst DCF (20.22 g, 0.086 mole), phenyl ether (7.32 g, 0.043 mole) and benzocyclobutane (27 g, 0.259 mole) are weighed into a dry 100 mL 14/20 flask and stirred under nitrogen until most of the DCF has dissolved. Antimony pentachloride(3.5 mL, 0.00344 mole) is weighed into an oven-dried 250 mL three-necked flask fitted with a nitrogen inlet, stirbar, condenser, thermometer, and drying tube. Dry dichloromethane (65 mL) is added to the reaction flask and an additional 20 mL of dry dichloromethane is added to the DCF/DPO(diphenyl oxide)/BCB solution (for complete dissolution of the DCF). The catalyst solution in the reaction flask is stirred and purged with a stream of nitrogen as the DCF/DPO/BCB solution is added by syringe over a period of 3 hours. The mixture turns purple immediately and gives off HCl.

The reaction is warmed as necessary to maintain a temperature of about 40° C. An additional 15 mL of dichloromethane is used to rinse in the last of the DCF/BCB mixture into the reaction. After addition is complete, the mixture is heated at 40° C. for an additional 2 hours and then allowed to stir overnight. GC analysis of the product shows no residual DCF. The dichloromethane solution is flushed through neutral alumina to remove residual antimony material. The solution is then concentrated by rotary evaporation to yield a thick orange glass which foams as the last of the solvent and residual BCB is removed forming a brittle gold foam which is easily crushed.

The resulting gold colored powder is analyzed by LC and shows the expected mixture of bis-BCB/DPO adduct and BCB-DPO-fluorene oligomers along with a small amount of fluorenone. The product is dissolved in wet tetrahydrofuran and treated with 0.1 g of sodium borohydride to convert residual fluorenone to alcohol. After 30 minutes of stirring, acetone is added, and the mixture is stirred for 30 minutes to destroy excess sodium borohydride. The solvent is removed by rotary evaporation and the product is dissolved in dichloromethane (dark orange solution) and treated with decolorizing carbon. The solution is flushed through neutral alumina to remove the fluorene alcohol and ionic compounds. The solvent is then removed by rotary evaporation to produce a yellow foam which is crushed. The material is analyzed by DSC, and the melting point of the material is found to be very broad, with initial softening occurring at about 80° C. and the material becoming definitely liquid by 120° C. NMR analysis (proton and carbon) shows no significant ring damage. A small portion of the product (2.0 g) is placed in an aluminum weighing dish and degassed and melted under vacuum up to 115° C. The material is cured at 160° C. for 1 hour and then cured at 235° C. for 12 hours. An orange plaque is obtained which can be removed intact.

EXAMPLE 68

Conversion of
Spiro[fluorene-9,9'-xanthene]-2',7'-dicarboxylic acid
to Spiro[fluorene-9,9'-xanthene]-2',7'-dicarbonyl
chloride Spiro[fluorene-9,9'-xanthene]-2',7'-dicarboxylic acid prepared in Example 57 (1.25 g, 3 mmole) is stirred and heated to reflux in 15 mL of oxalyl chloride until the solution clears. The excess oxalyl chloride is removed by rotary evaporation and the resulting solid is dissolved in dichloromethane and filtered to remove any unreacted diacid. The dichloromethane solution is concentrated by rotary evaporation to give the diacid chloride [spiro[fluorene-9,9'-xanthene]-2',7'-dicarbonyl chloride] as an off-white solid. Recovered yields are quantative. Spiro[9H-fluorene-9,9'-[9H]xanthene]-2',7'-dicarbonyl chloride: H-1NMR: (CDCl$_3$) delta 7.06–7.48 (multiplet, 10H), 7.82–8.05 (multiplet, 4H). C-13 NMR: (CDCl$_3$) (ppm) 166.8, 155.5, 153.5, 139.6, 132.3, 129.3, 129.0, 128.9, 128.8, 128.7, 125.2, 120.8, 117.8, 53.4 (quaternary carbon).

EXAMPLE 69

Reaction of Dichlorofluorene with m-Cresol and
cyclization of the Products to form
3',6'-Dimethylspiro[fluorene-9,9'-xanthene]

Dichlorofluorene (DCF) (35.27 g, 0.15 mole) is weighed into a powder addition funnel and dissolved in 20 mL of dry dichloromethane. Liquid m-cresol (64.88 g, 0.6 mole) is weighed into a 250 mL three-necked round-bottomed flask which is equipped with a stirrer, heating mantle, nitrogen inlet, condenser, thermometer, and drying tube. Dry dichloromethane (80 mL) is added and the mixture is heated to 40° C. with stirring. DCF solution is added slowly to the mixture as the temperature is maintained at about 40° C. The reaction is rapid as evidenced by copious production of HCl bubbles after each addition. After addition is complete, the reaction is stirred for an additional half hour and then checked by LC. The reaction is complete, and the chromatograph shows peaks for the desired bisphenol (9,9-bis(2-hydroxy-4-methylphenyl)fluorene) along with isomers. The mixture is dissolved in toluene and refluxed with 0.5 mL of methane sulfonic acid collecting water formed during the cyclization reaction in a Dean-Stark trap. The toluene is then removed by rotary evaporation and the residue is slurried with acetonitrile, chilled and filtered to yield the spiroether [3',6'-dimethylspiro[fluorene-9,9'-xanthene] as an off-white powder. The isomeric bisphenols formed in the alkylation reaction do not cyclize and remain dissolved in the acetonitrile.

Upon cooling the product, 3',6'-dimethylspiro[9H-fluorene-9,9'-[9H]xanthene] (13.03 g) precipitates from the toluene solution as a white powder which is filtered from the solution, and rinsed with toluene, sodium bicarbonate solution and water. The toluene solution is washed with sodium bicarbonate and 2M NaOH, dried over magnesium sulfate, and concentrated by rotary evaporation resulting in a brown oil. This oil is slurried with acetonitrile, chilled and filtered to yield 7.51 g of product as an off-white powder. Isolated yield is 38 mole percent. H-1 NMR: (CDCl$_3$) delta 2.27 (singlet, CH$_3$, 6H), 6.25–6.28 (doublet, 2H), 6.54–6.58 (doublet of doublets, 2H), 7.01–7.36 (multiplet, 8H), 7.75–7.78 (multiplet, 2H). C-13 NMR: (CDCl$_3$) (ppm) 155.3, 151.2, 139.6, 138.1, 128.3, 127.6, 125.6, 124.2, 121.7, 119.8, 117.0, 53.7 (quaternary carbon), 21.0 (CH$_3$).

EXAMPLE 70

Oxidation of
3',6'-Dimethylspiro[fluorene-9,9'-xanthene] to
Spiro[fluorene-9,9'-xanthene]-3',6'-dicarboxylic acid Dimethylspiro[fluorene-9,9'-xanthene] prepared as in Example 69 (10.00 g, 0.0277 mol) is weighed into a 500 mL three-necked flask along with cobalt acetate hydrate (0.69 g, 0.00277 mol), sodium bromide (0.29 g, 0.00277 mol) and methyl ethyl ketone (0.70 g, 0.0097 mol). Propionic acid (250 mL) is added and the flask is equipped with a condenser, gas sparge tube, magnetic stirbar, thermometer, and air outlet. The flask is lowered into a hot oil bath maintained at a temperature of 145° C. and the mixture is heated and stirred as air is introduced under the surface of the solution at a rate of 1 cubic foot per hour (28.3 L/h or 472 mL/min). The reaction is followed by sampling at intervals and analyzing by LC. After 36 hours at 135° C. (internal temperature) all of the starting material disappears and a single product is seen by LC. The mixture is allowed to cool, whereupon a large quantity of white precipitate forms and is filtered from the mixture and rinsed with propionic acid and water. This material is insoluble in dichloromethane. The powder is dried in air. When reacted with sodium hydroxide in D$_2$O, a gelatinous product forms. Spectra are consistent with the structure of the diacid, spiro[fluorene-9,9'-xanthene]-3',6'-dicarboxylic acid. Recovered yields are 85–95 mole percent.

EXAMPLE 71

Conversion of Spirol[fluorene-9,9'-xanthene]-3',6'-dicarboxylic acid to Spirol[fluorene-9,9'-xanthene]-3',6'-dicarbonyl chloride Spiro[fluorene-9,9'-xanthene]-3',6'-dicarboxylic acid prepared as in Example 70 (1.25 g, 3 mmole) is stirred and heated to reflux in 15 mL of oxalyl chloride until the solution clears. The excess oxalyl chloride is removed by rotary evaporation and the resulting solid is dissolved in dichloromethane and filtered to remove any unreacted diacid. The dichloromethane solution is concentrated by rotary evaporation to give the diacid chloride [spiro[fluorene-9,9'-xanthene]-3',6'-dicarbonyl chloride] as an off-white solid. Recovered yields are greater than 95 mole percent.

EXAMPLE 72

Preparation of Spiro[9H-fluorene-9,9'-[9H]xanthene]

Dichlorofluorene (200.0 g, 0.85 mol) is mixed with aniline (1200 mL, 13.17 mole) and heated slowly to 55°–60° C. and held there for 30 minutes. GC analysis shows 4 mole percent of fluorenedianiline and 96 mole percent 9-(4-aminophenyl)-9-chlorofluorene. The mixture is then neutralized by washing with 1 L of 10 mole percent sodium hydroxide. The organic layer is separated and the excess aniline is removed by rotary evaporation. The resulting product 9-(4-aminophenyl)-9-chlorofluorene is transferred to a 3 L flask along with phenol (1500 mL, 17 mole) and methanesulfonic acid (300 mL). The mixture is heated to 170° C. for 7 hours, then allowed to cool to room temperature overnight. The product, spiro[9H-fluorene-9,9'-[9H]xanthene] precipitates from the cooled mixture and is isolated by filtration. The precipitated crystals are washed twice with sodium bicarbonate and twice with water to remove residual methanesulfonic acid. Crude weight is 345 g, with GC analysis showing 17 mole percent phenol remaining in the product. The product is washed twice with 500 mL of methanol to remove phenol. Isolated yield is 223 g (75 mole percent ). Spiro[9H-fluorene-9,9'-[9H]xanthene] GC/MS 332 (100 percent), 302 (21.88 percent), 300 (18.75 percent), 255 (18.75 percent), 200 (2.9 percent), 165 (14.61 percent).

What is claimed is:

1. A compound selected from 9,9-bis(4-ethylphenyl)fluorene, 9,9-bis(4-ethenylphenyl)fluorene, 9,9-bis(4-ethynylphenyl)fluorene, 9,9-bis(2,3-dimethylphenyl)fluorene, 9-(3,4-dimethylphenyl )9-(2,3-dimethylphenyl)fluorene, 9,9-bis(3-amino-4hydroxyphenyl)fluorene, 9,9-bis(4-amino-3hydroxyphenyl)fluorene, 9-(3-amino-4-hydroxyphenyl )-9(4-amino-3-hydroxyphenyl)fluorene, 9,9-bis(1,3-isobenzofurandion-5-yl)fluorene, 9,9-bis(benzocyclobutanyl)fluorene, 9,9-bis(4-halophenyl)fluorene, 9,9-bis(dihydroxyphenyl)fluorene, spiro[9H-fluorene-9,9'-(9H)carbazine)-3',6'-diol, spiro(9H-fluorene-9,9'-(9H)carbazine)-3',6'-diamine, spiro(9H-fluorene-9,9'-(9H)carbazine)-2',7'-diamine, spiro(9H-fluorene-9,9'-(9H)xanthene)-2',7'-dicarboxylic acid, spiro(9H-fluorene-9,9'-(9H)xanthene)-3',6'-diamine, 2',7'-diacetylspiro(9H-fluorene-9,9'-(9H)xanthene), spiro(9H-fluorene-9,13'-(13H)-6-oxapentacene)-2',10'-diol spiro(9H-fluorene-9, 13'-(13H)-6-oxapentacene)-3',9'-diol, 3',6'diaminospiro(9H-fluorene-9,9'-thiaxanthene)-10',10'-dioxide, spiro(9H-fluorene-9,9'(9H, 10H)-dihydroanthracene-2',7'-bismaleimide, 10-oxo-spiro(9H-fluorene-9,9'(9H, 10H)-dihydroanthracene)-3',6'-diamine, 2',7'-dimethyl-spiro(9H-fluorene-9,9'-(9H)xanthene), 2',7'-dicyano-spiro(9H-fluorene-9,9'-(9H)xanthene), 2',7'-diformyl-spiro(9H-fluorene-9,9'-(9H)xanthene), 2,7-diamino-3,6-dihydroxy-9,9'-spirobifluorene, 2,7-diamino-3,6-dimethyl-9,9'-spirobifluorene, spiro(9H-fluorene-9,9'(9H, 10H)-dihydroanthracene)-2',7'-diamine, 2',3',6',7'-tetraaminospiro(9H-fluorene-9,9'-thiaxanthese)-10',10'-dioxide, spiro(9H-fluorene-9,9'(9H)xanthene)-2',3',6,7'-tetraamine, 2,3,6,7-tetraamino-9,9'-spirobifluorene, 2,7-diamino-9,9'-spirobifluorene-3,6-dithiol, 2,7-bis(1-methyl-1-(4-hydroxyphenyl)-ethyl)spiro(xanthene-9,9'-fluorene), 2,7-bis(4-hydroxyphenyl)spiro(xanthene-9,9'-fluorene), 1,3, 6,8,10,10-hexamethylspiro(dihydroanthracene-9,9'-fluorene)-2,7-diol, 1,3,6,8-tetrabromo-10,10-dimethylspiro(dihydroanthracene-9,9'-fluorene)-2,7-diol, and 1,3,6,8-tetramethylspiro(dihydroanthracene-9,9'-fluorene)-2,7-diol, spiro(9H-fluorene-9,9'-(9H)xanthene)-3',6'-dicarboxylic acid, spiro(9H-fluorene-9,9'-(9H)xanthene)-2',7'-dicarbonyl chloride, spiro(9H-fluorene-9,9'-(9H)xanthene)-3',6'-dicarbonyl chloride, 3',6'-dimethyl-spiro(9H-fluorene-9,9'-(9H)xanthene), 2',7'-diisopropylspiro(9H-fluorene-9,9'-(9H)xanthene), 3',6'-diisopropylspiro(9H-fluorene-9,9'-(9H)xanthene), 2',3',6',7'-tetramethylspiro(9H-fluorene-9,9'-(9H)-xanthene), spiro(9H-fluorene-9,9'-(9H)xanthene)-2',3', 6',7'-tetracarboxylic acid, or spiro(9H-fluorene9,9'-(9H)xanthene)-2',3',6',7'-tetracarboxylic acid dianydride, and mixtures thereof.

2. A compound selected from 9-(4-aminophenyl)-9-chlorofluorene, 9-(4-(N-methylaminophenyl))-9-chlorofluorene, 9-(4-amino-3-methylphenyl)-9-chlorofluorene, 9-(4-amino-3-ethylphenyl)-9-chlorofluorene, 9-(4-amino-3-chlorophenyl)-9-chlorofluorene, 9-(4-amino-4-methylphenyl)-9-chlorofluorene, 9-(4-amino-2-ethylphenyl)-9-chlorofluorene, 9-(4-amino-2-chlorophenyl)-9-chlorofluorene, and mixtures thereof.

3. A compound of claim 1 selected from 9,9-bis(4-ethylphenyl)fluorene, 9,9-bis(2,3-dimethylphenyl)fluorene, and 9-(3,4-dimethylphenyl) 9-(2,3-dimethylphenyl) fluorene.

4. A compound of claim 1 selected from 9,9-bis(4-ethenylphenyl)fluorene, and 9,9-bis(4-ethynylphenyl)fluorene.

5. A compound of claim 1 selected from 9,9-bis(3-amino-4hydroxyphenyl)fluorene, 9,9-bis(4-amino-3-hydroxyphenyl)fluorene, 9-(3-amino-4-hydroxyphenyl)-9(4-amino-3-hydroxyphenyl)fluorene and mixtures thereof.

6. A compound of claim 1 which is 9,9bis(benzocyclobutanyl)fluorene.

7. A compound of claim 1 selected from 9,9-bis(4-halophenyl)fluorene.

8. A compound of claim 1 selected from 9,9-bis(dihydroxyphenyl)fluorene.

9. A compound of claim 1 selected from spiro(9H)fluorene-9,9'-(9H)xanthene)-2',7'-dicarboxylic acid, 2',7'-dimethyl-spiro(9H-fluorene-9,9'-(9H)xanthene), spiro(9H-fluorene-9,9'-(9H)xanthane)-3',6'-dicarboxylic acid, spiro(9H-fluorene-9,9'(9H)xanthene)-2',7'-dicarbonyl chloride, spiro(9H-fluorene-9,9'-(9H)xanthene)-3',6'-dicarbonyl chloride, 3',6'-dimethyl-spiro(9H-fluorene-9,9'-(9H)xanthene), 2',3',6',7'-tetramethylspiro(9H-fluorene-9,9'-(9H)xanthene), spiro(9H-fluorene-9,9'-(9H)xanthene)-2',3', 6',7'-tetracarboxylic acid, or spiro(9H-fluorene-9,9'-(9H)xanthene)-2',3',6',7'-tetracarboxylic acid dianydride, and mixtures thereof.

10. A compound of claim 9 which is selected from spiro(9H-fluorene-9,9'-(9H)xanthene)-2',7'-dicarboxylic acid and mixtures thereof.

11. A compound of claim 9 which is 2,7-bis(4-hydrroxyphenyl)spiro(xanthene-9,9'-fluorene).

12. A compound of claim 9 which is selected from spiro(9H-fluorene-9,9'-(9H)xanthene)-3',6'-dicarboxylic acid, spiro(9H-fluorene-9,9'-(9H)xanthene)-2',7'-dicarbonyl chloride, spiro(9H-fluorene-9,9'-(9H)xanthene)-3',6'-dicarbonyl chloride, and mixtures thereof.

13. A compound of claim 9 which is selected from spiro(9H-fluorene-9,9'-(9H)xanthene)-2',3',6',7'-tetracarboxylic acid, or spiro(9H-fluorene-9,9'-(9H)xanthene)-2',3',6',7'-tetracarboxylic acid dianydride, and mixtures thereof.

* * * * *